US012486340B2

(12) United States Patent
Sivaguru et al.

(10) Patent No.: US 12,486,340 B2
(45) Date of Patent: Dec. 2, 2025

(54) BIOMASS-DERIVED PHOTOINITIATORS

(71) Applicant: Bowling Green State University, Bowling Green, OH (US)

(72) Inventors: Jayaraman Sivaguru, Bowling Green, OH (US); Ravichandranath Singathi, Bowling Green, OH (US)

(73) Assignee: Bowling Green State University, Bowling Green, OH (US)

( * ) Notice: Subject to any disclaimer, the term of this patent is extended or adjusted under 35 U.S.C. 154(b) by 361 days.

(21) Appl. No.: 17/926,337

(22) PCT Filed: May 18, 2021

(86) PCT No.: PCT/US2021/032858
§ 371 (c)(1),
(2) Date: Nov. 18, 2022

(87) PCT Pub. No.: WO2021/236563
PCT Pub. Date: Nov. 25, 2021

(65) Prior Publication Data

US 2023/0192908 A1 Jun. 22, 2023

Related U.S. Application Data

(60) Provisional application No. 63/026,949, filed on May 19, 2020.

(51) Int. Cl.

| | |
|---|---|
| ***C08F 2/46*** | (2006.01) |
| ***C07C 49/84*** | (2006.01) |
| ***C07D 307/42*** | (2006.01) |
| ***C08F 2/50*** | (2006.01) |
| ***C08F 120/14*** | (2006.01) |
| ***C08F 120/28*** | (2006.01) |
| ***C08F 122/20*** | (2006.01) |
| ***C08G 61/04*** | (2006.01) |

(52) U.S. Cl.
CPC ................ *C08F 2/50* (2013.01); *C07C 49/84* (2013.01); *C07D 307/42* (2013.01); *C08F 120/14* (2013.01); *C08F 120/28* (2013.01); *C08F 122/20* (2013.01)

(58) Field of Classification Search
CPC C08F 120/14; C08F 120/28; C08F 222/1006; C08F 2/50; C08F 122/20; C08K 5/375; C08K 5/17; C08K 5/132; C07C 49/84; C07D 307/42
USPC ........... 522/46, 33, 6, 71, 1, 189, 184; 520/1
See application file for complete search history.

(56) References Cited

U.S. PATENT DOCUMENTS

| | | | | |
|---|---|---|---|---|
| 5,877,353 | A * | 3/1999 | Bruhin | C07C 205/45 568/333 |
| 5,900,472 | A | 5/1999 | Fan et al. | |
| 2018/0272595 | A1 | 9/2018 | Yudovin-Farber et al. | |
| 2019/0047965 | A1 | 2/2019 | Sivaguru et al. | |

FOREIGN PATENT DOCUMENTS

| | | | |
|---|---|---|---|
| CN | 103524320 | A | 1/2014 |
| CN | 104231121 | B | 7/2016 |

OTHER PUBLICATIONS

Wang et al, One-pot synthesis of diarylmethanones through palladium-catalyzed sequential coupling and aerobic oxidation of aryl bromides with acetophenone as a latent carbonyl donor, J. Org. Chem., 2014, 79, 6554-6562 (Year: 2014).*

Sahu et al., "Sustainable self-healing elastomers with thermoreversible network derived from biomass via emulsion polymerization", Journal of Polymer Science Part A: Polymer Chemistry, 2019, vol. 57, Issue 6, [retrived on Aug. 23, 2021]. Retrieved from the Internet:<URL: https/onlinelibrary.wiley.com/doi/abs/10.1002/pola.29320>.

Hong et al., "Proton-Transfer Polymerization by N-Heterocyclic Carbenes: Monomer and Catalyst Scopes and Mechanism for Converting Dimthacrylates into Unsaturated Polyesters", Journal of the American Chemical Society, 2016, vol. 138, Issue 6, [retrived on Aug. 23, 2021]. Retrieved from the Internet: <URL: https//pubs.acs.org/doi/10.1021/jacs.5b13019>.

Pubchem, SID 86441605, Available Date: Jan. 5, 2010 [retrieved on Jun. 22, 2021]. Retrieved from the Internet: <URL: https://Pubchem.ncbi.nlm.nih.gov/substance/86441605>.

International Search Report and Written Opinion, Application No. PCT/US2021/032858, dated Sep. 29, 2021.

* cited by examiner

*Primary Examiner* — Jessica Whiteley
(74) *Attorney, Agent, or Firm* — MacMillan, Sobanski & Todd, LLC

(57) ABSTRACT

Biomass derived benzophenone derivatives, and methods of making and using the same, are described. In accordance with the present disclosure, biomass derived benzophenone derivatives are useful as visible light photoinitiators.

19 Claims, 71 Drawing Sheets
(66 of 71 Drawing Sheet(s) Filed in Color)

Veratraldehyde 1a 1b 1c 1d 1e 1f Benzophenone (BP)

2a 2b 2c
3 4
5 6
7 8

7

8

6

8

1a : R = H, 1b: R = $CH_3$,
1c : R = $OCH_3$ 1d : R =$SCH_3$,
1e : R = $CF_3$, 1f : R = F

2a

2b

2c

3

4

5

6

7

8

9

10a : R = H, 10b: R = $CH_3$
10c : R = $OCH_3$, 10d : R =$SCH_3$
10e : R = $CF_3$, 10f : R = F

11

12

Yields : 60 - 70 %

9

Veratraldehyde

R = H, R = $CH_3$
R = $OCH_3$, R = $SCH_3$
R = $CF_3$,: R = F

10a : R = H
10b: R = $CH_3$
10c : R = $OCH_3$
10d : R = $SCH_3$
10e : R = $CF_3$
10f : R = F

10a : R = H
10b: R = $CH_3$
10c : R = $OCH_3$
10d : R = $SCH_3$
10e : R = $CF_3$
10f : R = F

1a : R = H
1b: R = $CH_3$
1c : R = $OCH_3$
1d : R = $SCH_3$
1e : R = $CF_3$
1f : R = F

9

5

11 12

12

7

3 4

5 6

7 8

6

5

6

8

1a

BIOMASS-DERIVED PHOTOINITIATORS

RELATED APPLICATIONS

This is the national phase application of international application PCT/US2021/032858, filed under the authority of the Patent Cooperation Treaty on May 18, 2021, published; which claims priority to U.S. Provisional Application No. 63/026,949, filed under 35 U.S.C. § 111(b) on May 19, 2020. The entire disclosure of each of the aforementioned applications is incorporated herein by reference for all purposes.

STATEMENT REGARDING FEDERALLY SPONSORED RESEARCH

This invention was made with no government support. The government has no rights in this invention.

BACKGROUND

Photopolymerization has proven to be a viable method of synthesizing various polymers including smart materials. An alternative to established benzophenone type photoinitiating systems is of high need.

SUMMARY

Provided is a composition comprising Formula I:

(I)

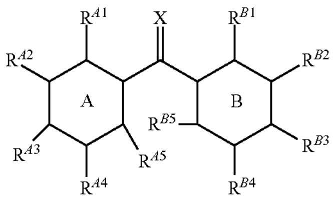

wherein A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; and substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes.

In certain embodiments, the composition comprises a biomass derived compound of Formula A:

Formula A

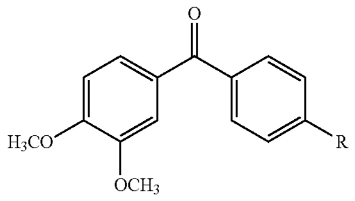

where R is H, alkyl, alkoxy, halo, halo-substituted alkyl, or thioalkyl.

In particular embodiments, the compound is 1a:

1a

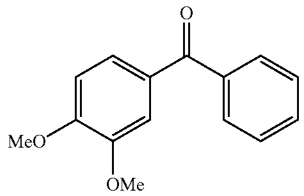

In particular embodiments, the compound is 1b:

1b

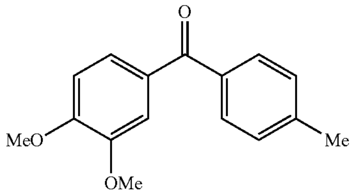

In particular embodiments, the compound is 1c:

1c

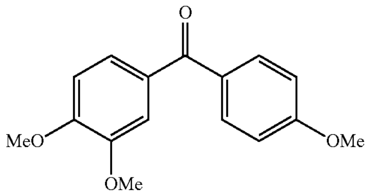

In particular embodiments, the compound is 1d:

1d

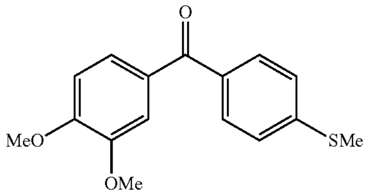

In certain embodiments, the compound is 1e:

1e

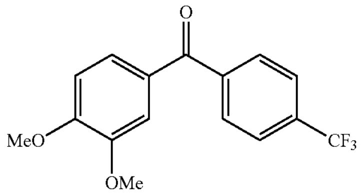

In certain embodiments, the compound is 1f:

1f

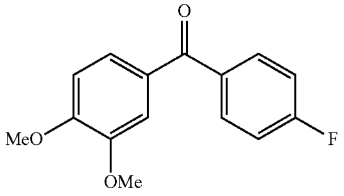

In certain embodiments, the composition comprises Formula D:

Formula D

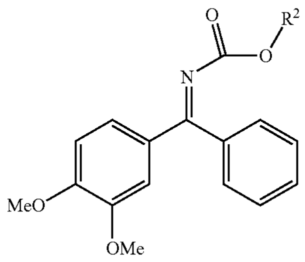

where $R^2$ is alkyl, aryl, or heteroaryl.

In certain embodiments, the composition comprises compound 1j:

1j

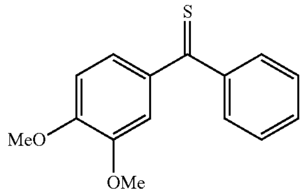

Further provided is a composition comprising Formula II:

Formula II

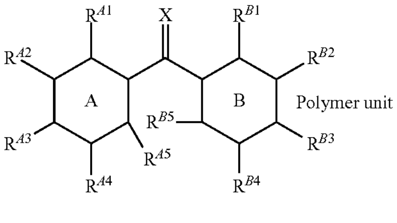

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is a vinyl, stryl, acryl, or a cyclic monomer selected from lactones (cyclic esters), epoxides, lactides, lactams, silicon-containing cyclic monomers, and cyclic carbonates.

In certain embodiments, the composition comprises compound 1g:

1g

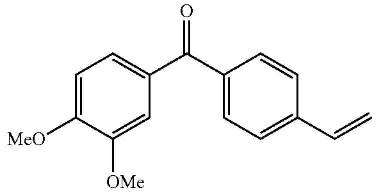

In certain embodiments, the composition comprises Formula C:

Formula C

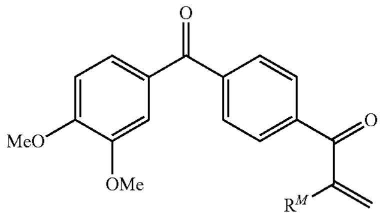

wherein $R^M$ is alkyl, aryl, heteroaryl, alkoxy, carboxy alkyl, or an amide.

Further provided is a composition comprising Formula III:

Formula III

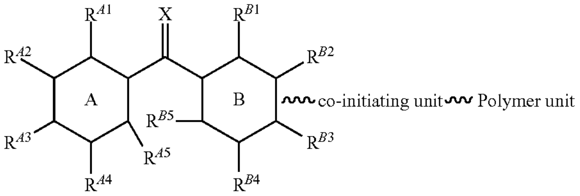

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; the co-initiating unit is an amine, thiol, or any hydrogen atom donor; and the polymer unit is a vinyl, stryl, acryl, or a cyclic monomer selected from lactones (cyclic esters), epoxides, lactides, lactams, silicon-containing cyclic monomers, and cyclic carbonates.

In certain embodiments, the composition comprises compound 1h:

1h

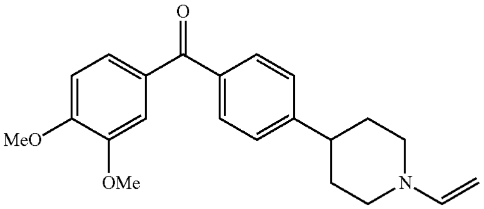

Further provided is a composition comprising Formula IV:

Formula IV

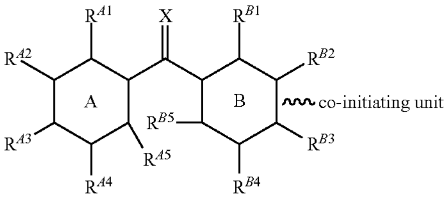

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the co-initiating unit is an amine, thiol, or any hydrogen donating atom.

In certain embodiments, the composition comprises compound 1i:

1i

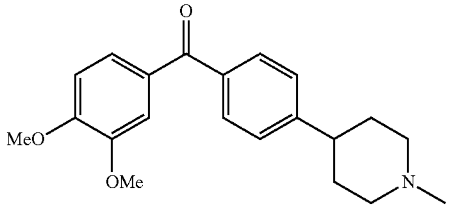

Further provided is a method of making a polymer, the method comprising exposing a biomass derived photoinitiator and a monomer to light to make a polymer, wherein the biomass derived photoinitiator comprises Formula I:

Formula I

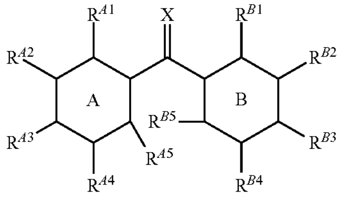

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; and substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes.

In certain embodiments, the photoinitiator comprises Formula A:

Formula A

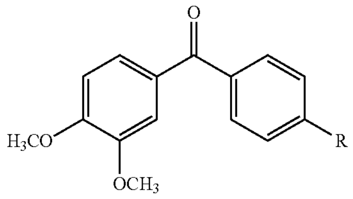

where R is H, alkyl, alkoxy, halo, halo-substituted alkyl, or thioalkyl.

In certain embodiments, the photoinitiator is 1a:

1a

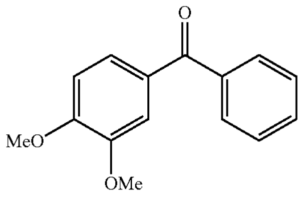

In certain embodiments, the photoinitiator is 1b:

1b

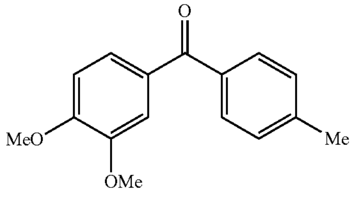

In certain embodiments, the photoinitiator is 1c:

1c

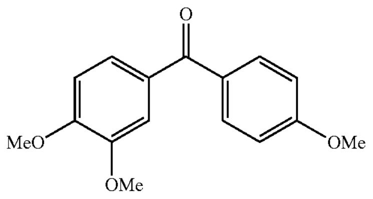

In certain embodiments, the photoinitiator is 1d:

1d

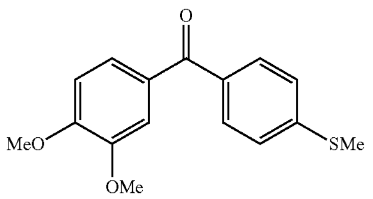

In certain embodiments, the photoinitiator is 1e:

1e

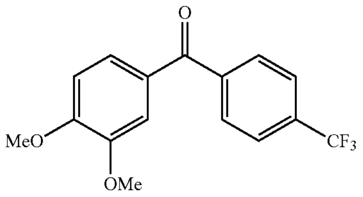

In certain embodiments, the photoinitiator is 1f:

1f

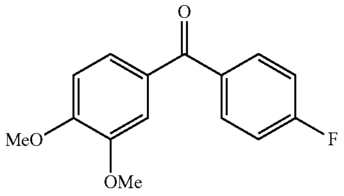

In certain embodiments, the light is visible light. In certain embodiments, the light is purple light.

In certain embodiments, the monomer is monomer 3:

3

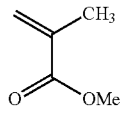

In certain embodiments, the monomer is monomer 5:

5

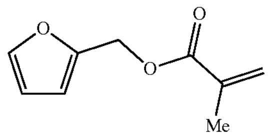

In certain embodiments, the monomer is furfuryl dimethacrylate monomer 7:

7

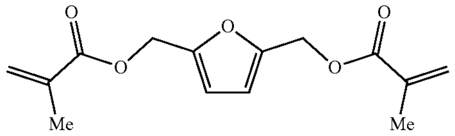

In certain embodiments, the polymer is polymer 4:

4

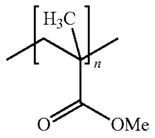

where n is an integer.

In certain embodiments, the polymer is polymer 6:

6

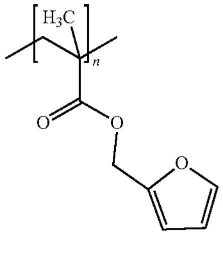

where n is an integer.

In certain embodiments, the polymer is 2,5-bis(hydroxymethyl)furan dimethacrylate (FDMA) polymer 8:

8

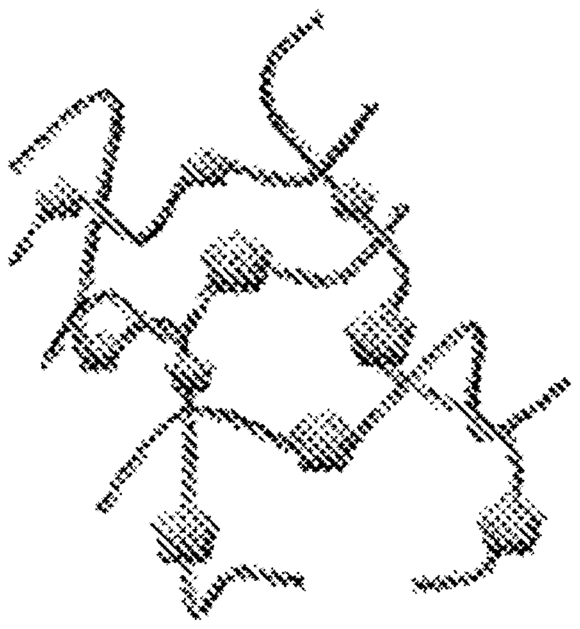

In certain embodiments, the biomass derived photoinitiator comprises Formula D:

Formula D

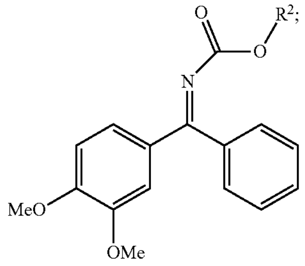

where IV is alkyl, aryl, or heteroaryl.

In certain embodiments, the biomass derived photoinitiator comprises compound 1j:

1j

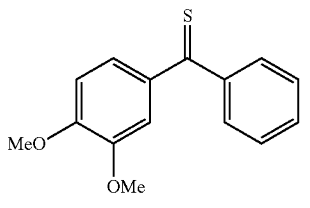

Further provided is a method of making a polymer, the method comprising exposing a biomass derived photoinitiator and a monomer to light to make a polymer, wherein the biomass derived photoinitiator comprises Formula II:

Formula II

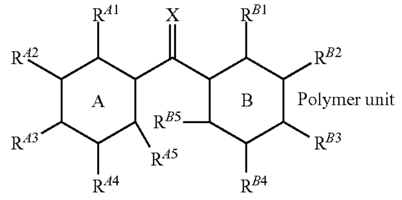

wherein A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is a vinyl, stryl, acryl, or a cyclic monomer selected from lactones (cyclic esters), epoxides, lactides, lactams, silicon-containing cyclic monomers, and cyclic carbonates.

In certain embodiments, the biomass derived photoinitiator comprises compound 1g:

1g

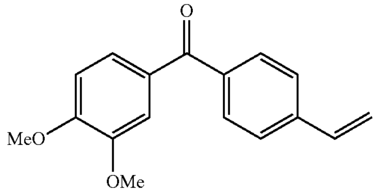

In certain embodiments, the biomass derived photoinitiator comprises Formula C:

Formula C

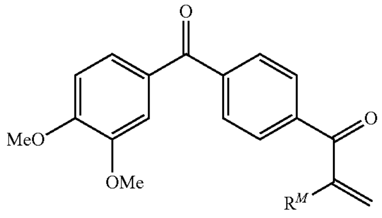

wherein $R^M$ is alkyl, aryl, heteroaryl, alkoxy, carboxy alkyl, or an amide.

Further provided is a method of making a polymer, the method comprising exposing a biomass derived photoinitiator and a monomer to light to make a polymer, wherein the biomass derived photoinitiator comprises Formula III:

Formula III

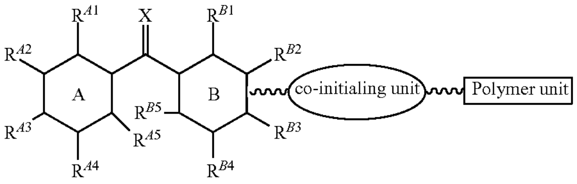

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; the co-initiating unit is an amine, thiol, or any hydrogen atom donor; and the polymer unit is a vinyl, stryl, acryl, or a cyclic monomer selected from lactones (cyclic esters), epoxides, lactides, lactams, silicon-containing cyclic monomers, and cyclic carbonates.

In certain embodiments, the biomass derived photoinitiator comprises compound 1h:

1h

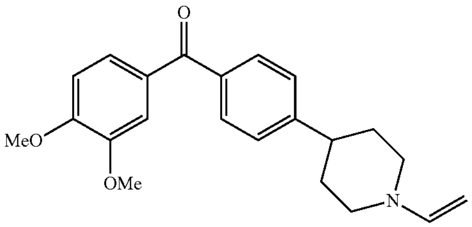

Further provided is a method of making a polymer, the method comprising exposing a biomass derived photoinitiator and a monomer to light to make a polymer, wherein the biomass derived photoinitiator comprises Formula IV:

Formula IV

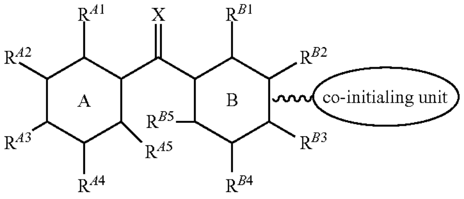

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the co-initiating unit is an amine, thiol, or any hydrogen donating atom.

In certain embodiments, the biomass derived photoinitiator comprises compound 1i:

1i

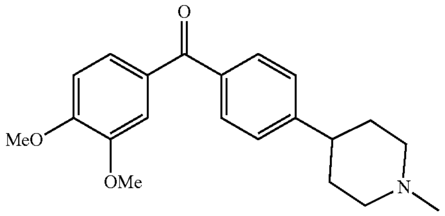

In certain embodiments of any method of making a polymer described herein, a co-initiator is exposed to the light with the monomer and the photoinitiator. In particular embodiments, the co-initiator comprises an amine, a thiophenol, or an iso-propyl alcohol.

Further provided is a method of making a biomass derived benzophenone derivative, the method comprising synthesizing a benzhydrol derivative having Formula B:

Formula B

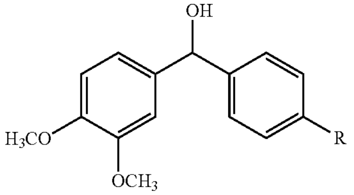

and oxidizing the benzhydrol derivative to form a biomass derived benzophenone derivative; where R is H, alkyl, alkoxy, halo, halo-substituted alkyl, or thioalkyl.

In certain embodiments, the benzhydrol derivative is oxidized with $MnO_2$. In certain embodiments, the benzhydrol derivative is synthesized through a Grignard reaction with veratraldehyde 9:

9

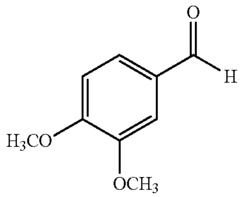

In particular embodiments, 4-bromo benzene derivatives are reacted with the veratraldehyde 9 in the Grignard reaction.

Further provided is the use of a biomass derived benzophenone derivative as a visible light photoinitiator.

Further provided is a kit for making a polymer, the kit comprising a first container housing a monomer, and a second container housing a photoinitiator having any of Formula I, Formula II, Formula III, or Formula IV:

Formula I

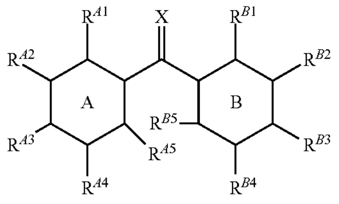

Formula II

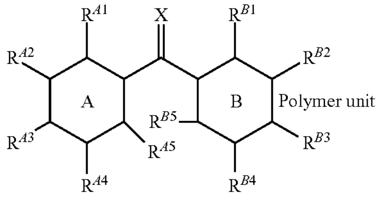

Formula III

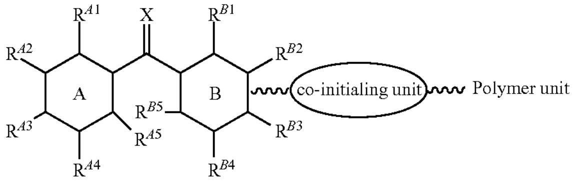

Formula IV

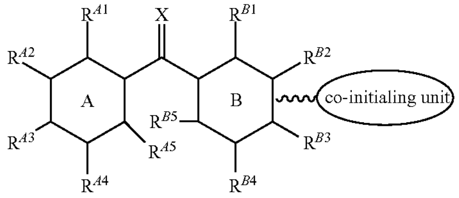

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; the co-initiating unit is an amine, thiol, or any hydrogen atom donor; and the polymer unit is a vinyl, stryl, acryl, or a cyclic monomer selected from lactones (cyclic esters), epoxides, lactides, lactams, silicon-containing cyclic monomers, and cyclic carbonates.

In certain embodiments, the photoinitiator comprises a compound of Formula A:

Formula A

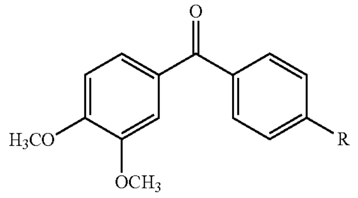

where R is H, alkyl, alkoxy, halo, halo-substituted alkyl, or thioalkyl.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 9A-9B: $^1H$ NMR spectrum (FIG. 9A) and $^{13}C$ NMR spectrum (FIG. 9B) of 10a.

FIGS. 16A-16C: $^1H$ NMR spectrum (FIG. 16A), $^{13}C$ NMR spectrum (FIG. 16B), and HRMS-ESI spectrum (FIG. 16C) of 1a.

DETAILED DESCRIPTION

Throughout this disclosure, various publications, patents, and published patent specifications are referenced by an identifying citation. The disclosures of these publications, patents, and published patent specifications are hereby incorporated by reference into the present disclosure in their entirety to more fully describe the state of the art to which this invention pertains.

The present disclosure provides a visible light (LED) alternative for UV-curing applications such as inks, imaging, dental composites, automobile parts manufacturing, clear coatings in the printing industry, paints, packaging, and so on.

In general, the photoinitiator compounds of the present disclosure have Formula I:

Formula I

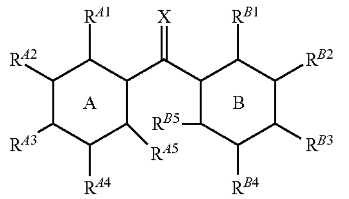

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; and substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes.

In some embodiments, the photoinitiator compounds of the present disclosure have formula A:

Formula A

Figure 1:
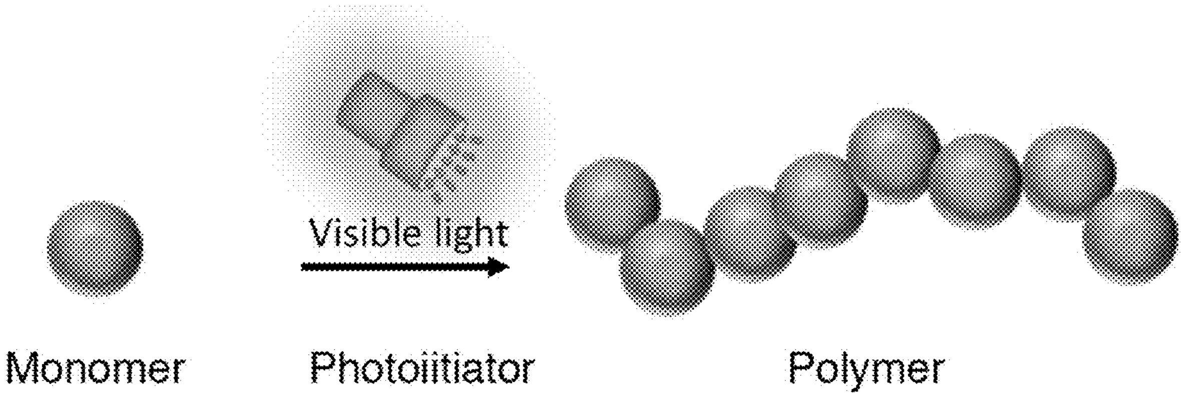
FIG. 1: Illustration of type I and type II photoinitiating systems for polymerization.
Figure 2:
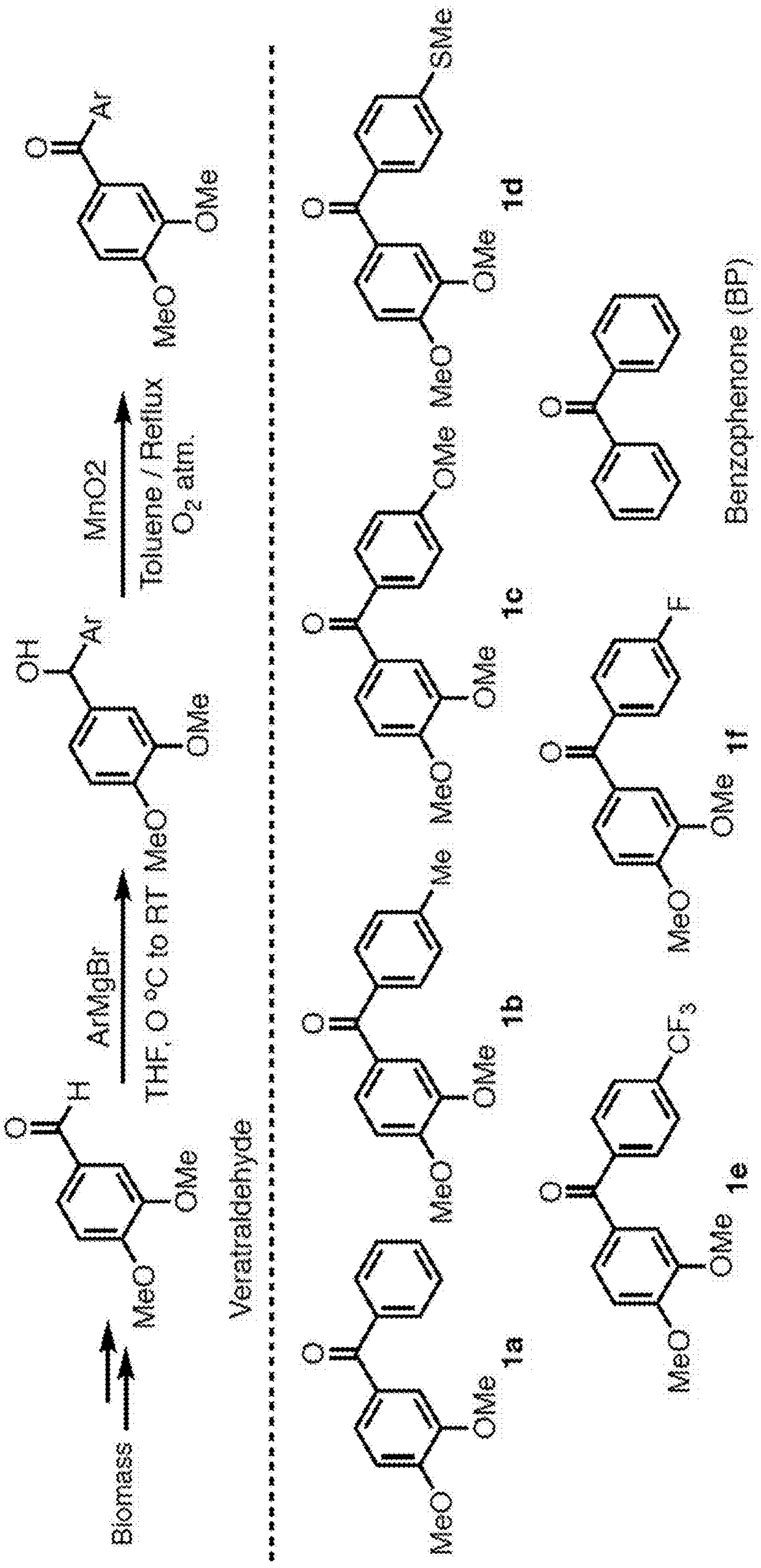
FIG. 2: Scheme 1, depicting biomass-derived photoinitiators.

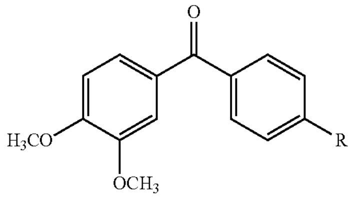

where R is H, alkyl, alkoxy, halo, halo-substituted alkyl, or thioalkyl. In some embodiments, R is H, methoxy, methyl, thiomethyl, trifluoromethyl, or fluoro. Non-limiting example photoinitators are the benzophenone derivatives 1a-1f depicted in FIGS. 2, 7. Benzophenone derivatives 1a-1f can be synthesized as depicted in FIG. 2, by oxidizing a benzhydrol derivative 10a-10f, which can itself be formed through a Grignard reaction beween a 4-bromo benzene derivative and veratraldehyde 9.

The photoinitiators herein can also be biomass based aromatic carbonyl compounds that can be immobilized on a polymer support. The polymer may be, for example, a vinyl, stryl, acryl, or epoxy polymer unit. In such embodiments, the biomass based aromatic carbonyl compounds may have the following Formula II:

Formula II

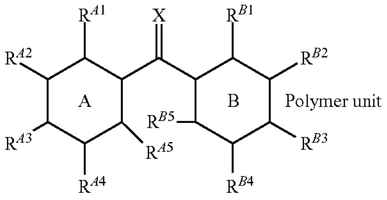

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the polymer unit is a vinyl, stryl, acryl, or cyclic monomers such as lactones (cyclic esters), epoxides, lactides, lactams, silicon-containing cyclic monomers, cyclic carbonates, or others. A non-limiting example of such compounds is compound 1g:

1g

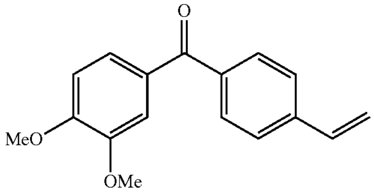

Other examples of such compounds are encompassed by Formula C:

Formula C

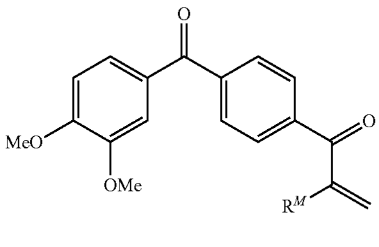

where $R^M$ is alkyl, aryl, heteroaryl, alkoxy, carboxy alkyl, or an amide.

Furthermore, in some embodiments, a composition may further include a co-initiating unit, such as in Formula III:

Formula III

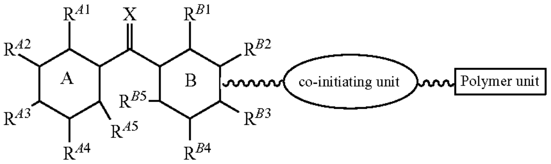

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; the co-initiating unit is an amine, thiol, or any hydrogen atom donor; and the polymer unit is a vinyl, stryl, acryl, or cyclic monomers such as lactones (cyclic esters), epoxides, lactides, lactams, silicon-containing cyclic monomers, cyclic carbonates, or others. A non-limiting example of such a compound is compound 1h:

1h

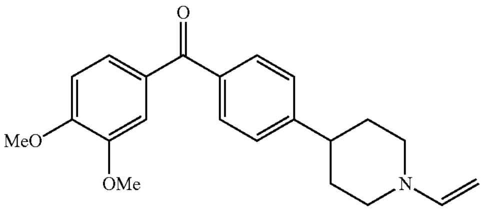

In other embodiments, the composition may include a biomass based aromatic carbonyl compound featuring a coinitiator without the polymer unit, such as in Formula IV:

Formula IV

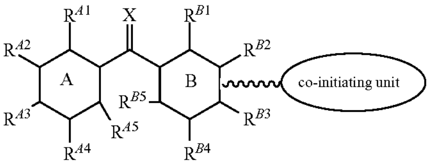

where A or B is a ring derived from biomass; X is O, S, NH, Ge, NC(O)—O—$R^C$, N—O—C(O)$R^C$, or NO—$R^C$, where $R^C$ is alkyl, aryl, or heteroaryl; substituents $R^{A1}$ to $R^{A5}$ and $R^{B1}$ to $R^{B5}$ can be any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes; and the co-initiating unit is an amine, thiol, or any hydrogen donating atom. A non-limiting example of such a compound is compound 1i:

1i

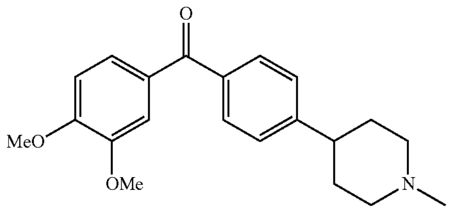

The photoinitiators herein provide an enhanced absorbance profile. In some embodiments, a thousand times less of the photoinitiators described herein can be used to absorb the same amount of light compared to benzophenone (BP), which is a conventional type II photoinitiator. Advantageously, the photoinitiators described herein may be derived from biomass, and used in visible light photopolymerization. Thus, biomass-derived photoinitiating systems can be conveniently utilized for radical polymerization, and can replace conventional UV-curing initiators.

Furthermore, in some embodiments, the photoinitiators described herein may be usable in Type I photoinitiation chemistry, such as photoinitiators having Formula I where X is NC(O)—O—$R^C$ (where $R^C$ is alkyl, aryl, or heteroaryl) or S such that the compound is an imine or thioketone. Non-limiting examples are the compounds having the Formula D:

Formula D

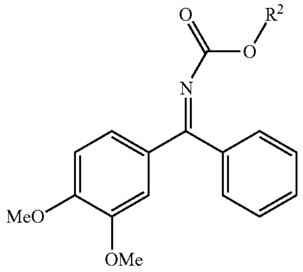

where $R^2$ is alkyl, aryl, or heteroaryl. Another non-limiting example is compound 1j:

1j

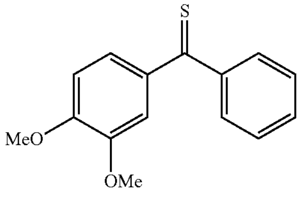

In the examples herein, the biomass-derived photoinitiators 1a-1f are shown to be effective in promoting polymerization under visible light irradiation rather than conventional UV irradiation. The photoinitiators 1a-1f were utilized to build polymers derived from bio sources. These initiators work by a type II mechanism. The performance of these photoinitiators is superior to the conventional systems that are employed for photopolymerization due to their superior photochemical properties. Compared to similar fossil fuel derived systems, the biomass derived photoinitiators herein are used in less amounts (100 to 1000 times less) with typically 2-5 times higher yields for the polymer. They are superior to conventional benzophenone systems, and have the added advantage of decreased loading during curing. This translates to no or very low discoloration or bleaching in the materials that are typically employed in automobile parts, 3D printing, resin curing, dental composites, contact lenses, silicones, epoxies, aircraft parts, composites, and the like.

The compositions and methods described herein can be embodied in the form of a kit or kits. A non-limiting example of such a kit is a kit for conducting a photopolymerization or making a polymer, the kit comprising a monomer and a compound of Formula A in separate containers, where the containers may or may not be present in a combined configuration. Many other kits are possible, such as kits that further include a light source, such as an LED. The kits may further include instructions for using the components of the kit to practice the subject methods. The instructions for practicing the subject methods are generally recorded on a suitable recording medium. For example, the instructions may be present in the kits as a package insert or in the labeling of the container of the kit or components thereof. In other embodiments, the instructions are present as an electronic storage data file present on a suitable computer readable storage medium, such as a flash drive or CD-ROM. In other embodiments, the actual instructions are not present in the kit, but means for obtaining the instructions from a remote source, such as via the internet, are provided. An example of this embodiment is a kit that includes a web address where the instructions can be viewed and/or from which the instructions can be downloaded. As with the instructions, this means for obtaining the instructions is recorded on a suitable substrate.

EXAMPLES

In these examples, biomass-derived photoinitiators are shown to be effective in promoting polymerization under visible light irradiation rather than conventional UV irradiation. The photoinitiators were utilized to build polymers derived from bio-sources.

The proliferation of smart materials over the past decade is in part due to their versatility in bridging the gap between performance and practicality. In addition, their inherent physical properties allow for expanding their use. To sustain such developments, fostering development beyond the conventional fossil fuel-based sources has become a necessity in part due to the stress put on a dwindling resource. Biomass provides a clear and sustainable alternative for developing systems by utilizing natural chemical functionalities and fine-tuning the properties of molecules to address specific needs. These examples describe the development of photoinitiators based on biomass that have superior properties when compared to some of the conventional fossil fuel-based systems. Photopolymerization has proven to be a viable method of synthesizing various polymers including smart materials. To make use of the functionalities provided by nature and tailor them to respond to light, it is necessary to modify the system so that an appropriate chromophore is generated for efficient light absorption. In this regard, bio-based photoinitiators may play a key role in the photo-polymerization process.

Photoinitiators can be broadly classified as type I or type II photoinitiators. Type II based systems are interesting due to the bimolecular nature of generating the reactive radicals. For example, benzophenone (BP), a well-established photoinitiator, promotes polymerization by type II chemistry in the presence of co-initiators/H-donors. The mechanistic pathway involved for photochemical polymerization mediated by benzophenone occurs from a triplet n7r* excited state that generates ketyl radical of the photoinitiator and radical of the co-initiator that serves as hydrogen atom donor. While benzophenone based type II systems are very reliable and are widely used, benzophenone does suffer from a few short comings such as: a) the need for UV light to initiate the reaction; and b) requiring high weight % loading of the photo-initiator due to the low absorptivity of benzophenone that features a forbidden nπ* transition as the lowest transition. To develop biomass based photoinitiators with superior photochemical and photophysical properties as substitutes to fossil fuel derived photo-initiating systems such as benzophenone, one has to overcome the above limitations as well as a fundamental bottle neck presented by biomass derived systems, i.e., tailoring the functionalities presented by nature to fine-tune them to have excellent photochemical properties. Having this aspect in mind, biomass-based photoinitiating systems were developed based on type II photochemistry by utilizing veratraldehyde 9 (Scheme 1, FIG. 2).

Veratraldehyde 9, a well-known flavouring with woody fragrances, was modified by simple and well-established chemical transformations for the developing photo-initiators 1a-1f. The newly developed bio-mass derived photoinitiators 1a-1f featuring benzophenone type chromophores with tailored functional groups for handling photochemical properties were evaluated for their photo-polymerization effeciencies of acrylates 3 and furfural derived acrylates 5 and 7 (Scheme 2, FIG. 3). To showcase the efficiency of the bio-based photoinitiators, their photochemical and polymerization properties were compared with benzophenone.

Figure 3:
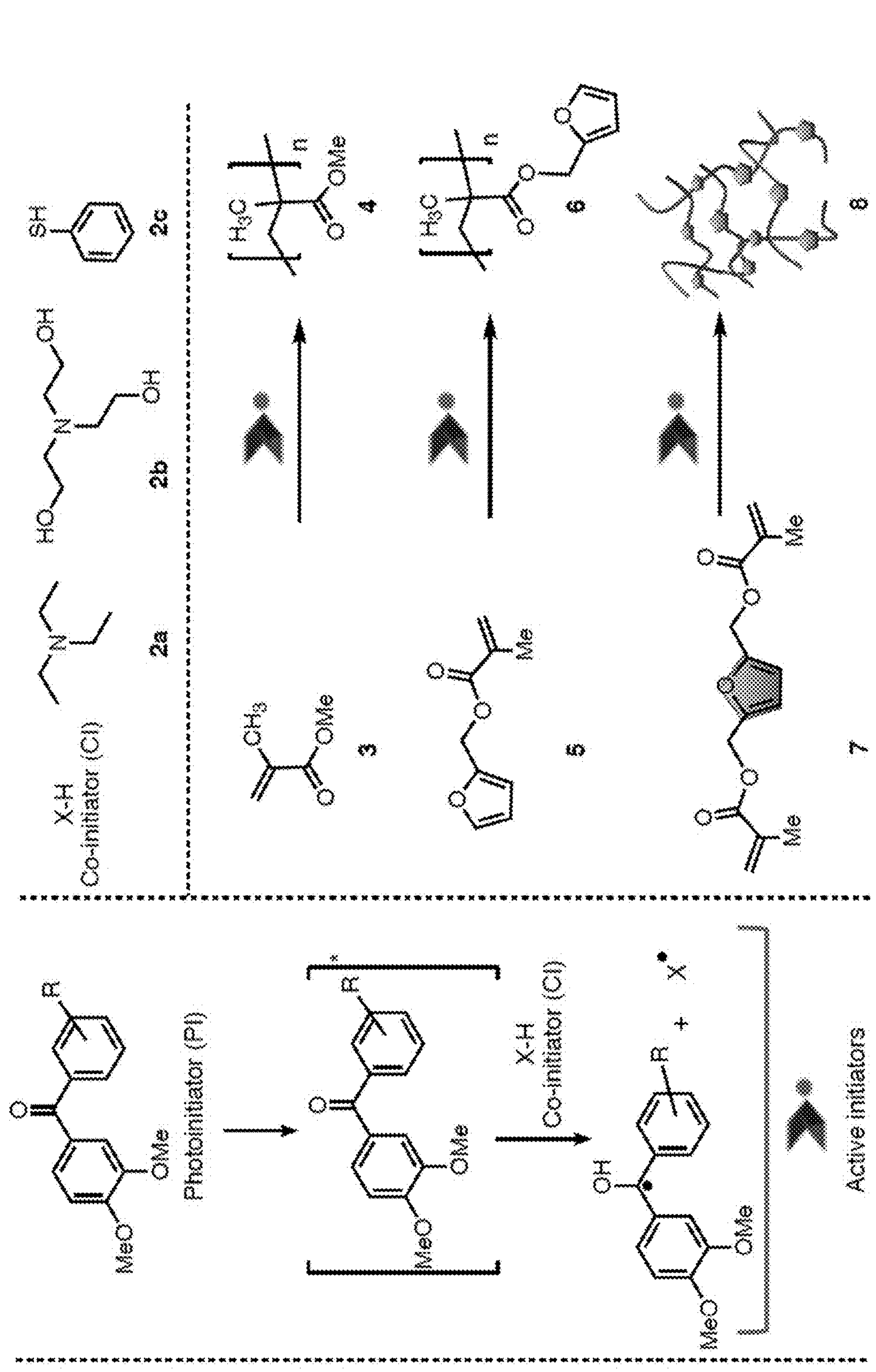
FIG. 3: Scheme 2, depicting biomass derived materials using biomass derived photoinitiators.

Biomass derived photoinitiators (PI) were synthesized from veratraldehyde in two simple steps (Scheme 2, FIG. 3). A Grignard reagent of varying substitution was employed followed by benzylic oxidation in the presence of $MnO_2$, affording biomass derived photoinitiators 1a-1f that were characterized by $^1$H NMR and $^{13}$C NMR spectroscopy. Differential substitution in the photo-initiators 1a-1f allows for systematic investigations of their photochemical and photophysical properties.

Figure 4A:
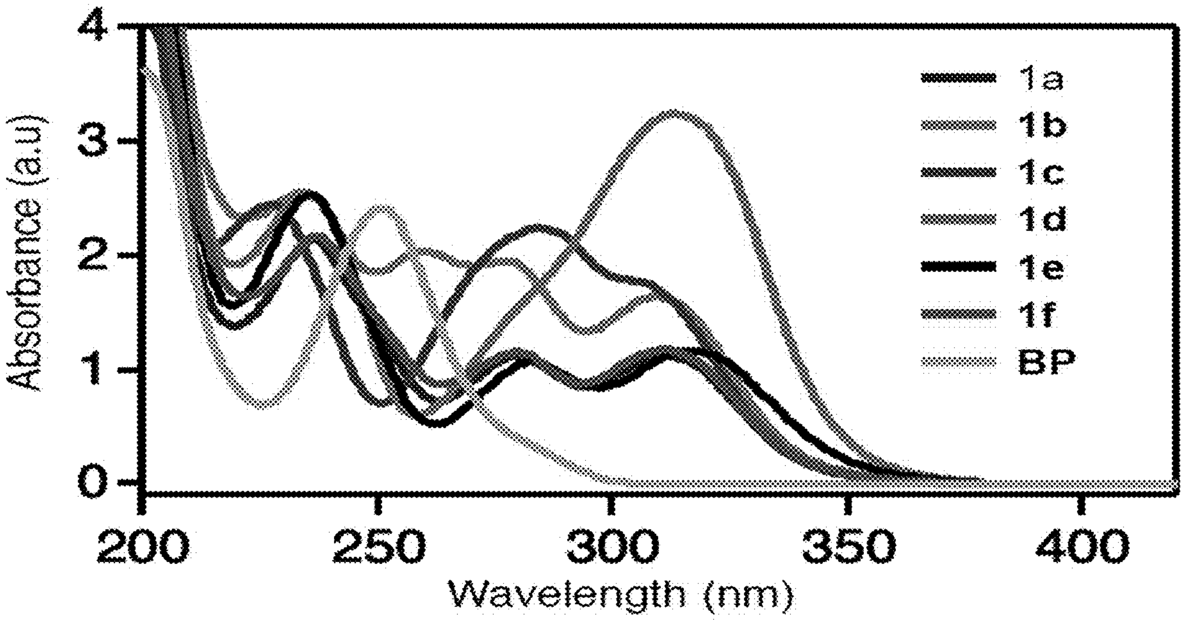
FIGS. 4A-4B: Absorption spectra of photoinitiators 1a-1f and benzophonenone (BP) for 150 μM in MeCN (FIG. 4A), and absorption spectra of photoinitiators 1a-1f and BP in MeCN with matching optical density at ~390 nm (FIG. 4B). The concentrations employed to reach OD of ~0.25 are provided in the right side plot and in Table 3.

Absorbance spectra of the newly synthesized veratraldehyde derived photoinitiators 1a-1f displayed a bathochromic shift in absorbance with respect to structurally similar benzophenone (BP) (FIG. 4A). The absorption spectra of photoinitiators with the same concentration, i.e.,150 μM in $CH_3CN$ (FIG. 4A) and ~4 mM in $CH_3CN$, were obtained. From the spectra in FIG. 4A, it is understood that on changing the functional group of H to electron donating groups methyl, methoxy, and thiomethyl (1b through 1d), there is a stronger absorption near the UV spectral region when compared to electron withdrawing groups trifluoromethyl 1e and fluoro derivative 1f. Upon a close look into the spectra, thiomethyl derivative 1d at 150 μM concentration has stronger absorbance with OD ~3.2 at 313 nm. Based on the UV-Vis studies at low concentrations, photopolymerization of methylmethacrylate monomer 3 was performed with concentration of photoinitators and co-initiators at 5 mM in $CH_3CN$. Table 1 details the initial screening of co-initiators 2a, 2b, and 2c, and photopolymerization was carried out at ambient conditions using purple LED light (1.5 mW/cm$^2$, Ee=Flux density (mW/cm$^2$) measured by Newport/spectra physics 407A Portable Laser Power Meter by keeping the a distance of ~2 cm from the light source). All the samples were saturated with $N_2$ prior to photopolymerization to remove dissolved oxygen and avoid quenching of excited states by oxygen Amines (2a-2b), thiophenol 2c, and isopropyl alcohol 2d (both as solvent and H-atom donor) were evaluated as co-initiators (Scheme 2, FIG. 3). Photopolymerization of methylmethacrylate 3 (3.12 M) initiated through excitation of 1a (5 mM) in the presence of triethanolamine 2b (5 mM) was found to be relatively efficient with a % weight conversion ~10.6% and polydispersity index PDI (Mw/Mn) of ~1.4 (Table 1, entry 2).

Figure 4B:
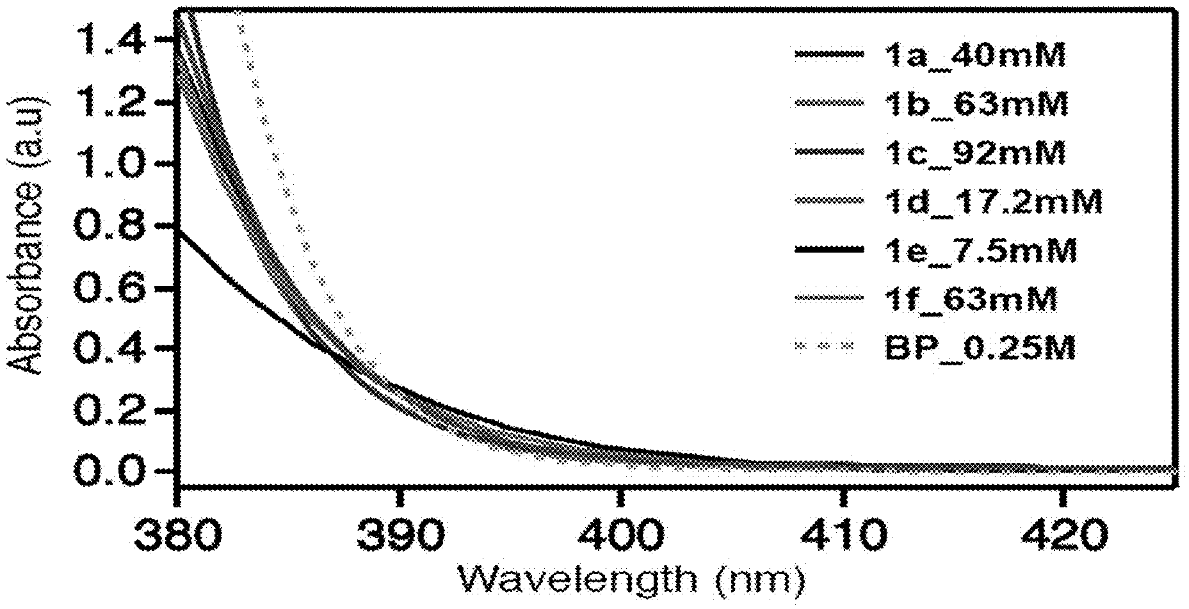
Figure 5:
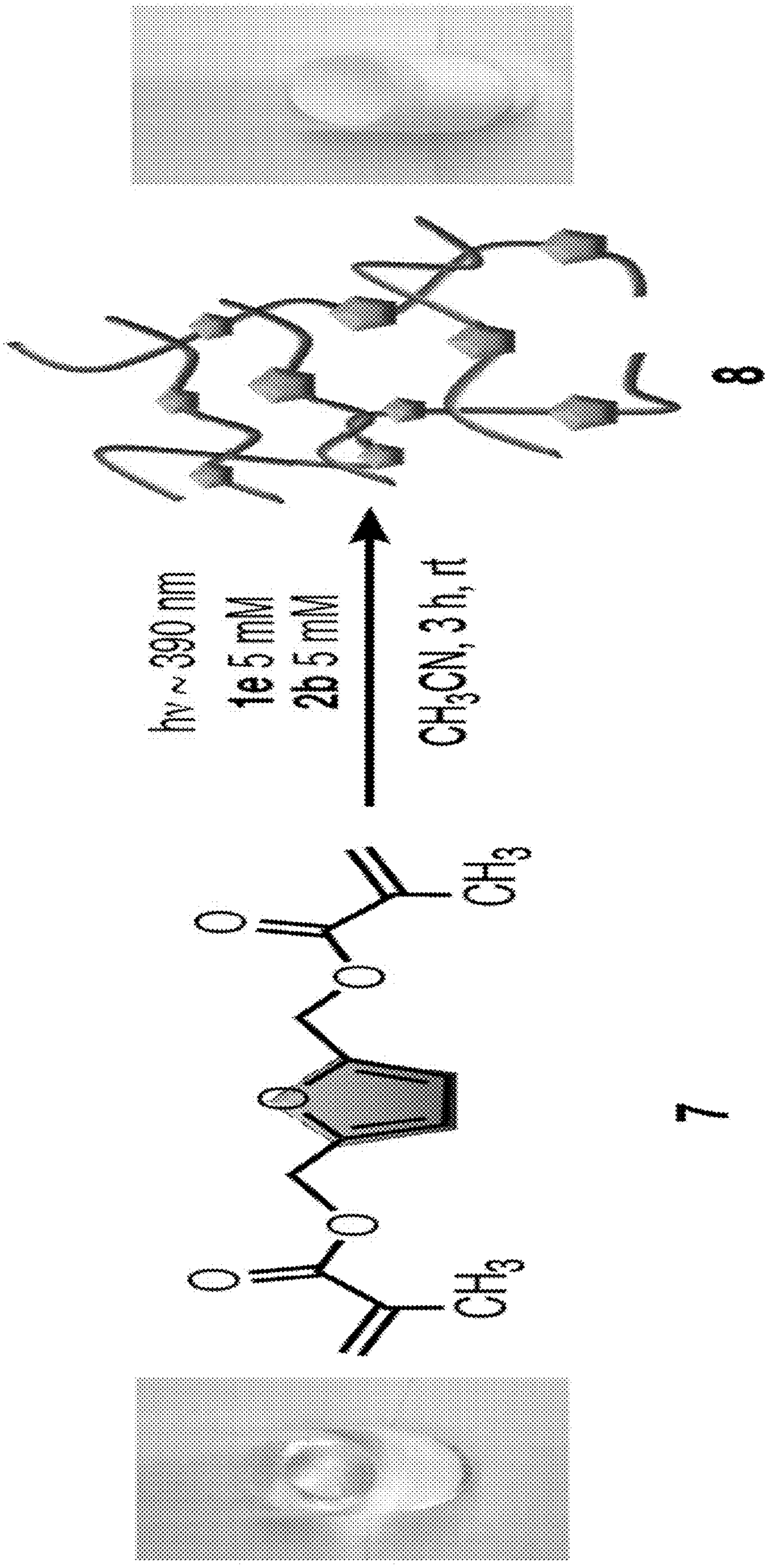
FIG. 5: Photopolymerization of 2,5-bis(hydroxymethyl) furan dimethacrylate (FDMA) 7 to crosslinked polymer 8.

Under similar conditions, amine co-initiator 2a gave a conversion of 4.2% (Table 1, entry 1). Non-amine co-initiator thiophenol gave a conversion of 7.4% (Table 1, entry 3). Based on this initial screening, the photopolymerization efficiency of veratraldehyde based photoinitators 1b-1f with monomer 3 and co-initiator 2b was evaluated. Changing from 1a to electron donating p-methyl derivative 1b and p-methoxyl 1c resulted in a decrease in conversion of 7.6% and 6.6% m respectively (Table 1, entries 4 and 5). The placement of a p-thiomethyl substituent (**1*d*) not only increased the absorptivity in the visible region but also gave increased conversion of 15.6% compared to 1a (compare Table 1, entries 2 and 6). Photoinitiators featuring electron withdrawing p-trifluoromethyl 1e and p-fluoro substituent if gave conversions of 16.8% 10.9%, respectively (PDI ~1.5; Table 1, entries 7 and 8). As p-trifluoromethyl substituted biomass derived photoinitiator 1e showed the highest efficiency for the tested photoinitiators, photopolymerization of biomass derived furfural methacrylate (FMA) 5 and 2,5-bis (hydroxymethyl)furan dimethacrylate (FDMA) polymer 8 was carried out. Photopolymerization of monomer 5 gave polymer 6 with 21% conversion with less control on PDI 2.4 and dimethacrylate derivative FDMA 7 resulted in formation of semi-gelatinous crosslinked polymer 8 with % weight conversion ~78% (FIG. 5). Under similar conditions, traditional benzophenone photoinitiator gave a conversion of 2.7% (Table 1, entry 9). To further understand, the photopolymerization efficiency photoinitiators 1a-1f comparative studies were carried out with matching optical density. Concentrations of photoinitiator 1a-1f were varied to match the optical density of ~0.2 at ~390 nm (Table 2; FIG. 4**B). The molar absorption coefficient e ($M^{-1}$ $cm^{-1}$) for photoinitiators at 390 nm indicated that the lowest excited state is likely of np* character. The higher molar absorption coefficient of trifluoromethyl derivative 1e (e390=38.8 $M^{-1}$ $cm^{-1}$) compared to benzophenone BP (e390=1.0 $M^{-1}$ $cm^{-1}$) allowed for 1e to be employed at 7 mM (in $CH_3CN$), while a 0.2 M was utilized for BP, i.e., a concertation ~35 times less for 1e than that of BP (entries 5 and 7).

TABLE 1

Biomass derived photoinitiators for methacrylate polymerization[a]

| Entry | PI | CI | Monomer | % Conversation [b] | Mn | Mw | PDI |
|---|---|---|---|---|---|---|---|
| 1 | 1a | 2a | 3 | 4.2 | 70,252 | 135,409 | 1.9 |
| 2 | | 2b | 3 | 10.6 | 33,383 | 47,150 | 1.4 |
| 3 | | 2c | 3 | 7.4 | 20,054 | 27.568 | 1.4 |
| 4 | 1b | 2b | 3 | 7.6 | 41,520 | 68,026 | 1.6 |

TABLE 1-continued

Biomass derived photoinitiators for methacrylate polymerization[a]

| Entry | PI | CI | Monomer | % Conversation [b] | Mn | Mw | PDI |
|---|---|---|---|---|---|---|---|
| 5 | 1c | 2b | 3 | 6.6 | 61,862 | 115,867 | 1.8 |
| 6 | 1d | 2b | 3 | 15.6 | 23,869 | 36,707 | 1.5 |
| 7 | 1e | 2b | 3 | 10.9 | 25,562 | 39,114 | 1.5 |
| 8 | 1f | 2b | 3 | 10.9 | 36,328 | 55,283 | 1.5 |
| 9 | BP | 2b | 3 | 2.7 | 105,614 | 195,602 | 1.8 |
| 10 | 1e | 2b | 5 | 21 | 62,457 | 152,858 | 2.4 |
| 11 | 1e | 2b | 7 | 78 | — | — | —[c] |
| 12 | 1e | 2d | 3 | 24.7 | 34,748 | 98,965 | 2.8 |

[a]M = Monomer; PI = Photoinitiator; CI = co-initiator. [PI] = 5 mM, [CI] = 5 mM, [Monomer] = 3.12M sovent = $CH_3CN$. Photopholymerization were carried out with a purple LED strip illumination with a flux density of 1.5 mW/cm$^2$. Ee = Flux density (mW/cm$^2$) measured by Newport/spectra physics 407A Portable Laser Power Meter by keeping the sample at a distance of ~2 cm from the light source. Irradiation was done for 3 h.

[b] Conversions determined by gravimetric analysis and carry an error of 3%. The values reported are an average of three runs.

[c]Crossed linked polymer.

Polymerization of monomer 3 in $CH_3CN$ with 2b as co-initiator was investigated with various photoinitiators 1a-1f with optical density of ~0.2, the yield as ascertained by gravimetric analysis under purple LED illumination varied from 20-37% (Table 2, entries 1-9). Notably, the concentration of 1e employed for the study is 8 times less than that of 1f and ~35 times lesser than benzophenone (BP) for comparable yields (Table 2, entry 9).

TABLE 2

Evaluation of efficiency of photopolymerization of methylmethacrylate of same optical density[a]

| Entry | PI | [1] mM | ε(M$^{-1}$ cm$^{-2}$) | % Conversion [d] | Mn | Mw | PDI |
|---|---|---|---|---|---|---|---|
| 1 | 1a | 40 | 6.5 | 17.5 | 20,738 | 33,730 | 1.6 |
| 2 | 1b | 46 | 5.6 | 14.3 | 34,425 | 50,502 | 1.4 |
| 3 | 1c | 92 | 2.3 | 19.7 | 22,246 | 41,014 | 1.8 |
| 4 | 1d | 14 | 17.8 | 30.8 | 21,676 | 36,430 | 1.6 |
| 5 | 1e | 7 | 88.8 | 27.6 | 29,113 | 44,676 | 1.5 |
| 6 | 1ec | 7 | 38.8 | 17.0 | 44,655 | 63,836 | 1.5 |
| 7 | 1ed | 7 | 38.8 | 37.0 | 18,525 | 30,619 | 1.6 |
| 3 | 1f | 57 | 4.6 | 25.7 | 25,448 | 40,201 | 1.5 |
| 9 | BP | 247 | 1.0 | 19.2 | 21,509 | 39,761 | 1.8 |

[a]M = Monomer; CI = co-initiator. [CI] = 2b (Triethanolamine) 7 mM. [Monomer] = 3.12M, solvent = $CH_3CN$.

[b]2b = 0.7 mM and c2b = 15 mM. Photopolymerization were carrier out with a purple LED strip illumination with a flux density of 1.5 mW/cm$^2$. Irradiation was done for 3 h. Ee = Flux density (mW/cm$^2$) measured by Newport/spectra physics 407A Portable Laser Power Meter by keeping sample at a distance of ~2 cm from the light source.

[d]Conversions determined by gravimetric analysis and carry an error of 3%. The values reported are an average of three runs.

Figure 6:
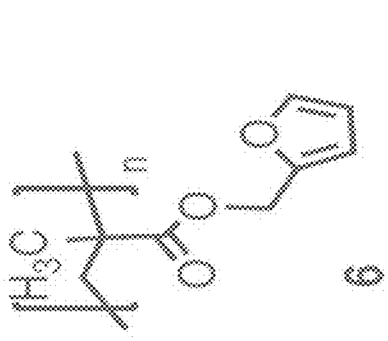
FIG. 6: Thermogravimetric analysis of 6 and 8.
Figure 6:
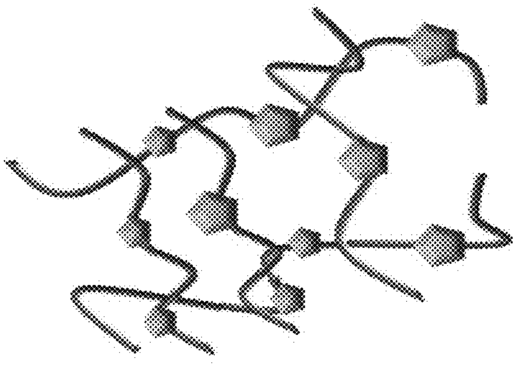
Figure 6:
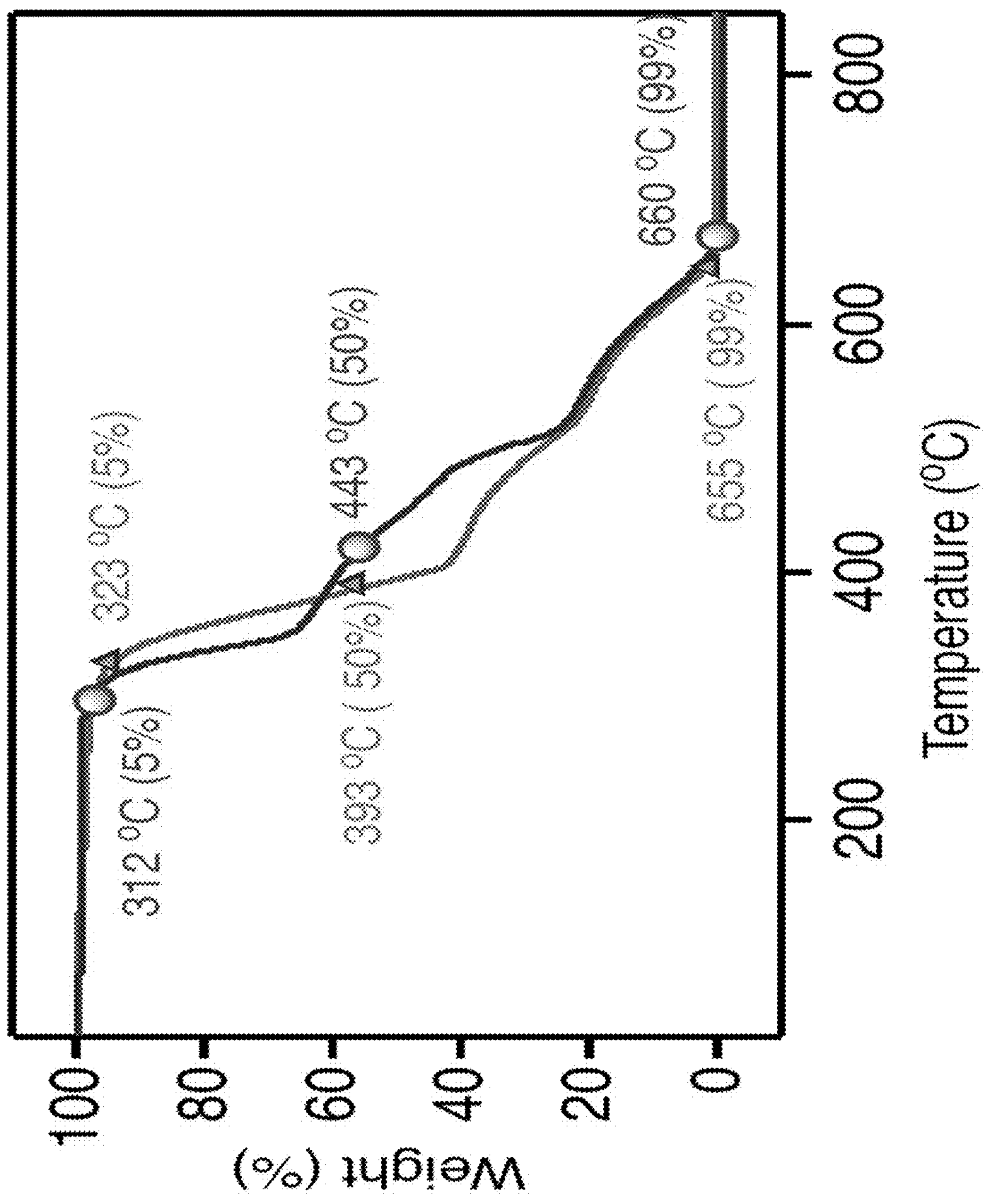

Thermal properties for the biomass derived furfural methacrylate polymer 6 and 2,5-bis(hydroxymethyl)furan dimethacrylate (FDMA) polymer 8 with a furan core as linker were studied by Thermogravimetric analysis (TGA). Thermal decomposition temperature $T_d$ (temperature at which 5% weight loss in TGA cure) was found to be 323° C. for poly (furfuryl methacrylate) (PFMA) and ~312° C. for crosslinked polymer poly (furfuryl dimethacrylate) (PFDMA) 8 (FIG. 6). A 50% weight loss at ~443° C. for 8 shows that it has relatively high thermal stability when compared to 6 (50% loss at ~393° C.). Both 6 and 8 were completely decomposed at temperature above ~660° C.

Figure 39:
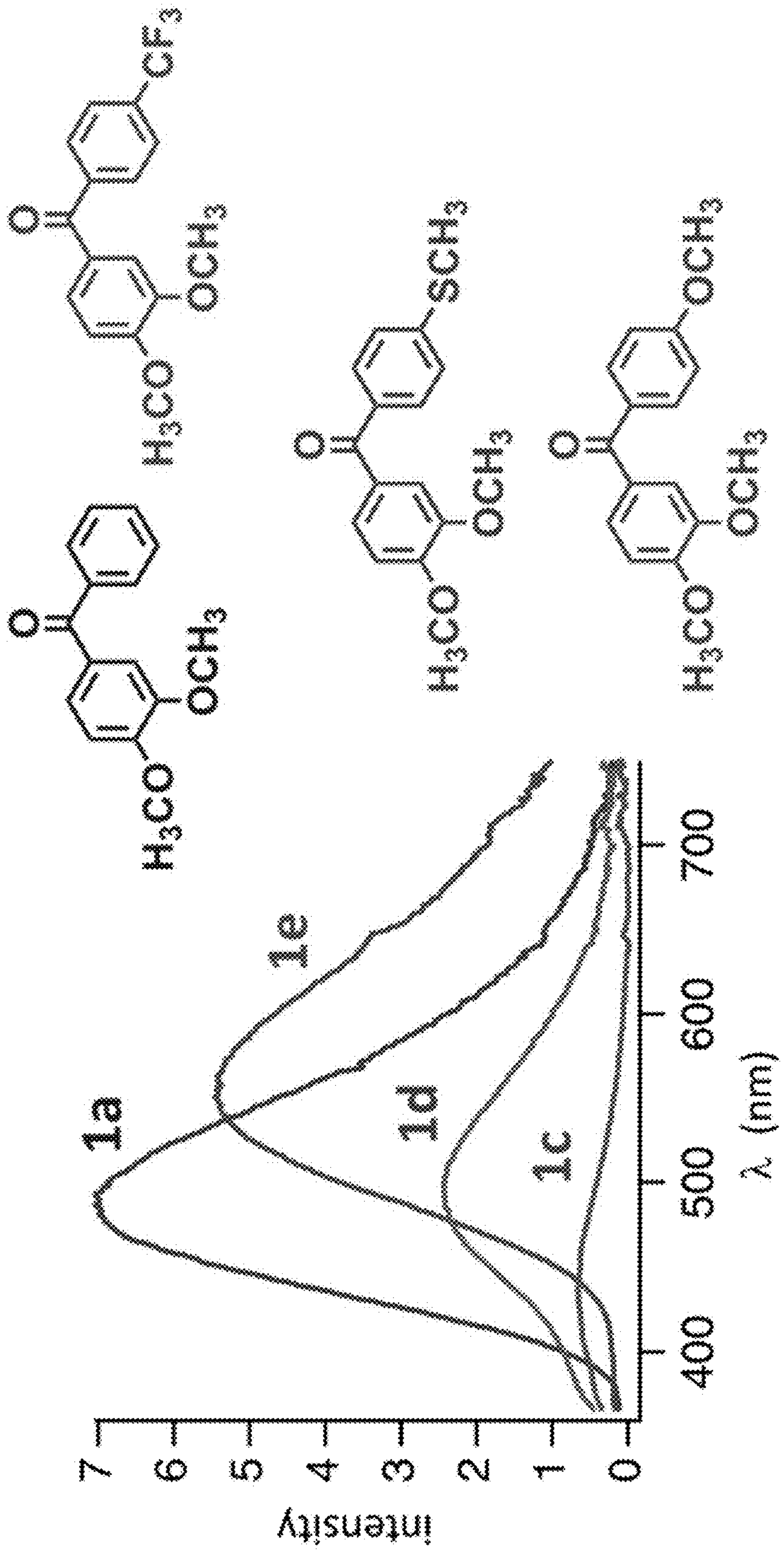
FIG. 39: Fluorescence spectra in acetonitrile at room temperature ($\lambda_{ex}$=322 nm).
Figure 40:
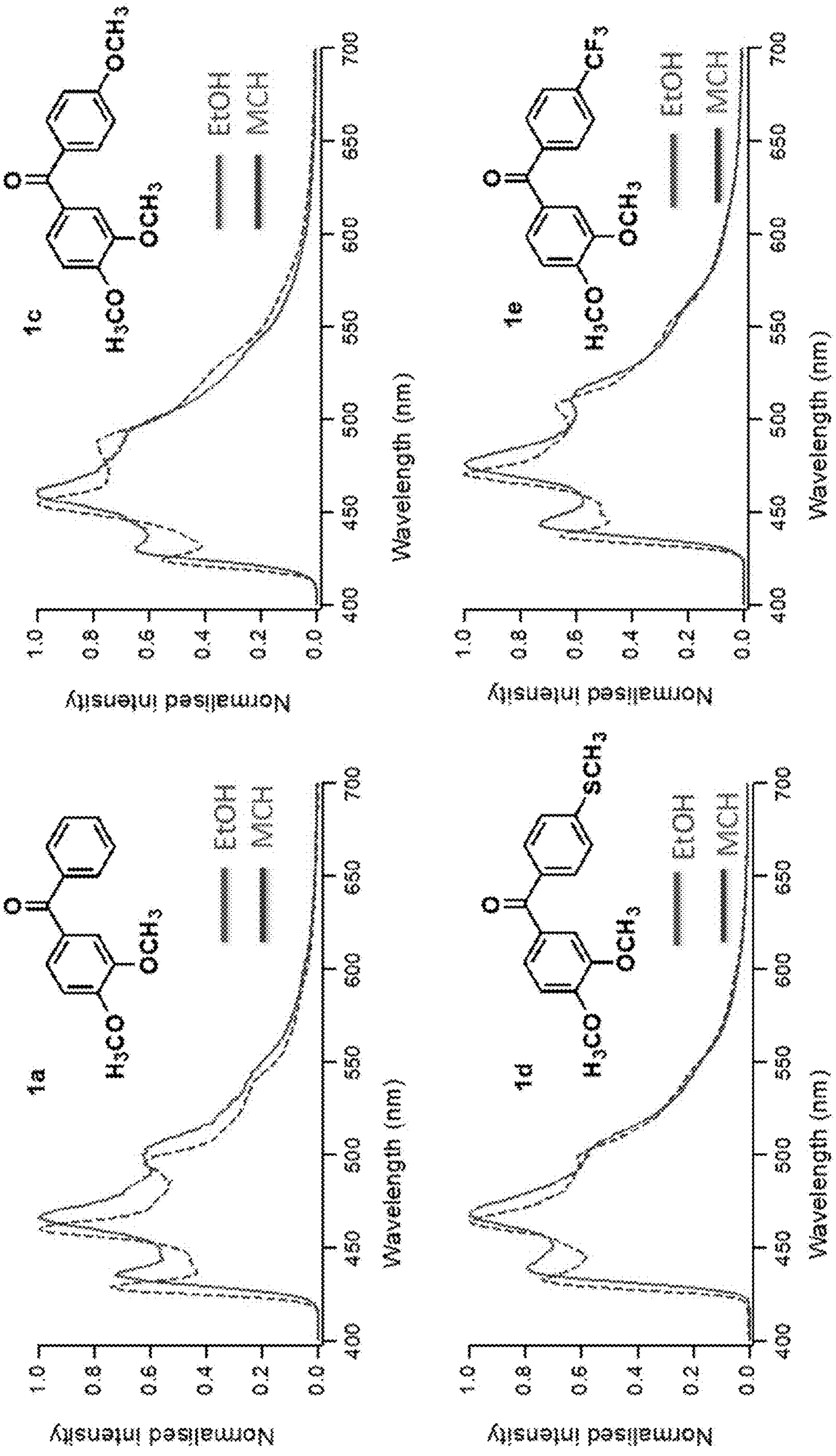
FIG. 40: Phosphorescence spectra of 1a, 1c, 1d, and 1e. Normalized phosphorescence spectra in EtOH (red) and MCH (blue) glass at 77 K recorded 10 to 30 ms after pulsed excitation at $\lambda_{ex}$=320 nm (1a, 1d, 1e in EtOH, and 1e in MCH) or at $\lambda_{ex}$=310 nm (1c EtOH, and 1a, 1c, 1d in MCH).

To evaluate the excited state processes involved in radical generation and their kinetics, photophysical studies were performed on four of the biomass derived photoinitiators, 1a, 1_c_, 1d, and 1_e_. After photoexcitation, only negligible fluorescence was observed ($\Phi_f$<0.002; see Table 4 and FIG. 39), indicating nearly quantitative intersystem crossing of singlet excited states into triplet states. To investigate the triplet state properties, phosphorescence experiments were performed in frozen matrix at 77 K. FIG. 40 shows the phosphorescence spectra of 1_a_, 1c, 1d, and 1e in a polar (ethanol) and non-polar (methylcyclohexane) glass at 77 K. The spectra reveal that with increasing solvent polarity a bathochromic shift of the phosphorescence peaks is observed. This solvent polarity dependence together with the long phosphorescence lifetimes (Table 4 and FIG. 40) indicate that the energetically lowest triplet state is of ππ* configuration. Triplet states with nπ* configuration, such as benzophenone, show a hypsochromic shift with increasing solvent polarity and have shorter phosphorescence lifetimes. The energies of the trplet states were determined from the high-energy peaks of the phosphorescence spectra (FIG. 40) and are listed in Table 4. The triplet state energies of 1a, 1c, 1d, and 1e are in the 270-280 kJ/mol range, which are slightly lower than for benzophenone (278-289 kJ/mol).

TABLE 4

Photophysical and photochemical properites of 1a, 1c, 1d, and 1e

| | 1a | 1c | 1d | 1e |
|---|---|---|---|---|
| $\Phi_f$[a] | 0.0013 | 0.0001 | 0.0005 | 0.0013 |
| $\tau_T$ (μs) [b] | 18 | 36 | 22 | 42 |
| $\tau_p^{77K}$ EtOH (ms) [c] | 150 | 110 | 45 | 145 |
| $\tau_p^{77K}$ MCH (ms) [c] | 78 | 61 | 28 | 86 |
| $E_{EtOH}^T$ (kJ/mol) [d] | 275 | 278 | 275 | 270 |
| $E_{EtOH}^T$ (kJ/mol) [d] | 279 | 282 | 276 | 274 |
| $k_q^{2b}$ ($10^8$ M$^{-1}$ s$^{-1}$) [e] | 3.0 ± 0.1 | 2.3 ± 0.1 | 3.6 ± 0.1 | 6.7 ± 0.1 |
| $k_q^{O2}$ ($10^9$ M$^{-1}$ s$^{-1}$) [f] | 6.3 ± 0.2 | 5.9 ± 0.2 | 5.9 ± 0.2 | 5.1 ± 0.2 |

[a] Fluorescence quantum yield in acetonitrile at room temperature.

[b] Triplet lifetime in acetonitrile at room temperature determined by laser flash photolysis.

[c] Phosphorescence lifetime at 77K determined by multi-channel scaling.

[d] Tripplet energy determined form the high-energy peak of the phosphorescence spectra at 77K.

[e] Bimolecular quenching rate constant of triplet state quenching by 2b in acetonitrile at room temperature.

[f] Bimolecular quenching rate constant of triplet state quenching by molecular oxygen in acetonitrile at room temperature.

Figure 38:
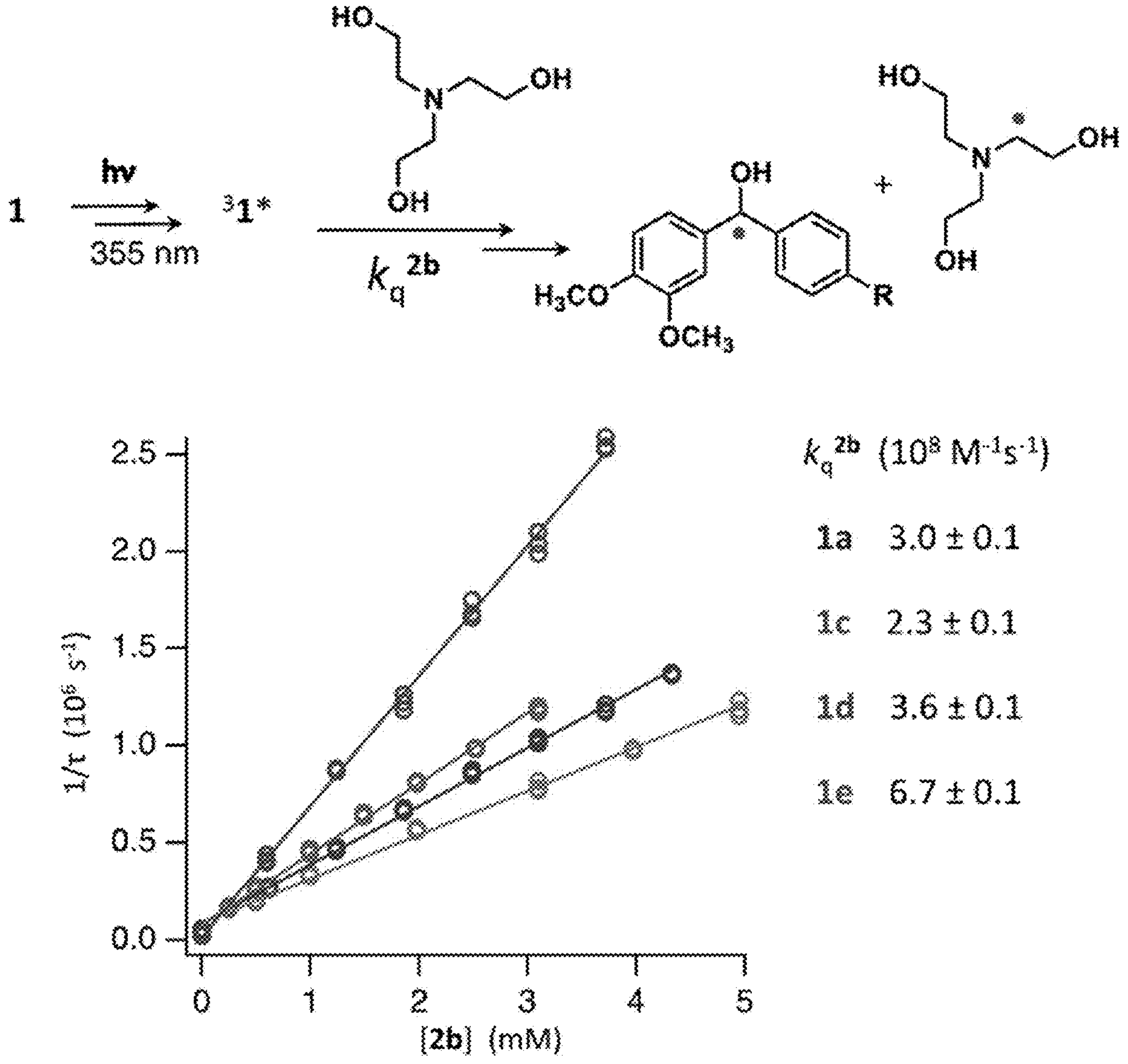
FIG. 38: Top: Reaction mechanism for generating initiator radicals. Bottom: Determination of the bimolecular quenching rate constants $k_q^{2b}$ from the plot of the inverse triplet lifetimes of 1a, 1c, 1d, and 1e measured by laser flash photolysis and monitored at 650 nm (1_a_), 620 nm (1c), 700 nm (1d), and 740 nm (1e) vs. varying concentrations of 2b in acetonitrile.
Figure 41:
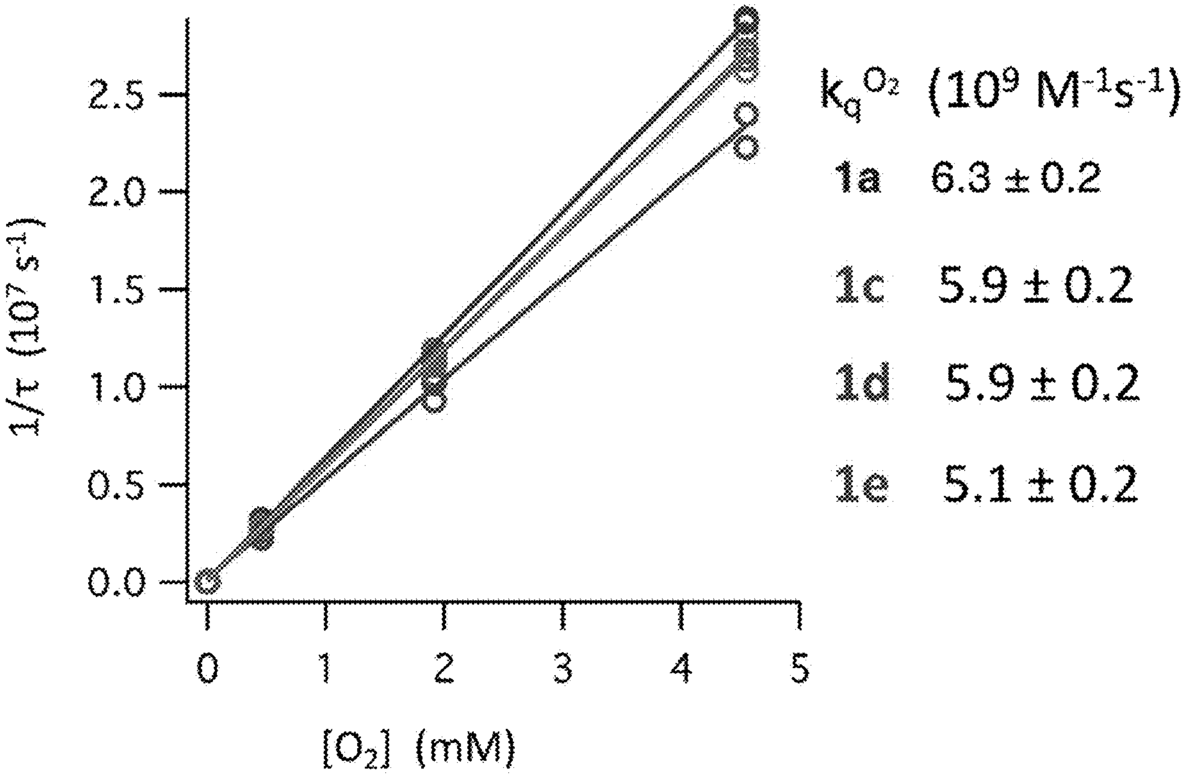
FIG. 41: Determination of the bimolecular oxygen quenching rate constants $k_q^{O2}$ from the plot of the inverse triplet lifetimes of 1a, 1c, 1d, and 1e measured by laser flash photolysis and monitored at 650 nm (1a), 620 nm (1c), 700 nm (1d), and 740 nm (1e) vs. varying concentrations of dissolved oxygen in acetonitrile.

To investigate the trplet state properties at room temperature, transient absorption measurements were performed using a pulsed laser for excitation ($\lambda_{ex}$=355 nm, 5 ns pulse width). FIGS. 37A-37D show the transient absorption spectra of 1a, 1c, 1d, and 1e, which were assigned to triplet-triplet absorptions. The triplet states decayed with lifetimes between 18 to 42 μs under the experimental conditions and were quenched by molecular oxygen with rate constants close to the diffusion limit (Table 4, FIG. 41). The critical stpe in generating radicals that can initate free radical polymerization is the reaction of triplet states of the photoinitiator with the co-initiator (e.g., tertiary amine) The bimolecular quenching rate constants of triplet state quenching of 1a, 1c, 1d, and 1e by tertiary amine 2b were determined by laser flash photolysis by pseudo-first order treatment for the triplet decay traces of the photoinitiators at varying concentrations of 2b. The bimolecular quenching rate constants $k_g^{2b}$ were calculated from the slope of the inverse triplet lifetimes vs. the 2b concentrations (FIG. 38). The high-rate constants (3-7×10$^8$ M$^-$s$^{-1}$) ensure efficient initiator radical generation. The rate constants ($k_q^{2b}$) correlate with the gravimentrically determined conversions of MMA into polymer (Table 1). The highest rate constant was observed for 1e ($k_g^{2b}$=6.7×10$^8$ M$^{-1}$s$^{-1}$) which also showed the highest conversion (16.8%).

These examples showcase that biomass derived systems can be conveniently utilized as visible light photoinitiators. The performance of these photoinitiators 1a-1f is superior to the conventional benzophenone photoinitiator systems that are employed for photopolymerization due to their photochemical properties.

General Methods

All commercially obtained reagents/solvents were used as received; chemicals were purchased from Alfa Aesar®, Sigma-Aldrich®, Acros organics®, TCI America®, and Oakwood® Products, and were used as received without further purification. Spectrophotometric grade solvents (e.g., acetonitrile, ethanol) were purchased from Sigma-Aldrich® and used without further purification for emission measurements. Unless stated otherwise, reactions were conducted in oven-dried glassware under nitrogen atmosphere. $^1$H-NMR and $^{13}$C-NMR spectra were recorded on Bruker 400 MHz (100 MHz for $^{13}$C) and on 500 MHz (125 MHz for $^{13}$C) spectrometers. Data from the $^1$H-NMR spectroscopy are reported as chemical shift (δ ppm) with the corresponding integration values. Coupling constants (J) are reported in hertz (Hz). Standard abbreviations indicating multiplicity were used as follows: s (singlet), b (broad), d (doublet), t (triplet), q (quartet), m (multiplet), and virt (virtual). Data for $^{13}$C NMR spectra are reported in terms of chemical shift (δ ppm). Infrared spectra for the compounds were recorded by using Thermo Scientific™ Nicolet™ iS5 FTIR spectrometer and OMNIC software. Thermal stabilities of polymer samples were measured on TGA-50 (TA instruments, Inc., New Castle, Del.). PXRD measurements were carried out with a Bruker D8 Advance PXRD. High-resolution mass spectrometry (HRMS) was performed using a Waters Synapt high-definition mass spectrometer with a nano-electrospray ionization (ESI) source (Waters, Milford, Mass.).

UV-Vis spectra were recorded on Cary 300 UV-Vis spectrometer using UV quality fluorimeter cells (with range until 190 nm) purchased from Luzchem. When necessary, the compounds were purified by combiflash equipped with dual wavelength UV-Vis absorbance detector (Teledyne ISCO) using hexanes: ethyl acetate as the mobile phase and RedisepR cartridge filled with silica (Teledyne ISCO) as stationary phase. In some cases, compounds were purified by column chromatography on silica gel (Sorbent TechnologiesR, silica gel standard grade: porosity 60 A, particle size: 230×400 mesh, surface area: 500-600 m$^2$/g, bulk density: 0.4 g/mL, pH range: 6.5-7.5). Unless indicated, the Retention Factor ($R_f$) values were recorded using a 5-50% hexanes:ethyl acetate as mobile phase and on Sorbent TechnologiesR, silica Gel TLC plates (200 mm thickness w/UV254).

Photophysical Methods

Spectrophotometric solvents (Sigma-Aldrich®) were used whenever necessary unless or otherwise mentioned. UV quality fluorimeter cells (with range until 190 nm) were purchased from Luzchem®. Absorbance measurements were performed using a Cary UV-Vis spectrophotometer. Emission spectra were recorded on a Horiba ScientificR Fluorolog 3 spectrometer (FL3-22) equipped with double-grating monochromators, dual lamp housing containing a 450-watt CW xenon lamp and a UV xenon flash lamp (FL-1040), Fluorohub/MCA/MCS electronics and R928 PMT detector. Emission and excitation spectra were corrected in all the cases for source intensity (lamp and grating) and emission spectral response (detector and grating) by standard instrument correction provided in the instrument software. Fluorescence (steady state) and phosphorescence (77 K) emission spectra were processed by FluorEssenceR software. Phosphorescence lifetime measurements were performed using DAS6R V6.4 software. The goodness-of-fit was assessed by minimizing the reduced chi squared function and further judged by the symmetrical distribution of the residuals. Laser flash photolysis experiments employed the pulses from a Spectra Physics GCR-150-30 Nd:YAG laser (355 nm, ca. 5 mJ/pulse, 7 ns pulse length, or 266 nm, ca 5 mJ/pulse, 5 ns pulse length) and a computer-controlled system.

Gel Permeation Chromatography (GPC) Analysis for Polymers

Polymer sample analysis were performed on EcoSEC GPC System (HLC-8320) equipped with a dual flow refractive index detector (RI) detector. Separation of injections occurred over a column bank consisting of two 67.8 mm ID×30 cm, 5 μm particle size TSKgelR multiporeH xL (exclusion limit 6×104 g/mol) and one 6 mm ID×15 cm, 4 μm particle size TSKgel SuperH-RC (exclusion limit 5×10$^5$ g/mol) columns (Tosoh Bioscience LLC). Tetrahydrofuran (THF) (HPLC grade, EMD OmnisolvR) was used as mobile phase for sample preparation. The GPC analysis was performed at a flow rate of 1 mL/min with the column oven were maintained at 40° C. Polystyrene kits with PStQuick C (Lot No: PSQ-D02C) and PStQuick C (Lot No: PSQ-C04C) were utilized for calibration. All the molecular weight values (Mw, Mn, and PDI) results are calculated based on a polystyrene calibration curve.

Concentration of polymer sample for GPC analysis: 1 mg/ml in THF prior to injections samples were equilibrated overnight and filtered through 25 mm, 0.2 mm PTFE membrane filter.

Chemical Structures of Photoinitiators, Co-Initiators, and Polymers

Figure 7:
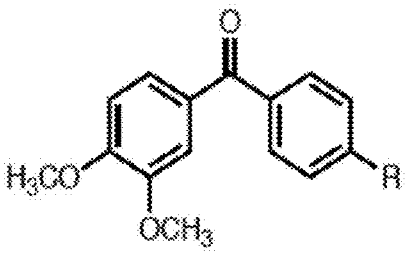
FIG. 7: Chemical structures of biomass derived benzophenone derivatives, monomers, and corresponding polymer products.
Figure 7:
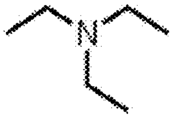
Figure 7:
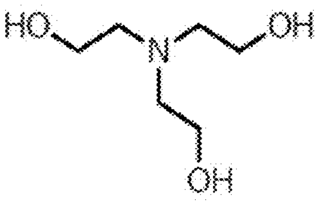
Figure 7:
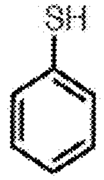
Figure 7:
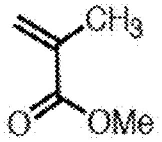
Figure 7:
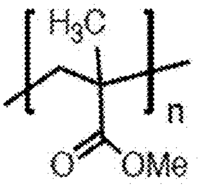
Figure 7:
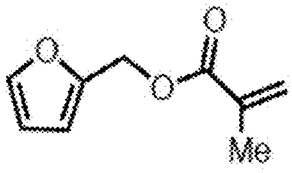
Figure 7:
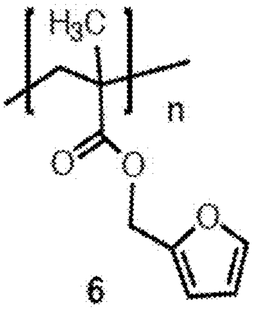
Figure 7:
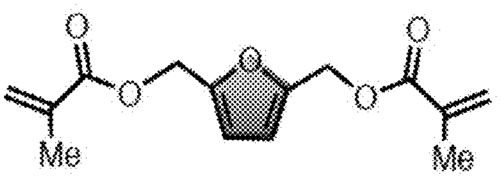
Figure 7:
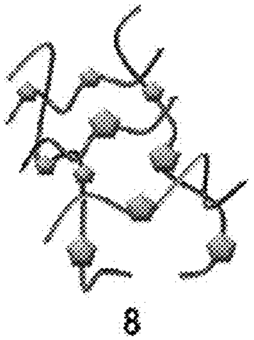
Figure 7:
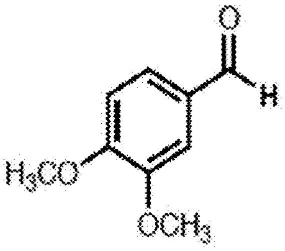
Figure 7:
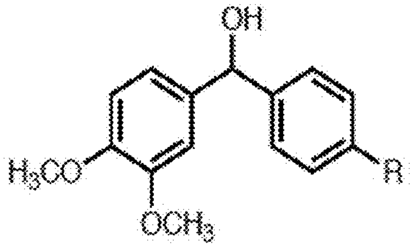
Figure 7:
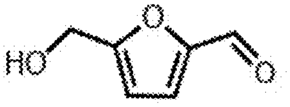
Figure 7:
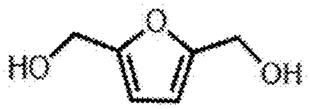

The chemical structures of benzophenone derivatives, monomers, and corresponding polymer products are shown in FIG. 7.

General Procedure for the Synthesis of Benzophenone Photoinitiators

Synthesis of Benzhydrol Derivatives 10a-10f

Figure 8:
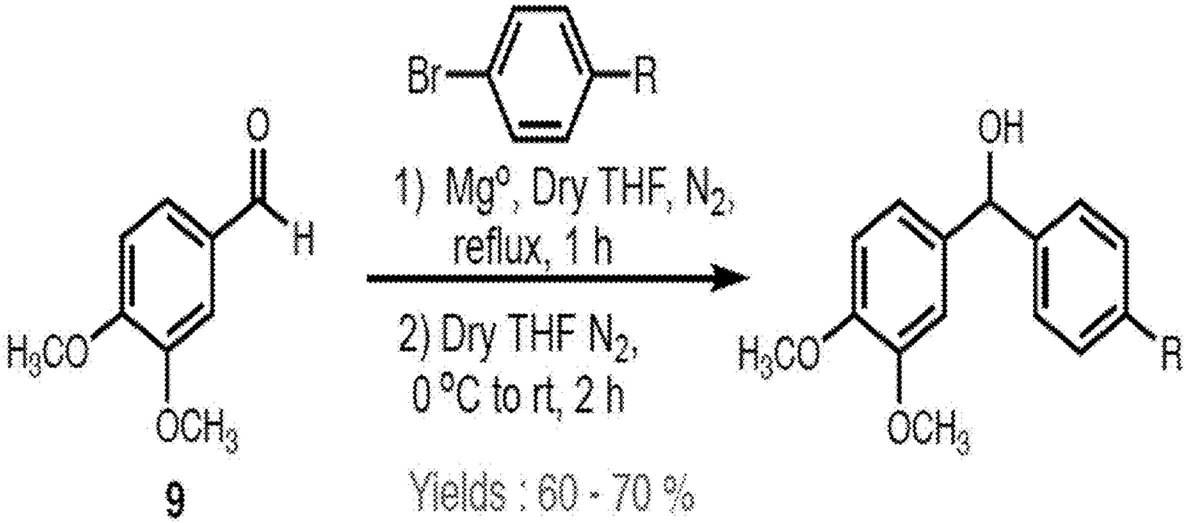
FIG. 8: Scheme 4, showing the synthesis of benzhydrol derivatives 10a-10f.

FIG. 8 shows the synthesis of benzhydrol derivatives 10a-10f.

Grignard reagents were freshly prepared from corresponding 4-bromo benzene derivatives. Veratraldehyde 9 (1 equiv) was taken in a clean and dry round bottomed flask and dissolved in dry THF and cooled the solution to 0° C. Three equivalents for ArMgBr (freshly prepared in dry THF) were added dropwise to the cooled solution 9 and stirred for ~1 h. The reaction mixture was slowly warmed to room temperature and continued stirring for ~10-12 h. The progress of the reaction was monitored by thin layer chromatography (TLC) and after the completion of reaction, ~2- to 3 mL of 10% dilute HCl and $NH_4Cl$ were added. The organic layer was extracted with EtOAc and washed with brine and water. The combined organic layers were separated, dried over anhydrous $Na_2SO_4$, and concentrated under reduced pressure to get crude product. Crude product was purified by flash chromatography (eluent: 30% EtOAc/hexanes).

10a

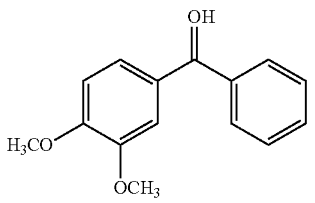

Figure 9A:
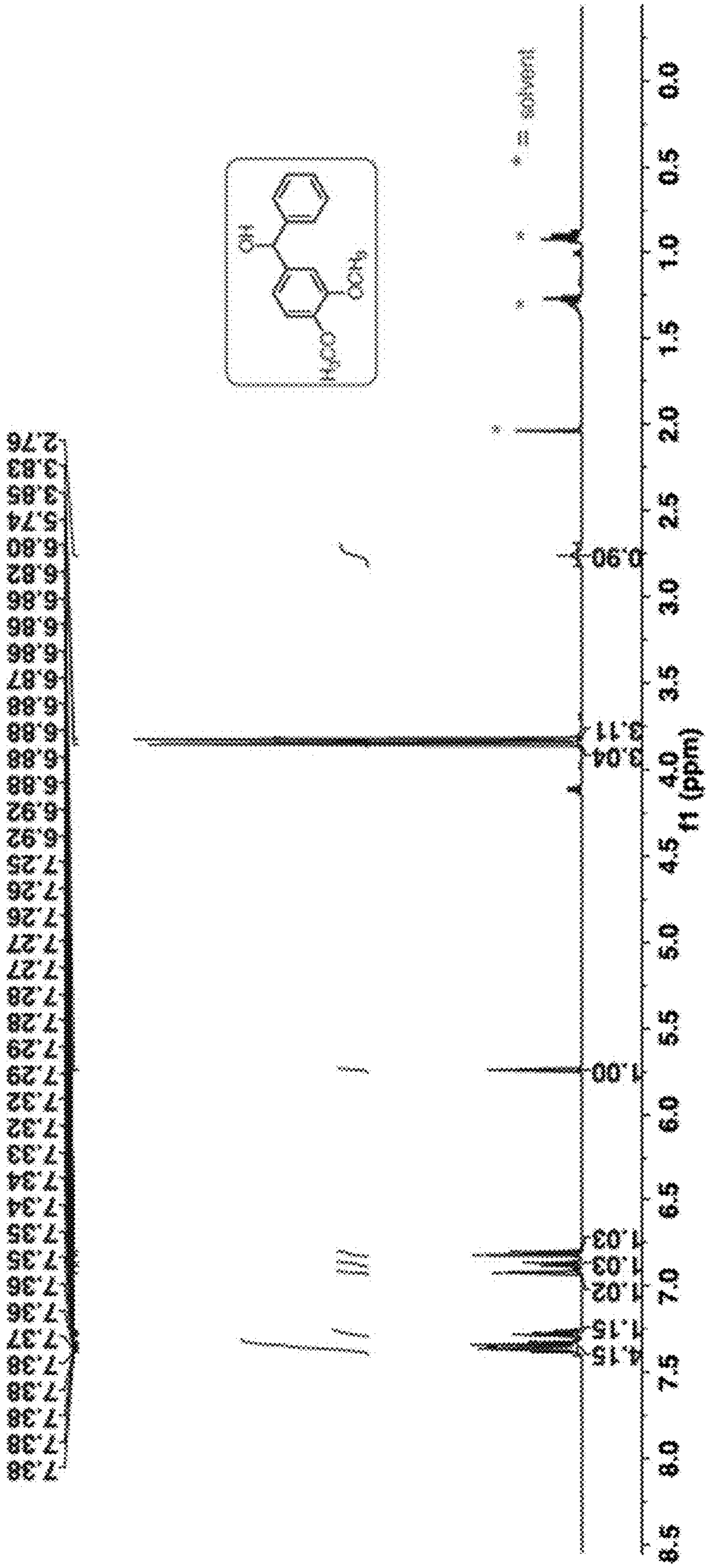
Figure 9B:
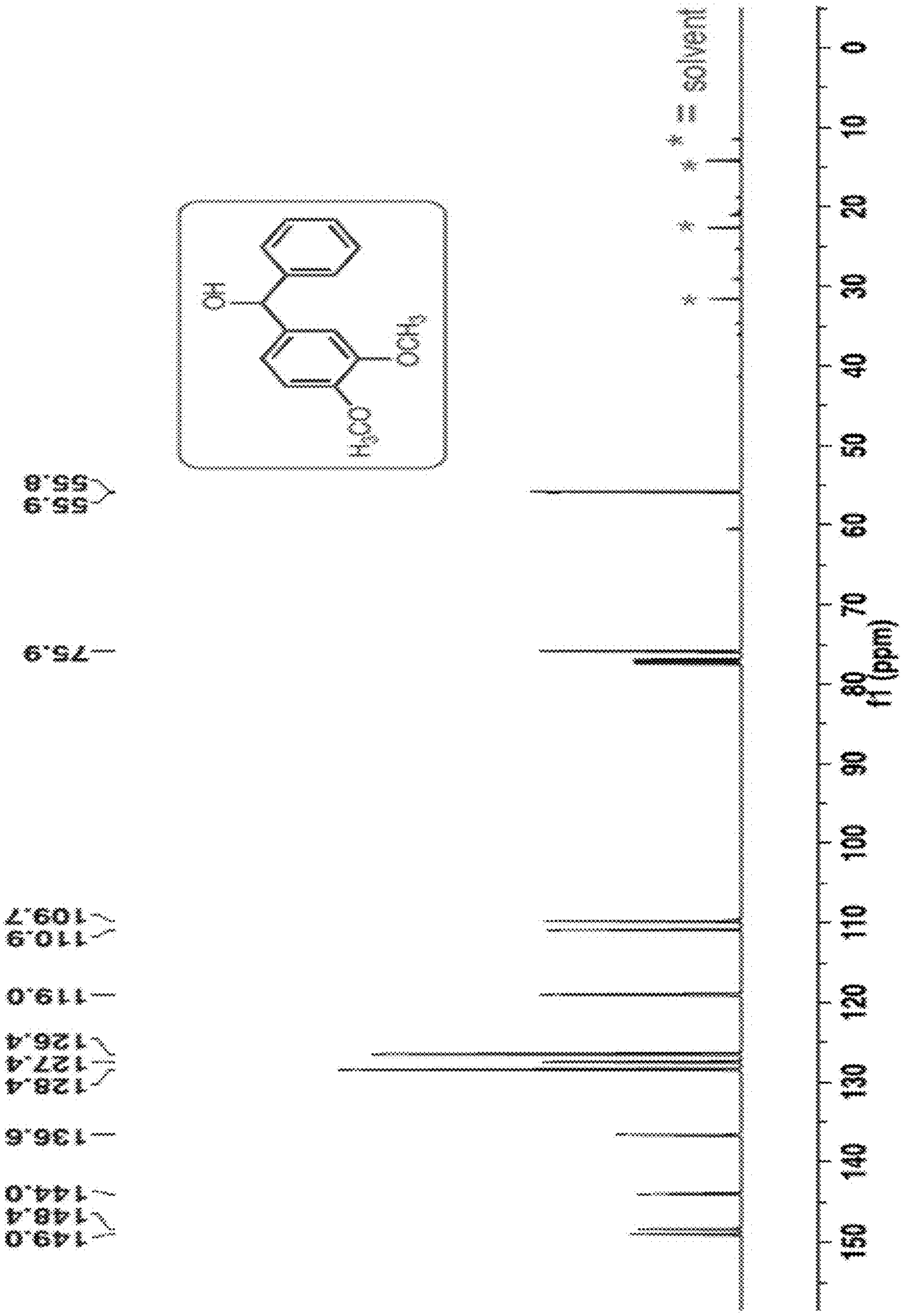

$R_f$=0.34 (70% hexanes: 30% ethyl acetate), Yield=63%. $^1$H NMR (500 MHz, $CDCl_3$, δ ppm) 7.39-7.31 (m, 4H), 7.29-7.25 (m, 1H), 6.92 (d, J=2.0 Hz, 1H), 6.87 (ddd, J=8.2, 2.0, 0.5 Hz, 1H), 6.81 (d, J=8.2 Hz, 1H), 5.74 (s, 1H), 3.85 (s, 3H), 3.83 (s, 3H), 2.76 (s, 1H). $^{13}$C NMR (125 MHz, $CDCl_3$, δ ppm) 148.9, 148.3, 143.9, 136.6, 128.4, 127.4, 126.4, 118.9, 110.8, 109.7, 75.8, 55.8, 55.8. FIG. 9A shows the $^{1}$H NMR spectrum of 10*a*, and FIG. 9B shows the $^{13}$C NMR spectrum of 10*a*.

10b

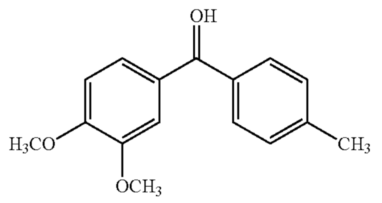

Figure 10A:
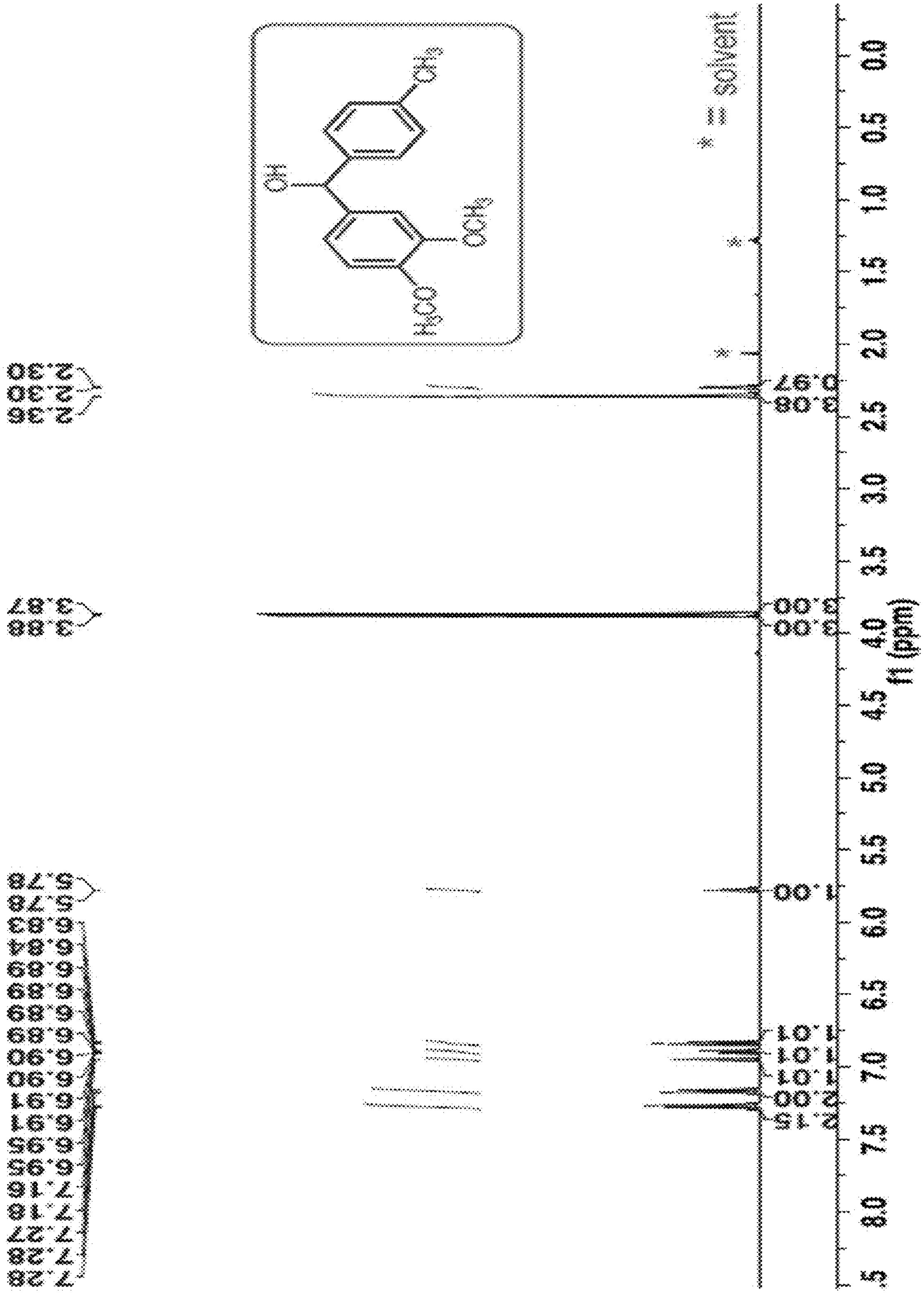
FIGS. 10A-10B: $^1H$ NMR spectrum (FIG. 10A) and $^{13}C$ NMR spectrum (FIG. 10B) of 10b.
Figure 10B:
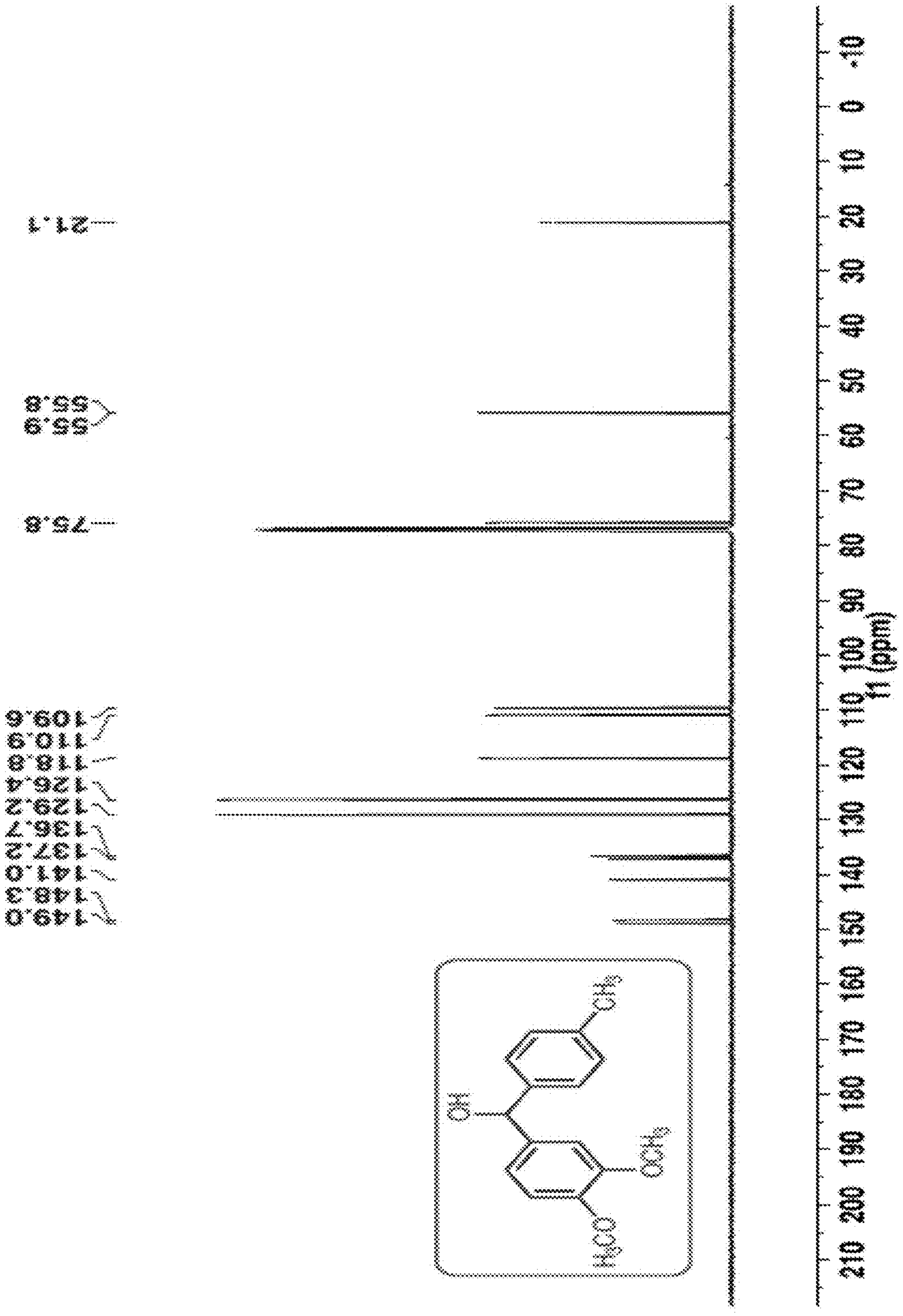

$R_f$=0.37 (70% hexanes: 30% ethyl acetate), Yield=65%. $^{1}$H NMR (500 MHz, $CDCl_3$, δ ppm) 7.31-7.24 (m, 2H), 7.17 (d, J=7.8 Hz, 2H), 6.95 (d, J=1.9 Hz, 1H), 6.90 (ddd, J=8.2, 2.0, 0.5 Hz, 1H), 6.84 (d, J=8.2 Hz, 1H), 5.78 (d, J=2.4 Hz, 1H), 3.88 (s, 3H), 3.87 (s, 3H), 2.36 (s, 3H), 2.30 (d, J=3.2 Hz, 1H). $^{13}$C NMR (125 MHz, $CDCl_3$, δ ppm) 148.9, 148.3, 141.0, 137.2, 136.7, 129.1, 126.4, 118.8, 110.8, 109.6, 75.8, 55.9, 55.8, 21.1. FIG. 10A shows the $^{1}$H NMR spectrum of 10b, and FIG. 10B shows the $^{13}$C NMR spectrum of 10b.

10c

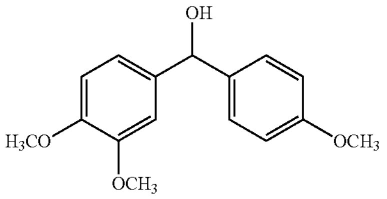

Figure 11A:
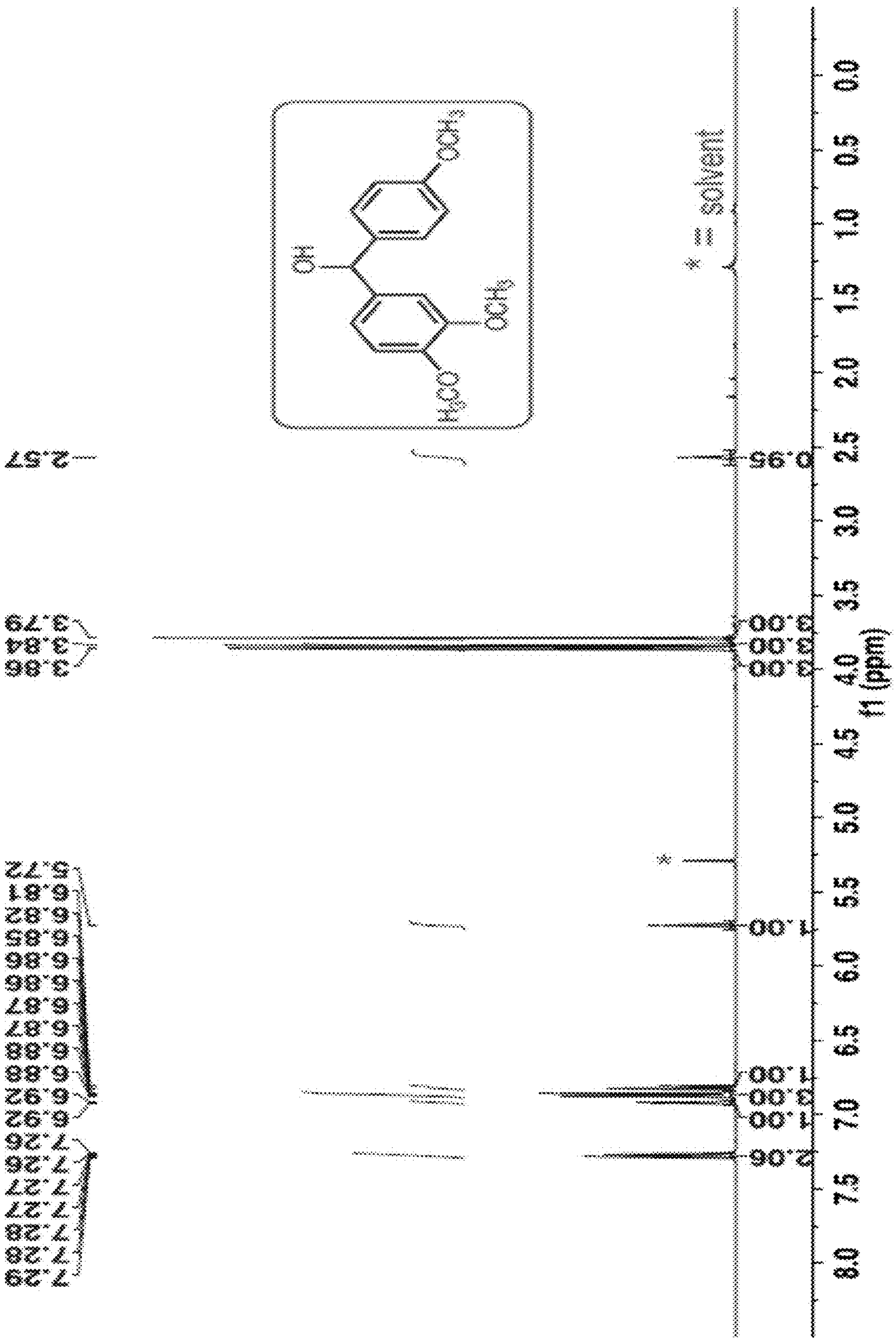
FIGS. 11A-11B: $^1H$ NMR spectrum (FIG. 11A) and $^{13}C$ NMR spectrum (FIG. 11B) of 10c.
Figure 11B:
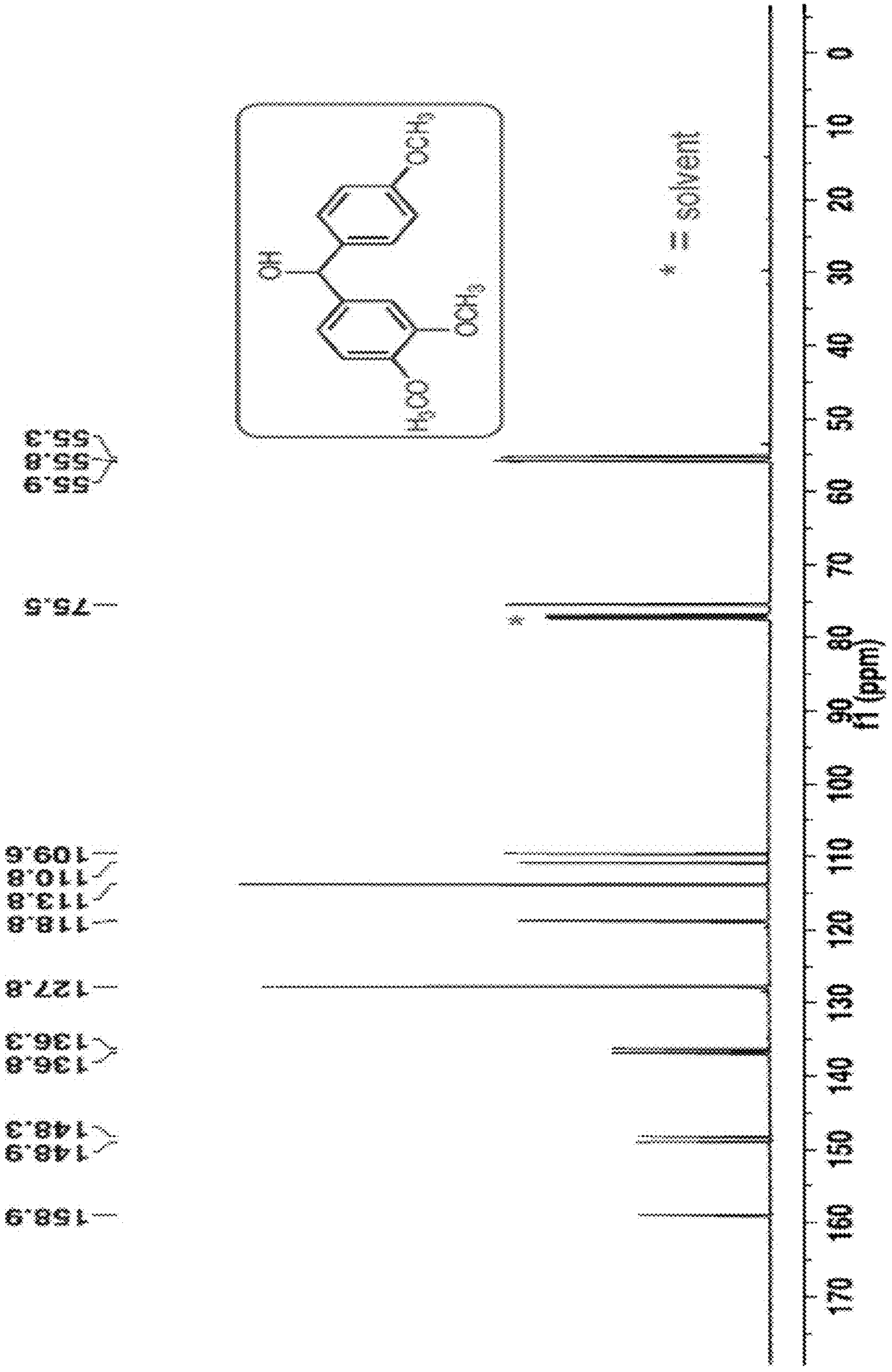

$R_f$=0.28 (70% hexanes: 30% ethyl acetate), Yield=62%. $^{1}$H NMR (500 MHz, $CDCl_3$, δ ppm) 7.29-7.25 (m, 2H), 6.92 (d, J=1.9 Hz,1H), 6.89 — 6.84 (m, 3H), 6.82 (d, J=8.2 Hz, 1H), 5.72 (s, 1H), 3.86 (s, 3H), 3.84 (s, 3H), 3.79 (s, 3H), 2.57 (s, 1H). $^{13}$C NMR (125 MHz, $CDCl_3$, δ ppm) 158.9, 148.9, 148.2, 136.8, 136.3, 127.7, 118.7, 113.7, 110.8, 109.6, 75.4, 55.9, 55.8, 55.2. FIG. 11A shows the $^{1}$H NMR spectrum of 10c, and FIG. 11B shows the $^{13}$C NMR spectrum of 10c.

10d

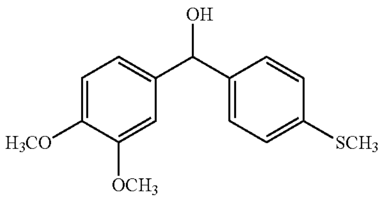

Figure 12A:
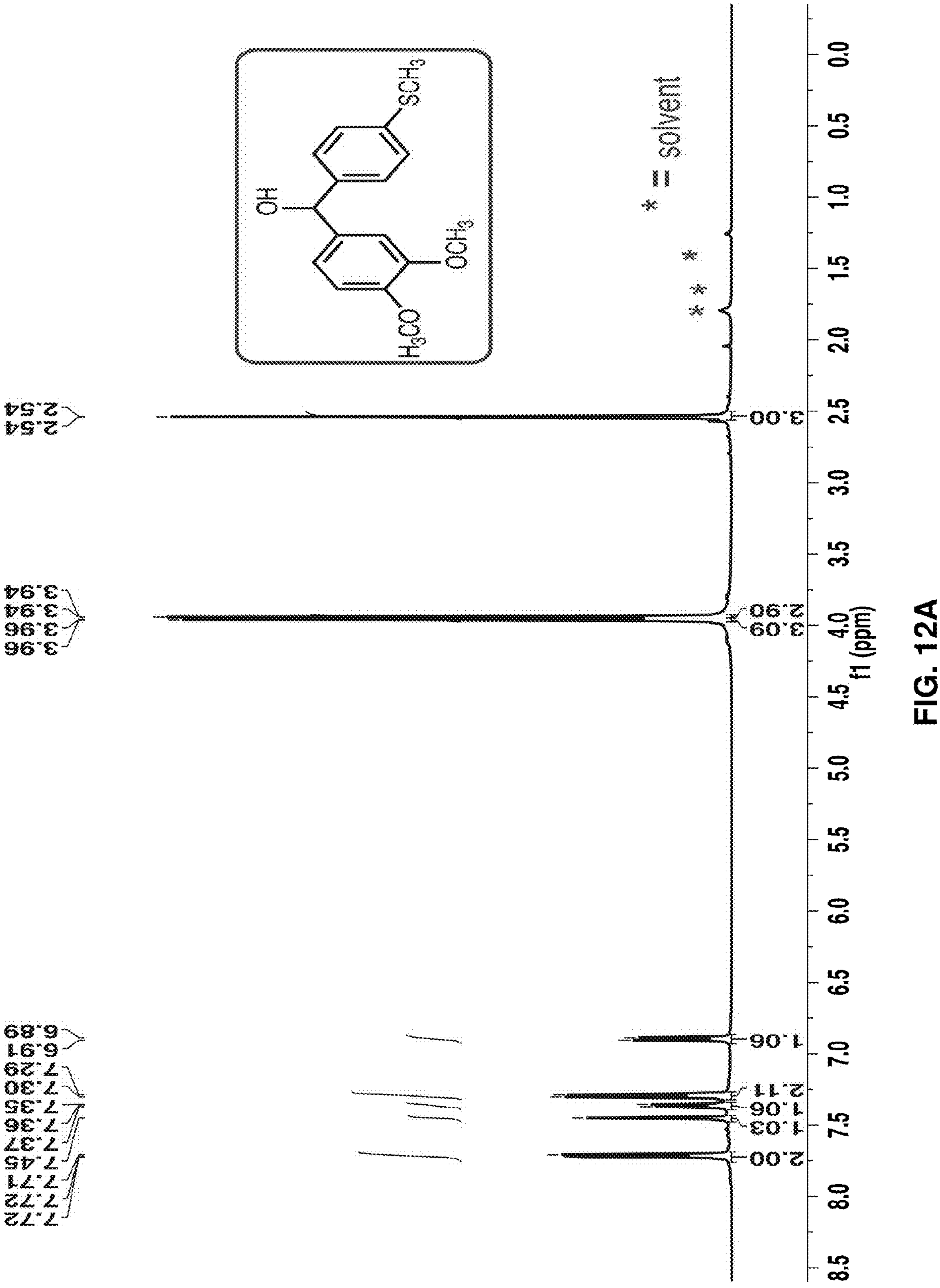
FIGS. 12A-12B: $^1H$ NMR spectrum (FIG. 12A) and $^{13}C$ NMR spectrum (FIG. 12B) of 10d.
Figure 12B:
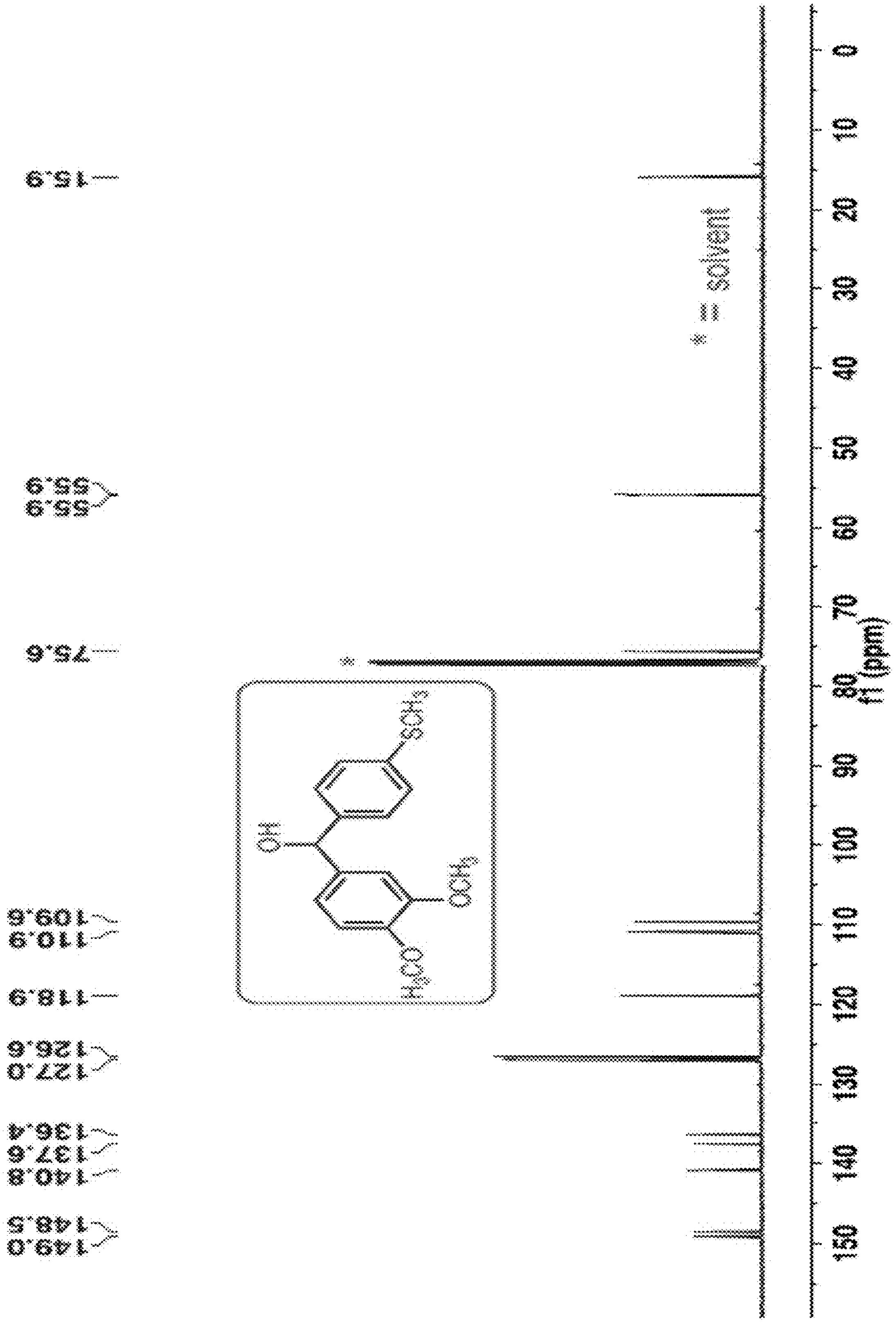

$R_f$=0.25 (70% hexanes: 30% ethyl acetate), Yield=64%. $^{1}$H NMR (500 MHz, $CDCl_3$, δ ppm) 7.30 (dd, J=8.5, 6.8 Hz, 2H), 7.26-7.22 (m, 2H), 6.94-6.81 (m, 3H), 5.77 (d, J=2.9 Hz, 1H), 3.88 (s, 3H), 3.86 (s, 3H), 2.49 (s, 3H), 2.30 (d, J=3.4 Hz, 1H). $^{13}$C NMR (125 MHz, $CDCl_3$, δ ppm) 149.0, 148.4, 140.8, 137.5, 136.3, 126.9, 126.5, 118.8, 110.8, 109.6, 75.5, 55.9, 55.8, 15.8. FIG. 12A shows the $^{1}$H NMR spectrum of 10d, and FIG. 12B shows the $^{13}$C NMR spectrum of 10d.

10e

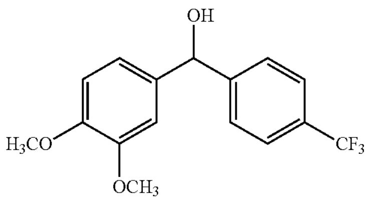

Figure 13A:
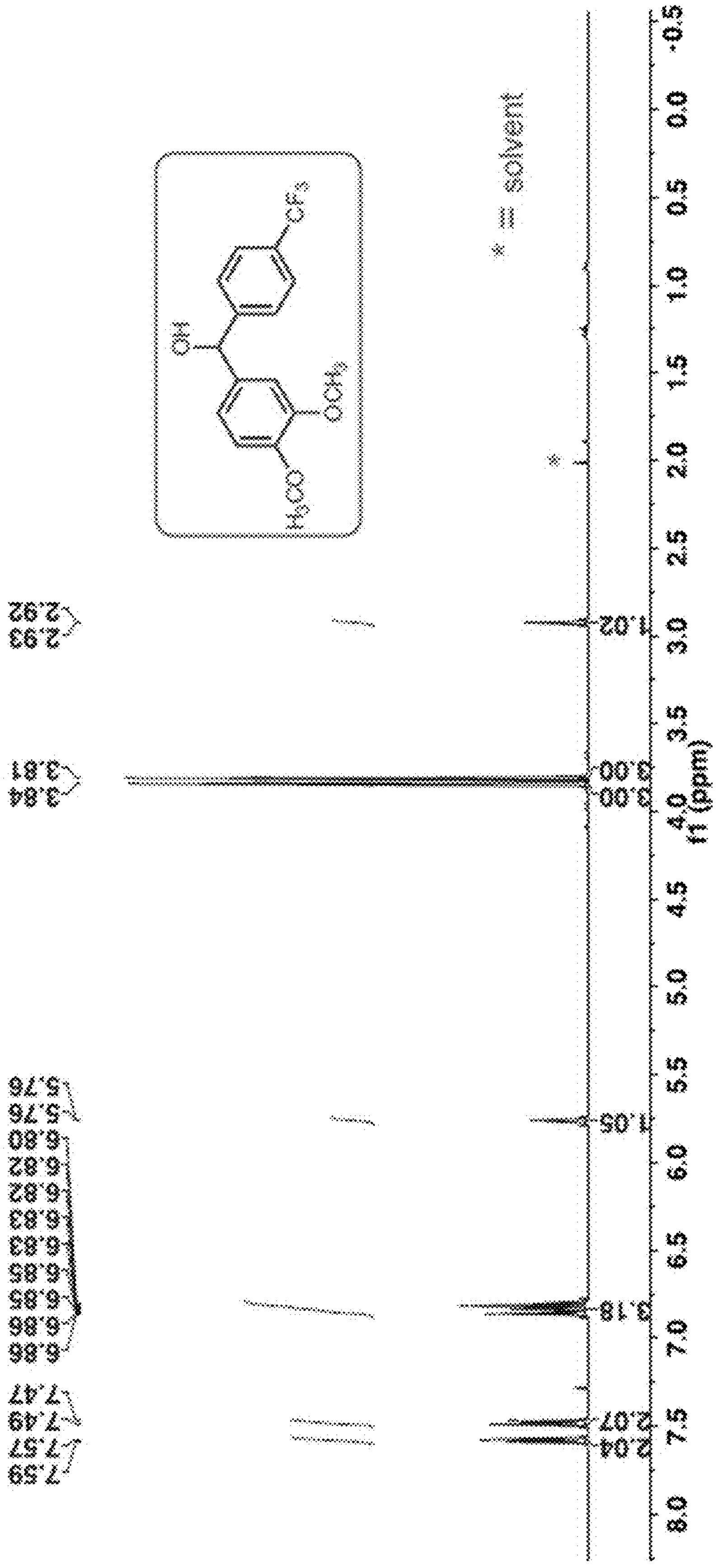
FIGS. 13A-13B: $^1H$ NMR spectrum (FIG. 13A) and $^{13}C$ NMR spectrum (FIG. 13B) of 10e.
Figure 13B:
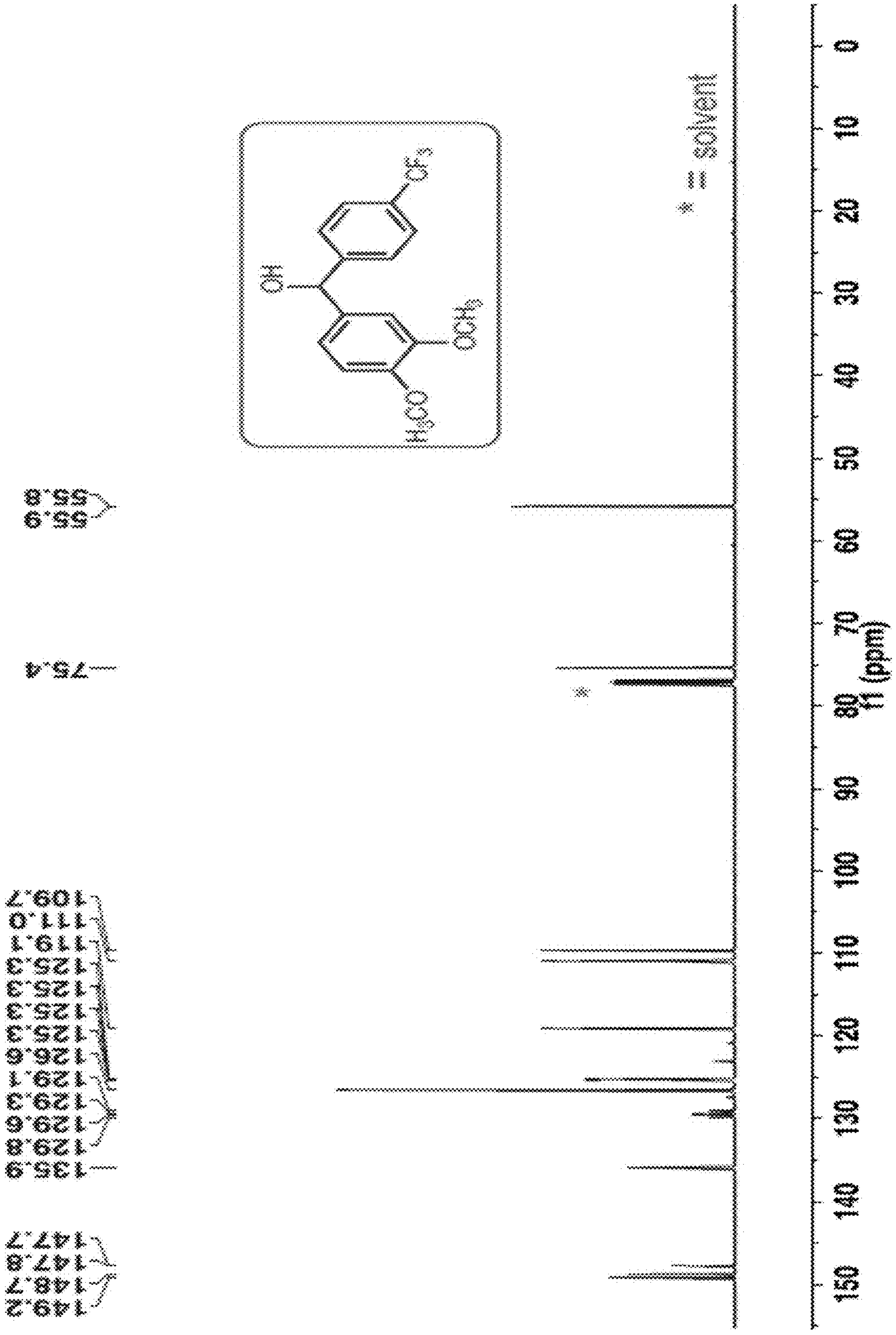

$R_f$=0.31 (70% hexanes: 30% ethyl acetate), Yield=64%. $^{1}$H NMR (500 MHz, $CDCl_3$, δ ppm) 7.58 (d, J=8.2 Hz, 2H), 7.48 (d, J=8.6 Hz, 2H), 6.88 — 6.78 (m, 3H), 5.76 (d, J=2.4 Hz, 1H), 3.84 (s, 3H), 3.81 (s, 3H), 2.92 (d, J=3.2 Hz, 1H). $^{13}$C NMR (125 MHz, $CDCl_3$, δ ppm) 149.1, 148.7, 147.7, 147.7, 135.8, 129.8, 129.5, 129.3, 129.0, 126.5, 125.3, 125.3, 125.2, 125.2, 119.1, 110.9, 109.6, 75.3, 55.8, 55.8. FIG. 13A shows the $^{1}$H NMR spectrum of 10e, and FIG. 13B shows the $^{13}$C NMR spectrum of 10e.

10f

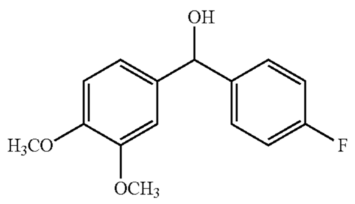

Figure 14A:
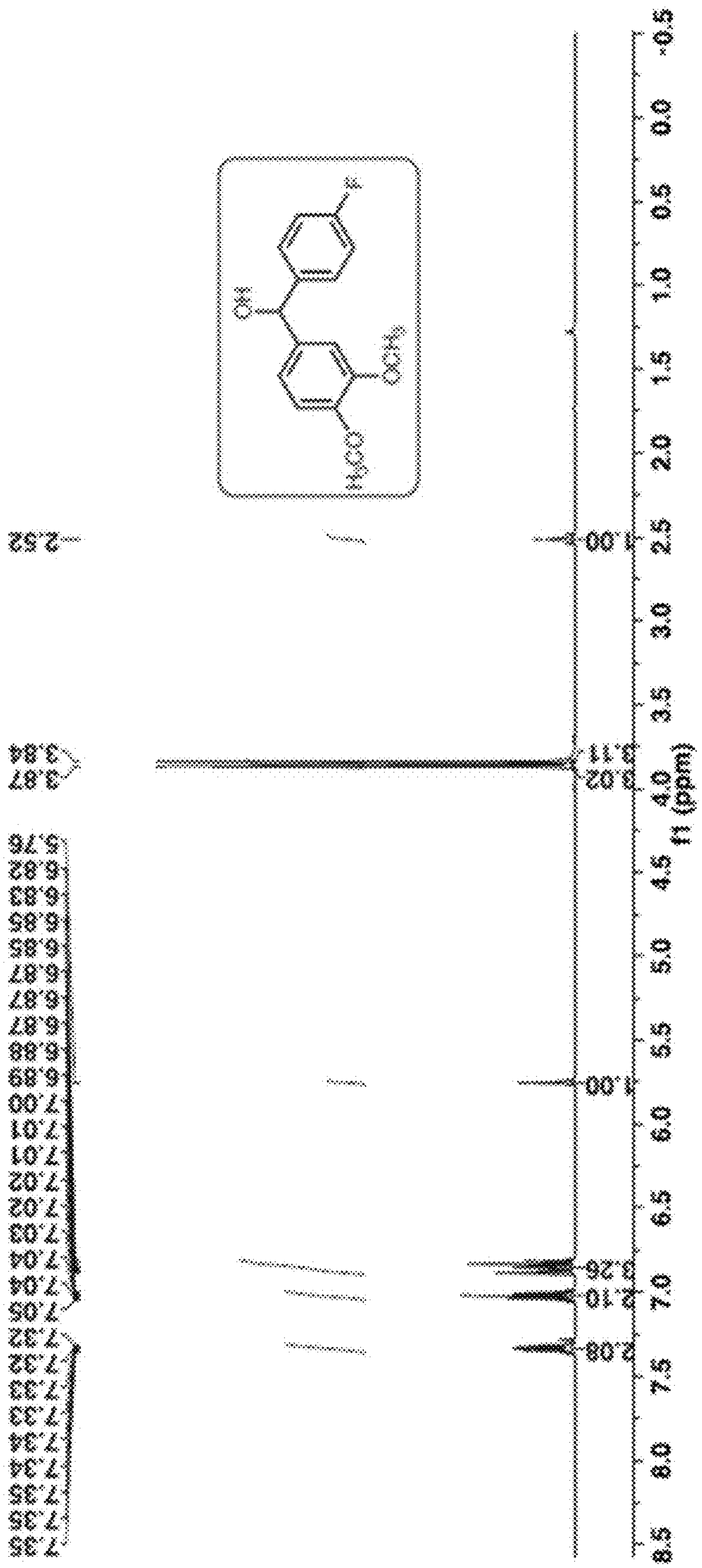
FIGS. 14A-14B: $^1H$ NMR spectrum (FIG. 14A) and $^{13}C$ NMR spectrum (FIG. 14B) of 10f.
Figure 14B:
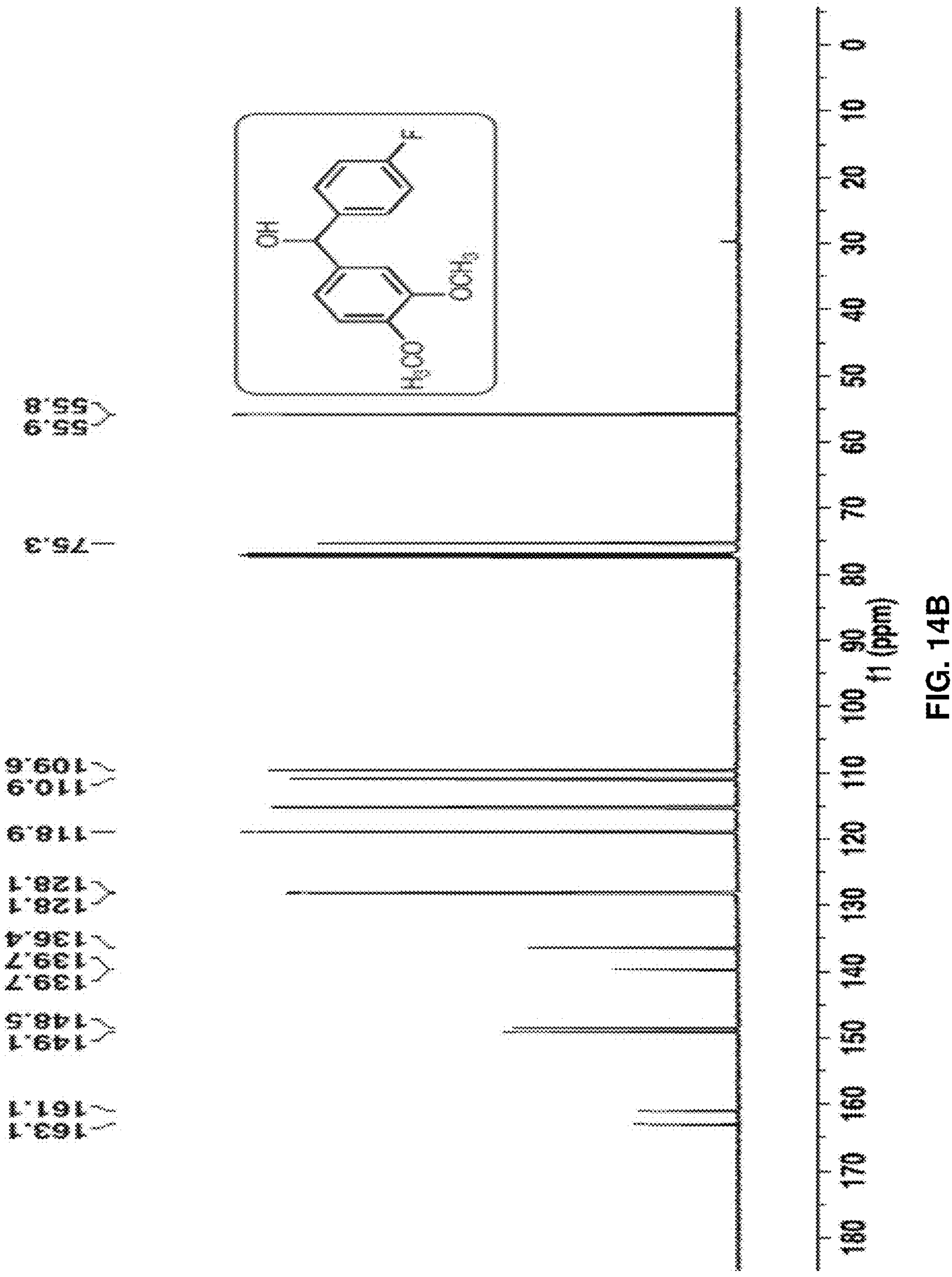

$R_f$=0.31 (70% hexanes: 30% ethyl acetate), Yield=60%. $^{1}$H NMR (500 MHz, $CDCl_3$, δ ppm) 7.33 (ddd, J=9.8, 5.1, 2.3 Hz, 2H), 7.07-6.99 (m, 2H), 6.92-6.80 (m, 3H), 5.76 (s, 1H), 3.87 (s, 3H), 3.84 (s, 3H), 2.52 (s, 1H). 13C NMR (125 MHz, $CDCl_3$, δ ppm) 163.0, 161.1, 149.0, 148.5, 139.6, 139.6, 136.3, 128.1, 128.0, 118.8, 110.9, 109.6, 75.3, 55.9, 55.8. FIG. 14A shows the $^{1}$H NMR spectrum of 10f, and FIG. 14B shows the $^{13}$C NMR spectrum of 10f.

Synthesis of Benzophenone Photoinitiators 1a-1f

Figure 15:
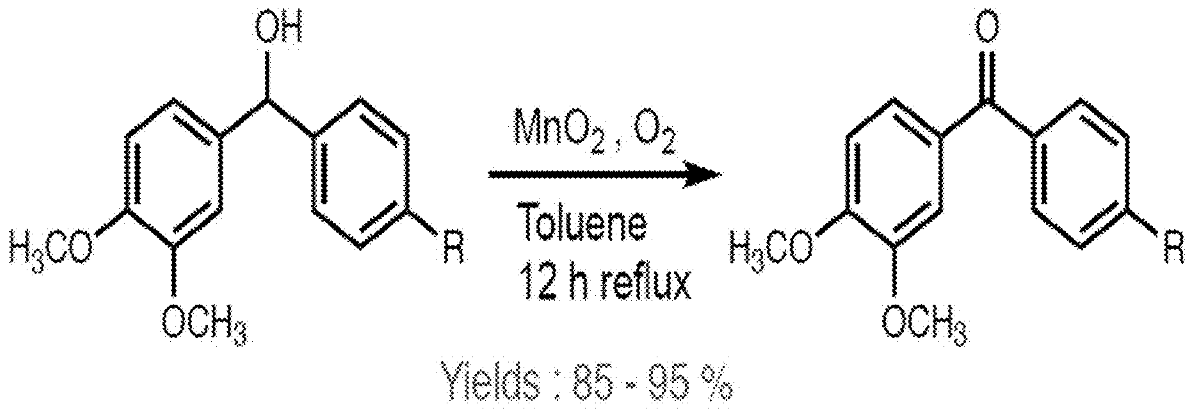
FIG. 15: Scheme 5, showing the synthesis of benzophenone photoinitiators 1a-1f.

FIG. 15 depicts the synthesis of benzophenone photoinitiators 1a-1f.

The benzhydrol derivative (1 equiv) was dissolved in toluene and $MnO_2$ (100 mg per mmol of benzhydrol) was added. The solution was purged with oxygen for ~30 min and the reaction mixture was refluxed for ~12 h. The consumption of benzhydrol derivative was monitored by TLC and after the reaction, the crude mixture was filtered through celite bed to remove the solids byproducts and unreacted $MnO_2$. The solvent was removed under reduced pressure and crude product was collected. By using column chromatography (eluent: 30% EtOAc/hexanes) the product 1a-1f was purified.

1a

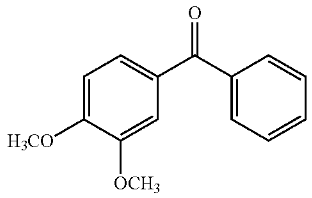

Figure 16A:
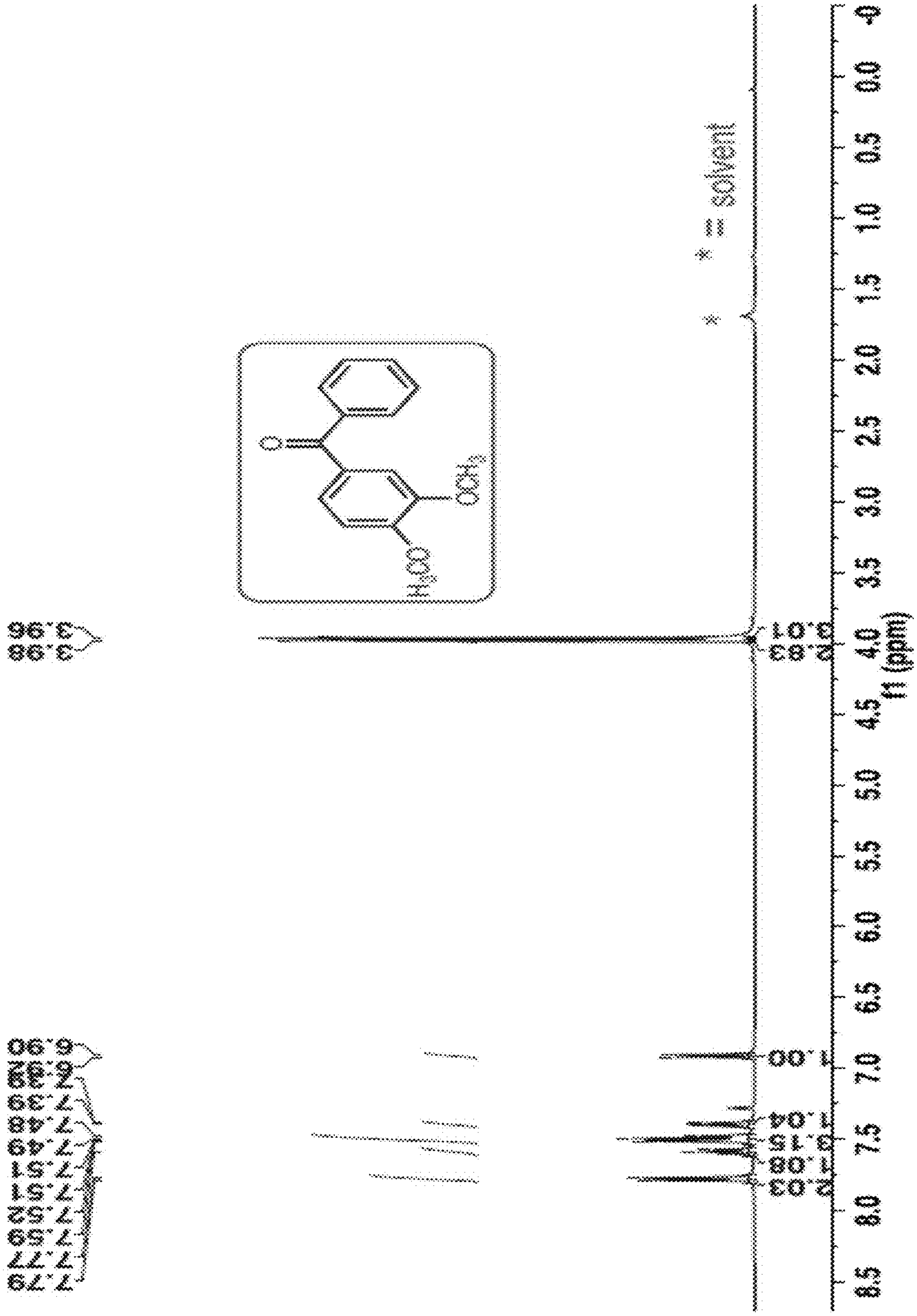
Figure 16B:
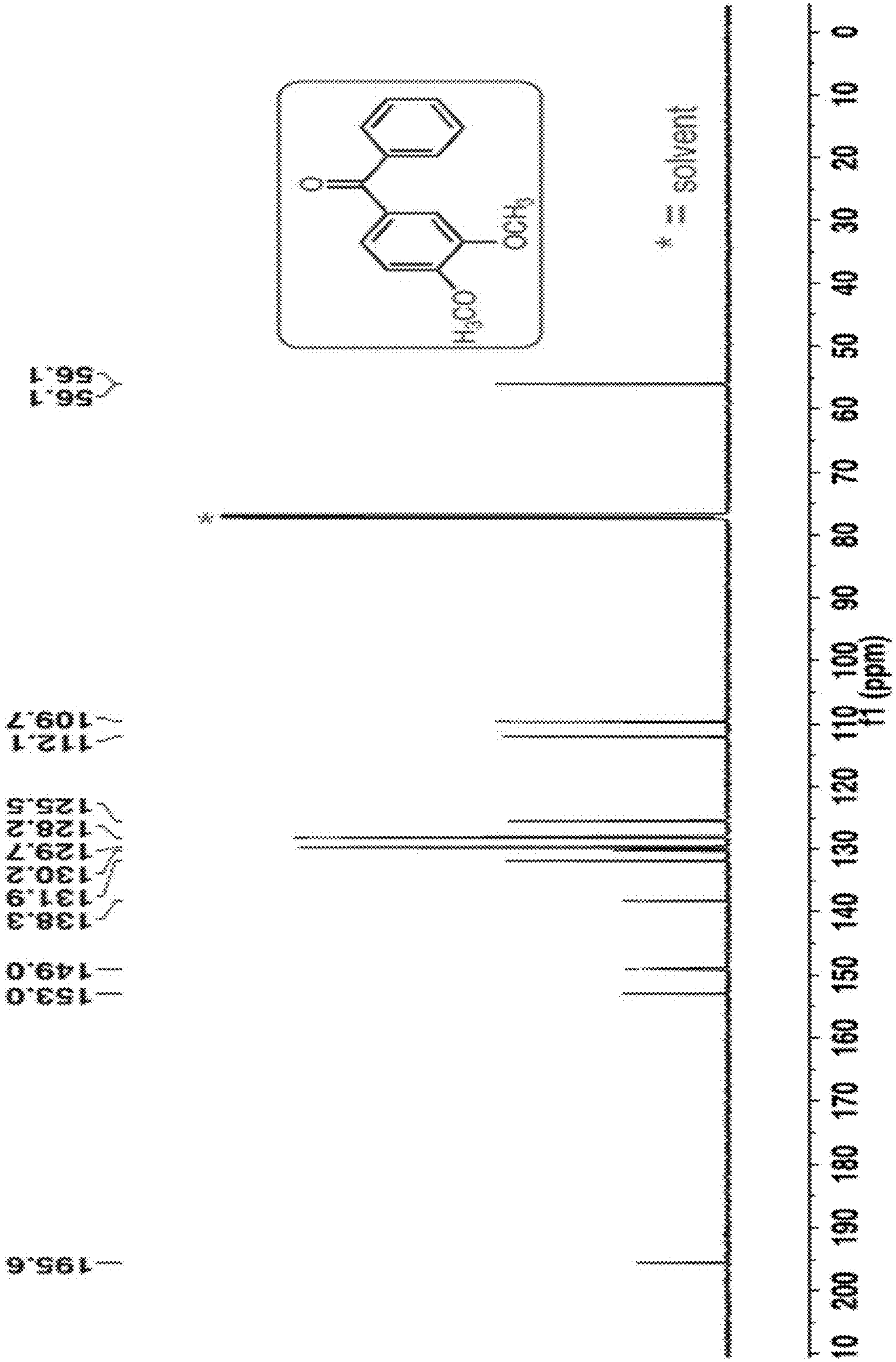
Figure 16C:
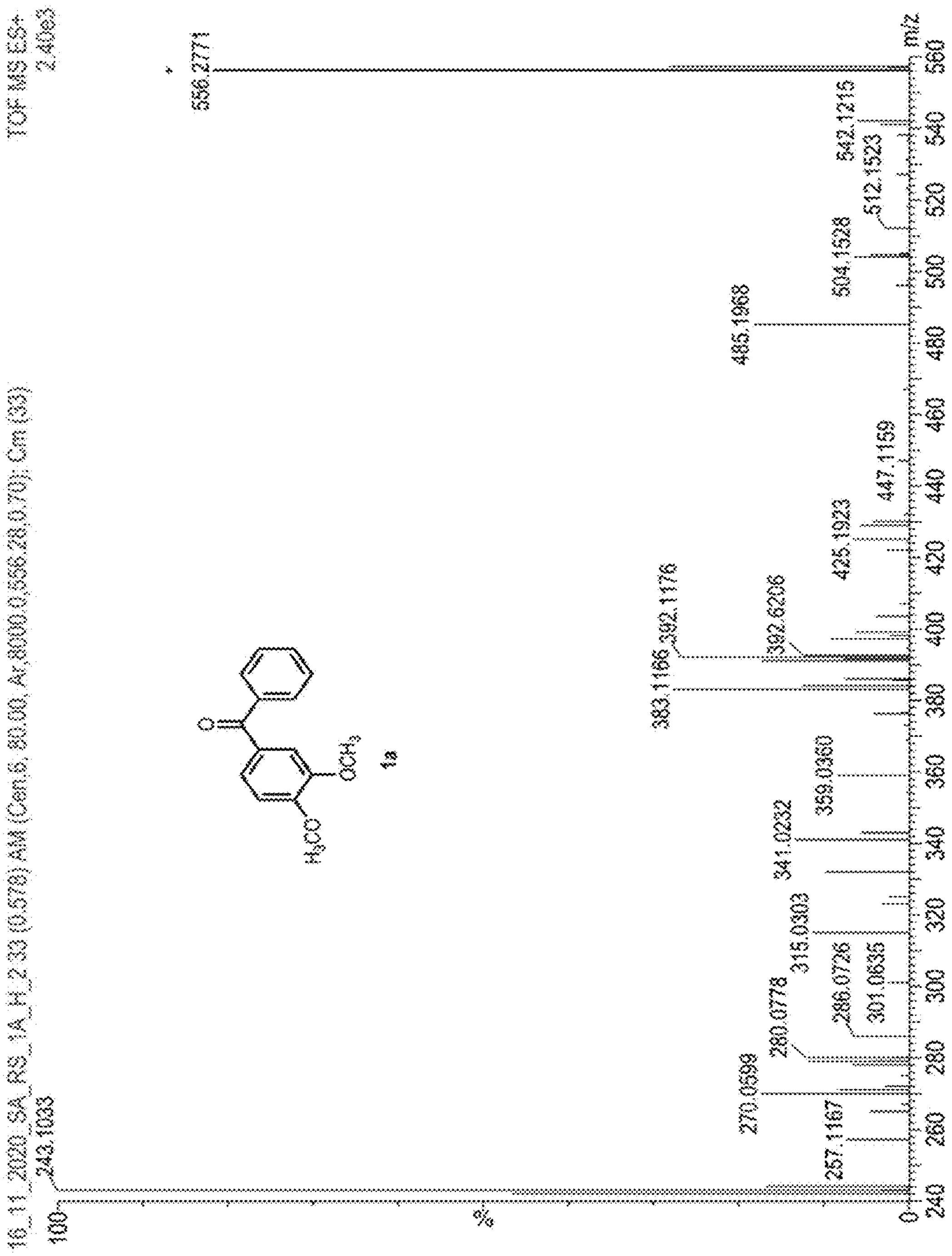

$R_f$=0.5 (70% hexanes: 30% ethyl acetate), Yield=89%. $^1$H NMR (500 MHz, $CDCl_3$, δ ppm) 7.78 (d, J=7.3 Hz, 2H), 7.59 (t, J=7.4 Hz, 1H), 7.53-7.46 (m, 3H), 7.43-7.35 (m, 1H), 6.91 (d, J=8.3 Hz, 1H), 3.98 (s 3H), 3.96 (s 3H). $^{13}$C NMR (125 MHz, $CDCl_3$, δ ppm) 195.61, 153.01, 148.99, 138.27, 131.90, 130.19, 129.73, 128.18, 125.53, 112.07, 109.71, 56.11, 56.06. Mass accuracy (m/z) ($[M+H]^+$:=[(243.1033-243.1021)/243.1033]*$10^6$=4.9 ppm. FIG. 16A shows the $^1$H NMR spectrum of 1a, FIG. 16B shows the $^{13}$C NMR spectrum of 1a, and FIG. 16C shows the HRMS-ESI spectrum of 1a.

1b

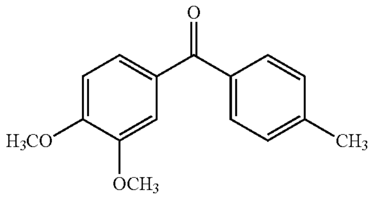

Figure 17A:
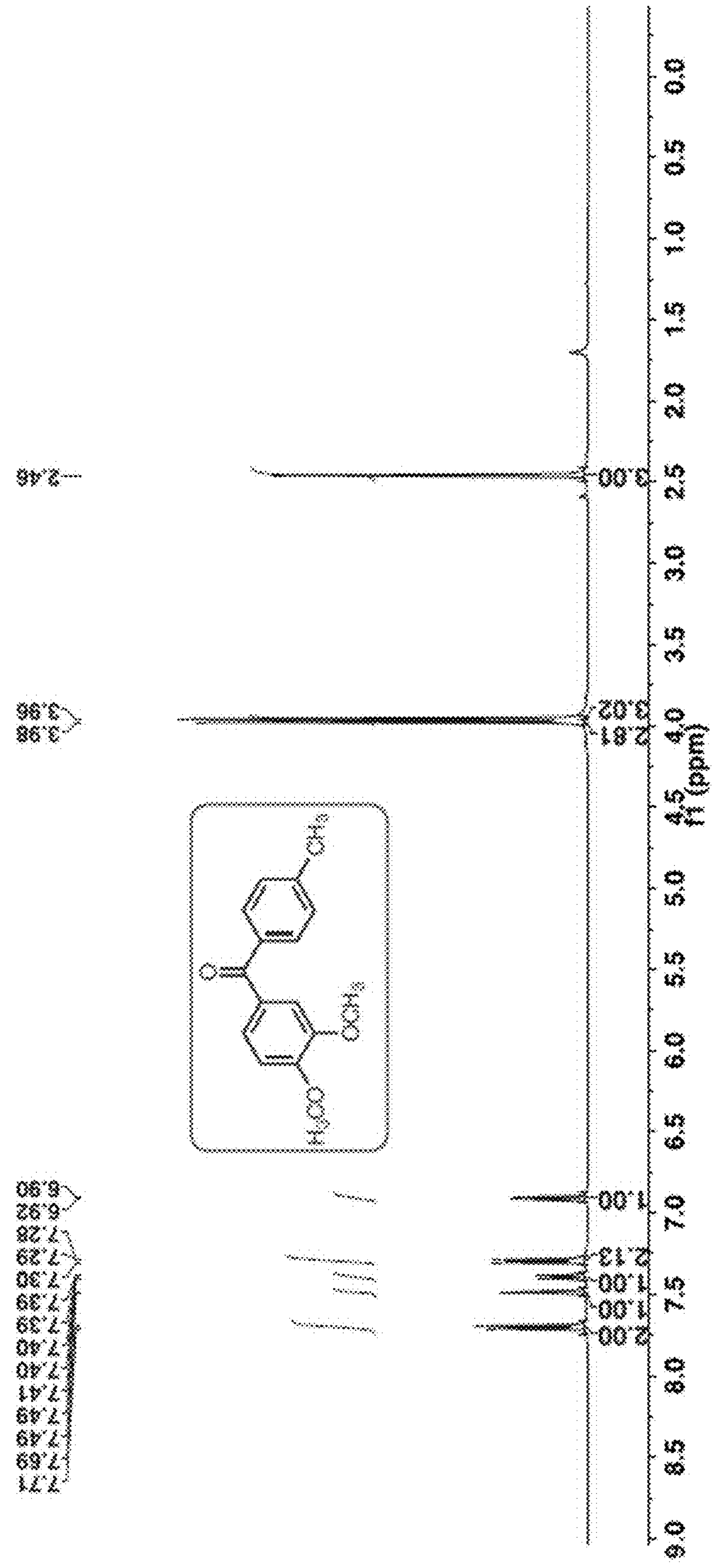
FIGS. 17A-17C: $^1H$ NMR spectrum (FIG. 17A), $^{13}C$ NMR spectrum (FIG. 17B), and HRMS-ESI spectrum (FIG. 17C) of 1b.
Figure 17B:
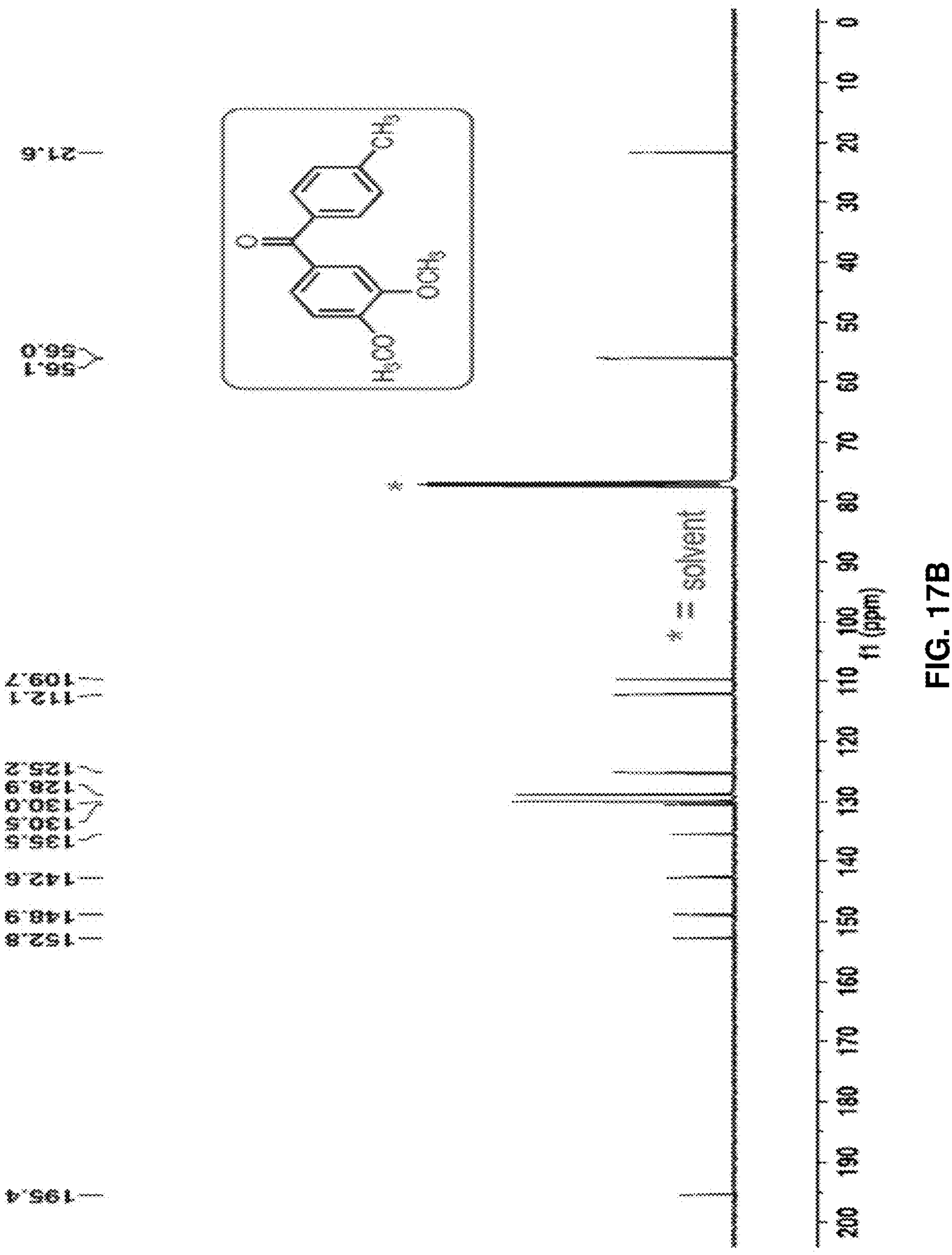
Figure 17C:
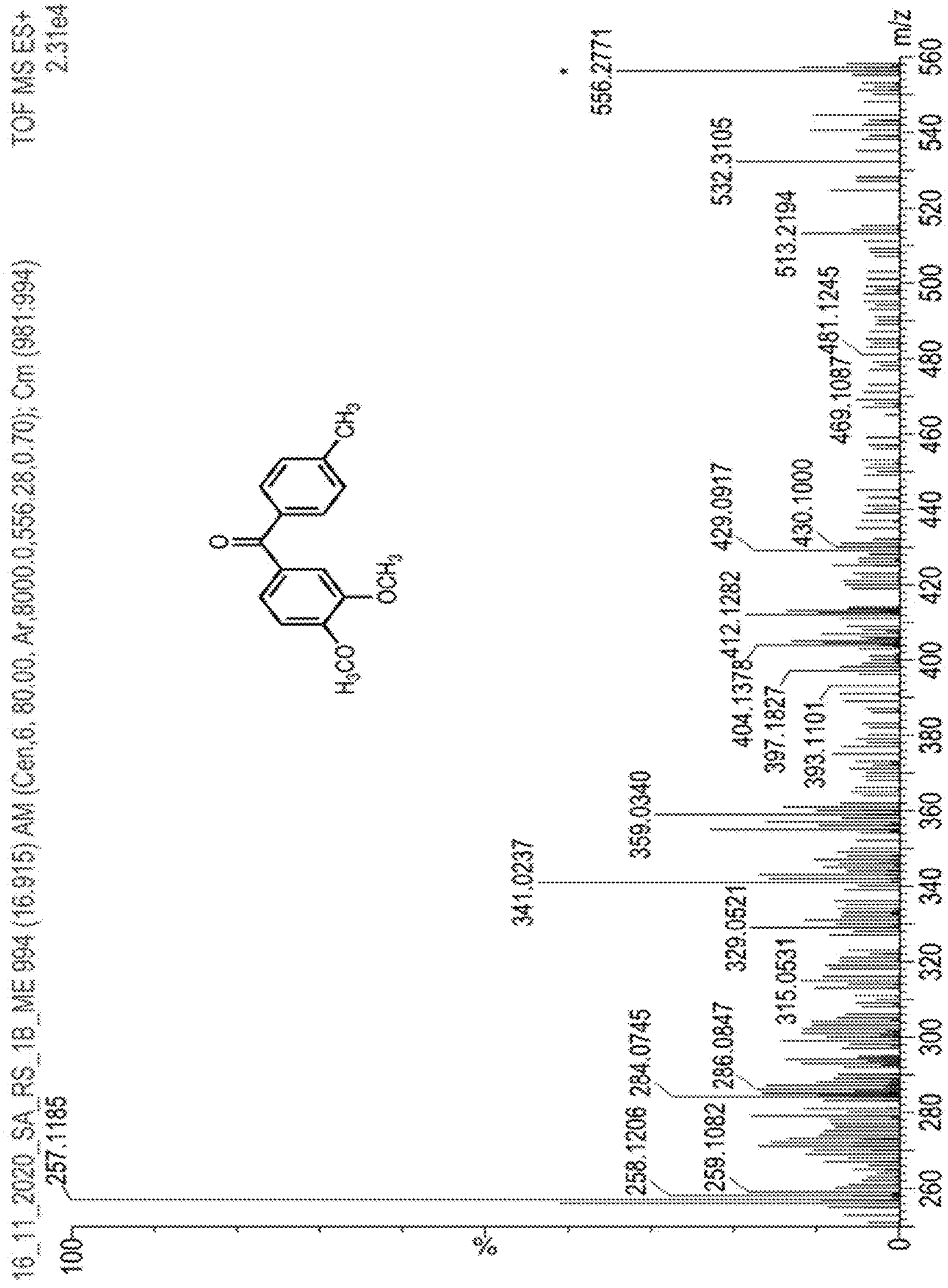

$R_f$=0.46 (70% hexanes: 30% ethyl acetate), Yield=90%. $^1$H NMR (500 MHz, $CDCl_3$, δ ppm) 7.70 (d, J=8.0 Hz, 2H), 7.49 (d, J=1.8 Hz, 1H), 7.44-7.36 (m, 1H), 7.32-7.24 (m, 2H), 6.91 (d, J=8.3 Hz, 1H), 3.98 (s 3H), 3.96 (s 3H), 2.46 (s, 3H). $^{13}$C NMR (125 MHz, $CDCl_3$, δ ppm) 195.4, 152.7, 148.9, 142.6, 135.4, 130.5, 130.0, 128.8, 125.2, 112.1, 109.6, 56.1, 56.0, 21.6. Mass accuracy (m/z) ($[M+H]^+$:=[(257.1185- 257.1177)/257.1185]*$10^6$=3.1 ppm. FIG. 17A shows the $^1$H NMR spectrum of 1b, FIG. 17B shows the $^{13}$C NMR spectrum of 1b, and FIG. 17C shows the HRMS-ESI spectrum of 1b.

1c

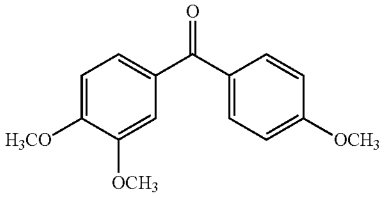

Figure 18A:
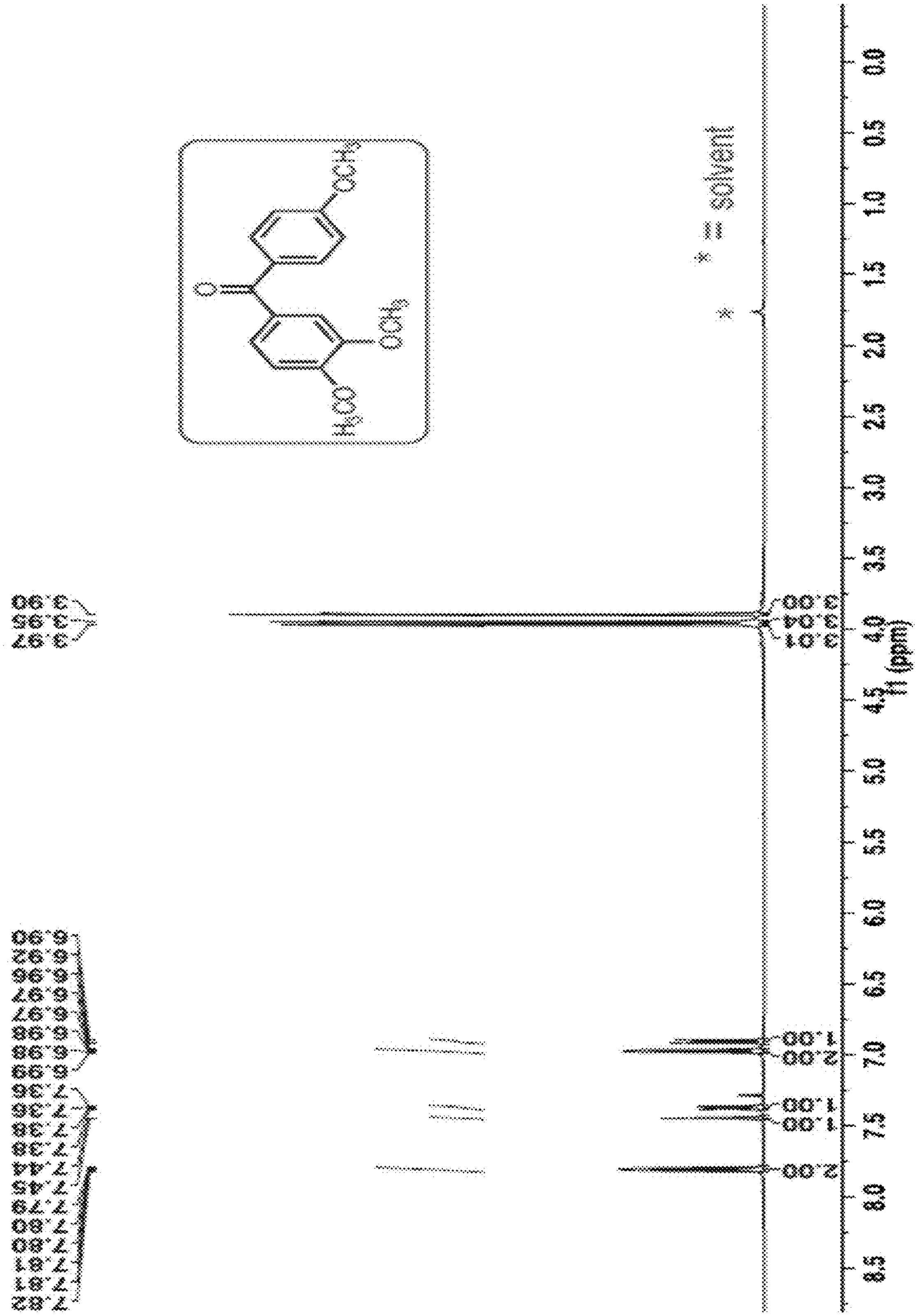
FIGS. 18A-18C: $^1H$ NMR spectrum (FIG. 18A), $^{13}C$ NMR spectrum (FIG. 18B), and HRMS-ESI spectrum (FIG. 18C) of 1c.
Figure 18B:
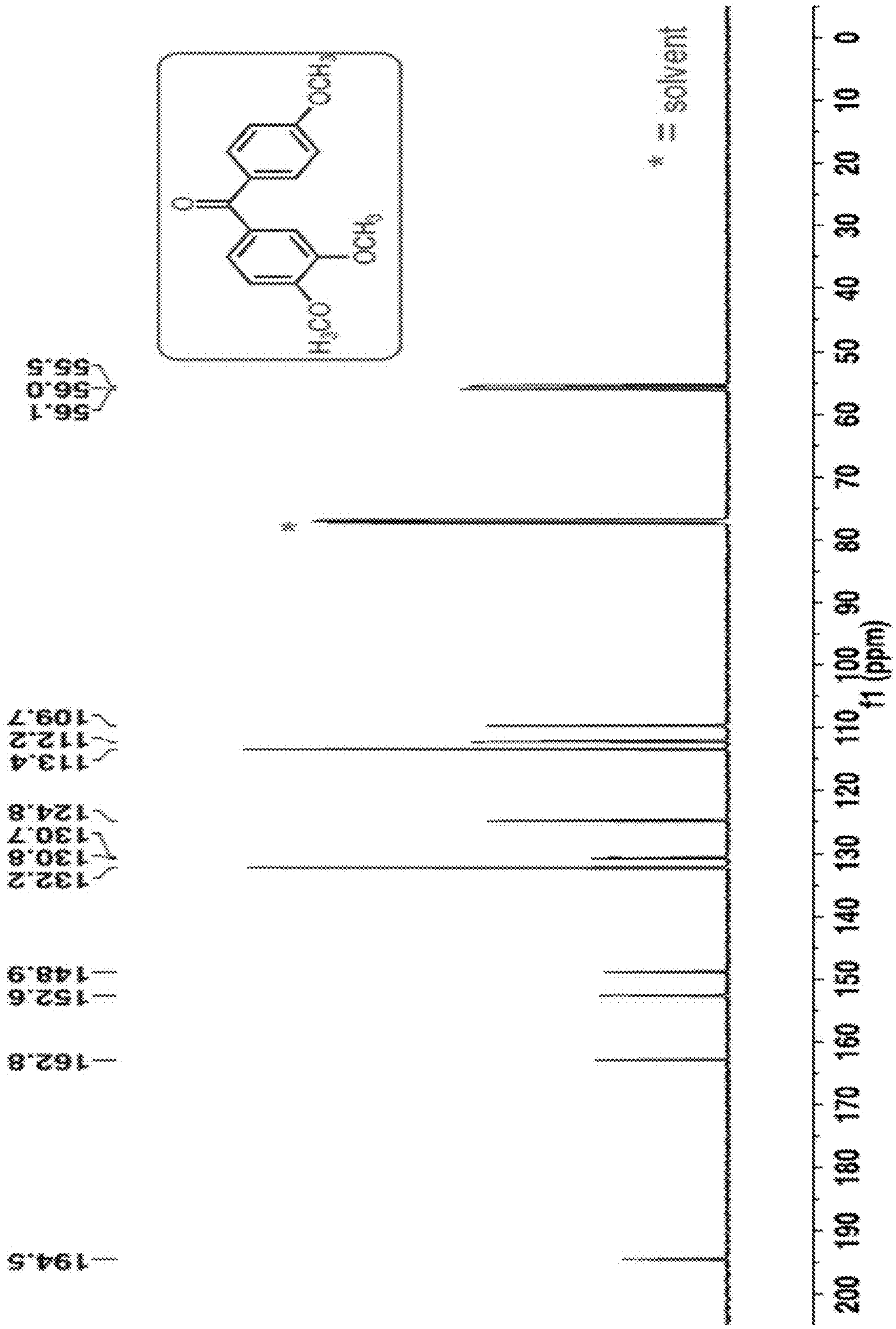
Figure 18C:
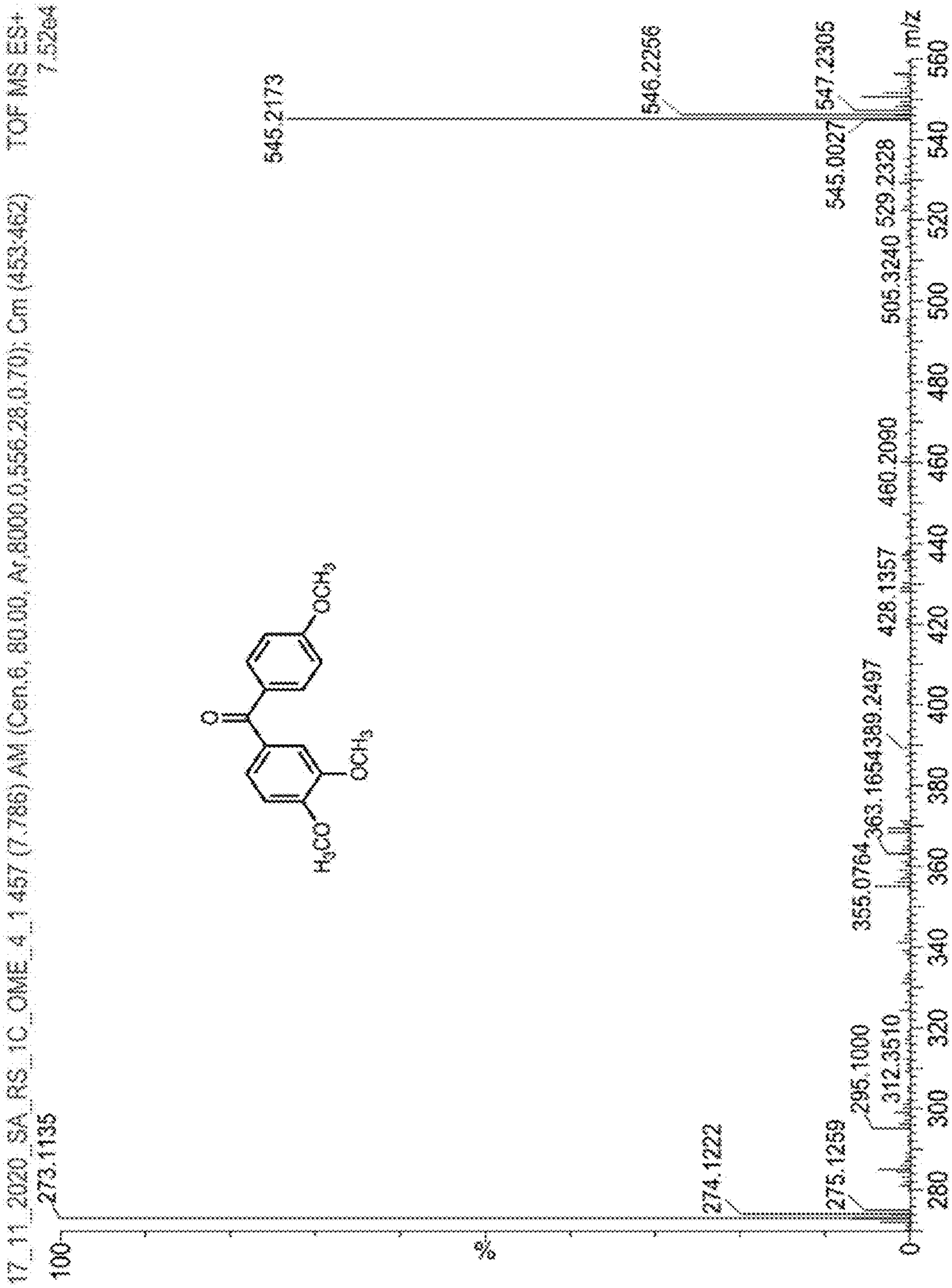

$R_f$=0.33 (70% hexanes: 30% ethyl acetate), Yield=92%. $^1$H NMR (500 MHz, $CDCl_3$, δ ppm) 7.86-7.74 (m, 2H), 7.44 (d, J=1.9 Hz, 1H), 7.37 (dd, J=8.3, 2.0 Hz, 1H), 7.08-6.94 (m, 2H), 6.91 (d, J=8.3 Hz, 1H), 3.97 (s, 3H), 3.95 (s, 3H), 3.90 (s, 3H). $^{13}$C NMR (125 MHz, $CDCl_3$, δ ppm) 194.4, 162.8, 152.6, 148.9, 132.2, 130.8, 130.7, 124.8, 113.4, 112.2, 109.7, 56.1, 56.0, 55.5. Mass accuracy (m/z) ($[M+H]^+$: =[(273.126-273.1135)/273.1125]*$10^6$=3.2 ppm. FIG. 18A shows the $^1$H NMR spectrum of 1c, FIG. 18B shows the $^{13}$C NMR spectrum of 1c, and FIG. 18C shows the HRMS-ESI spectrum of 1c.

1d

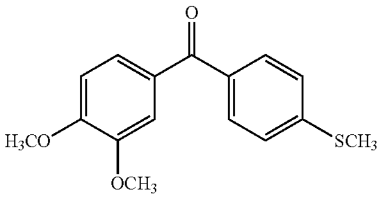

Figure 19A:
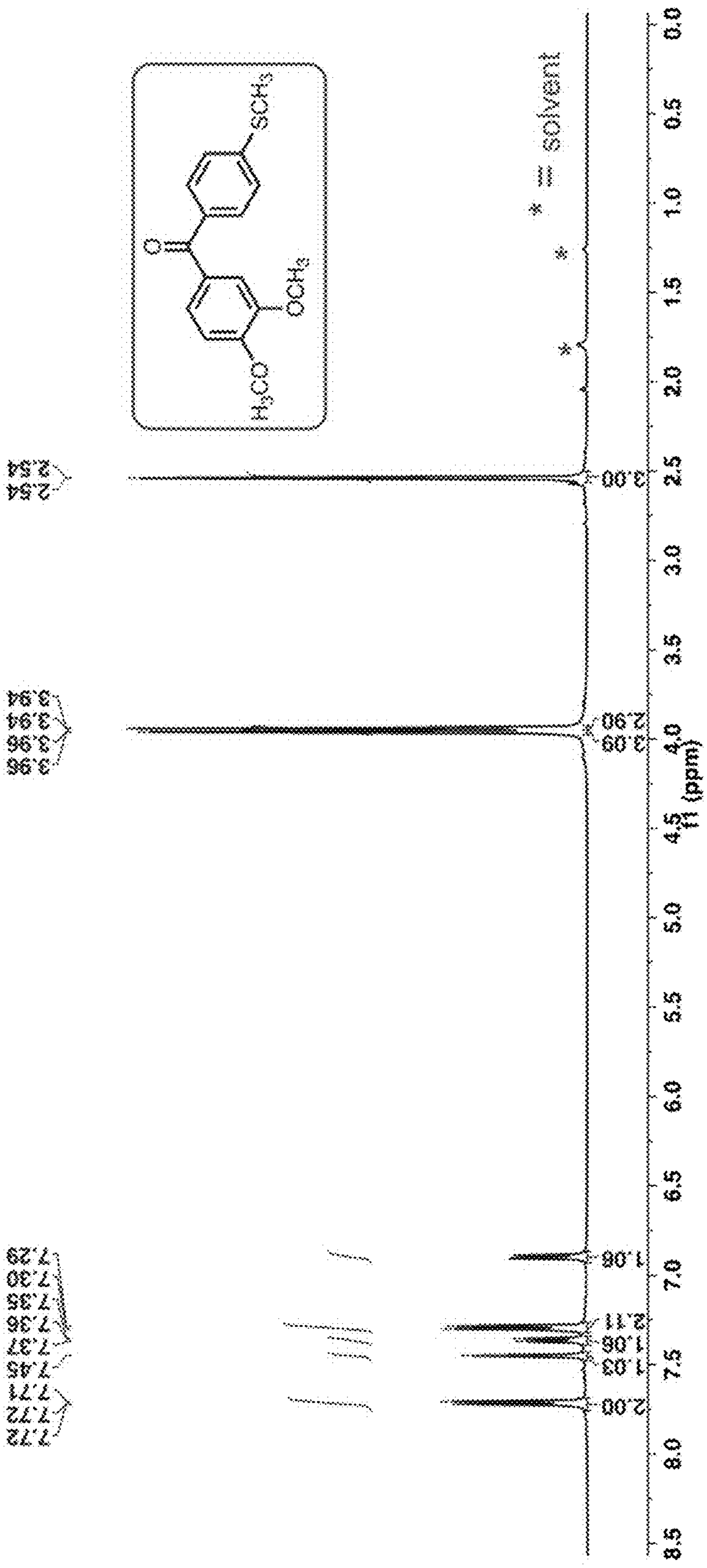
FIGS. 19A-19C: $^1H$ NMR spectrum (FIG. 19A), $^{13}C$ NMR spectrum (FIG. 19B), and HRMS-ESI spectrum (FIG. 19C) of 1d.
Figure 19B:
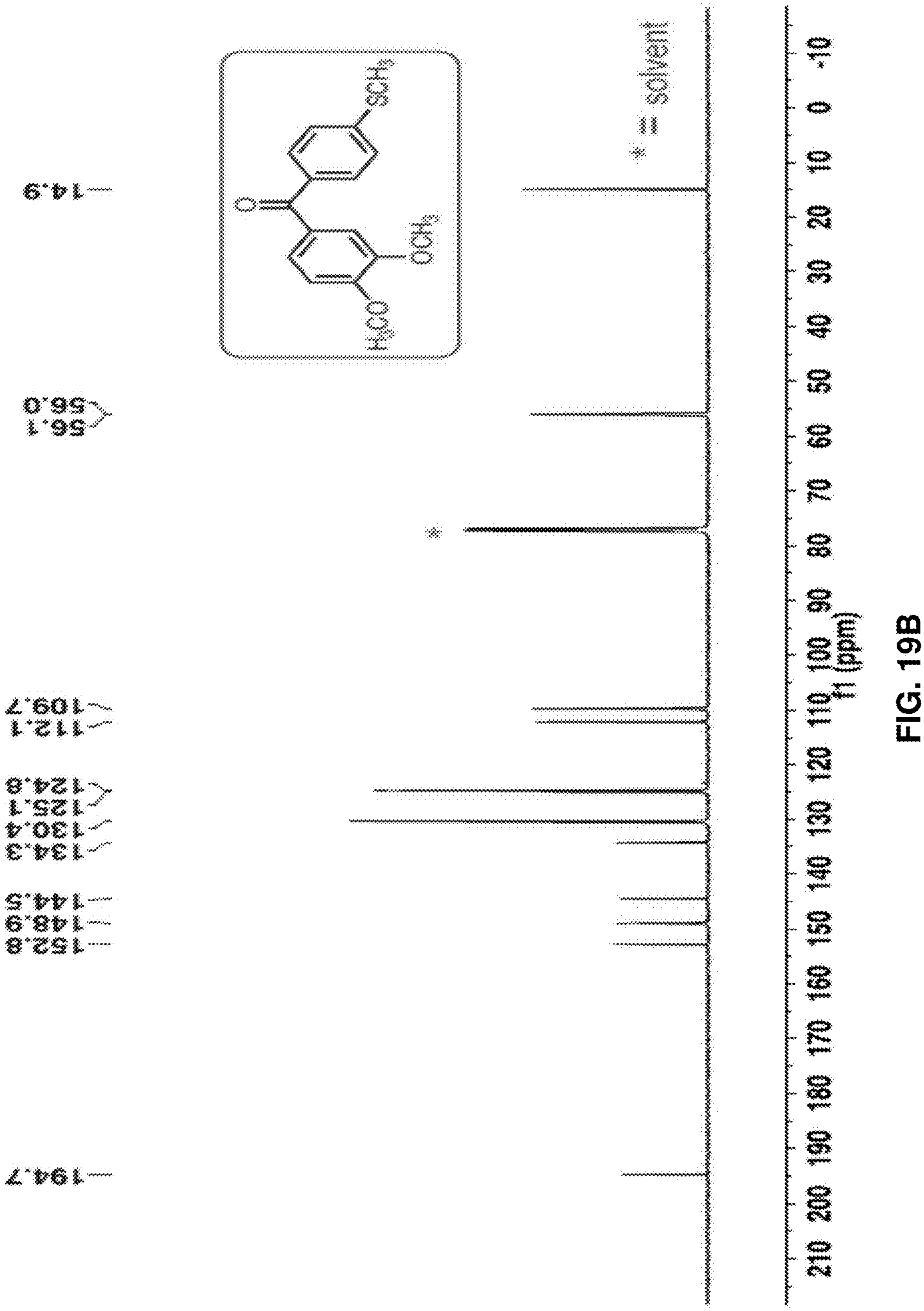
Figure 19C:
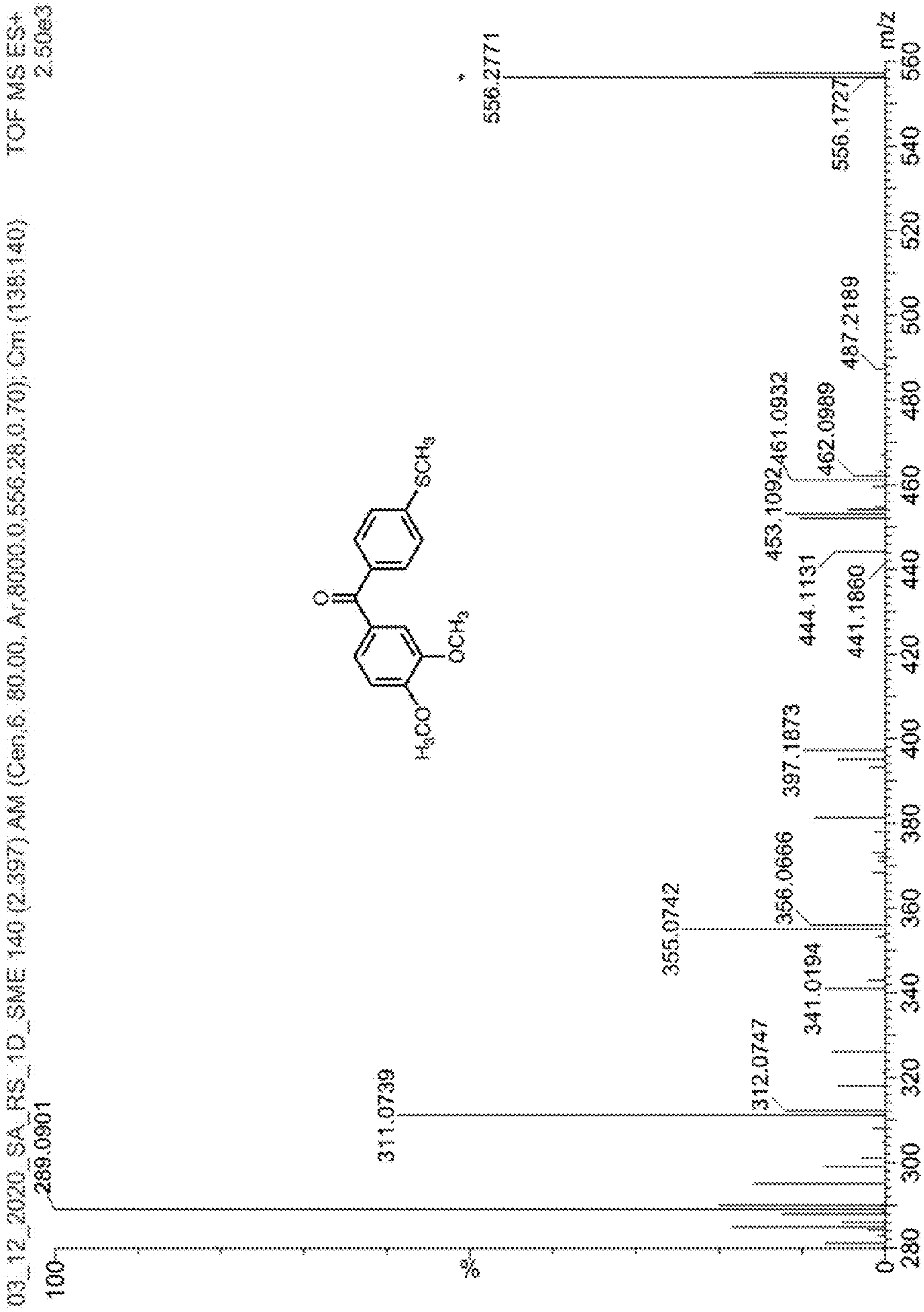

$R_f$=0.4 (70% hexanes: 30% ethyl acetate), Yield=95%. $^1$H NMR (500 MHz, $CDCl_3$, δ ppm) 7.75-7.66 (m, 2H), 7.45 (s, 1H), 7.40-7.33 (m, 1H), 7.29 (d, J=7.5 Hz, 2H), 6.90 (d, J=8.3 Hz, 1H), 3.96 (m, 3H), 3.94 (m, 3H), 2.54 (s, 3H). $^{13}$C NMR (125 MHz, $CDCl_3$, δ ppm) 196.9, 150.4, 146.6, 130.1, 124.0, 113.8, 109.7, 56.0, 26.2. Mass accuracy (m/z) ($[M+H]^+$:=[(289.0898-289.0901)/289.0898]*$10^6$=1.0 ppm. FIG. 19A shows the $^1$H NMR spectrum of 1d, FIG. 19B shows the $^{13}$C NMR spectrum of 1d, and FIG. 19C shows the HRMS-ESI spectrum of 1d.

1e

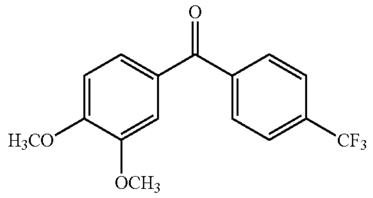

Figure 20A:
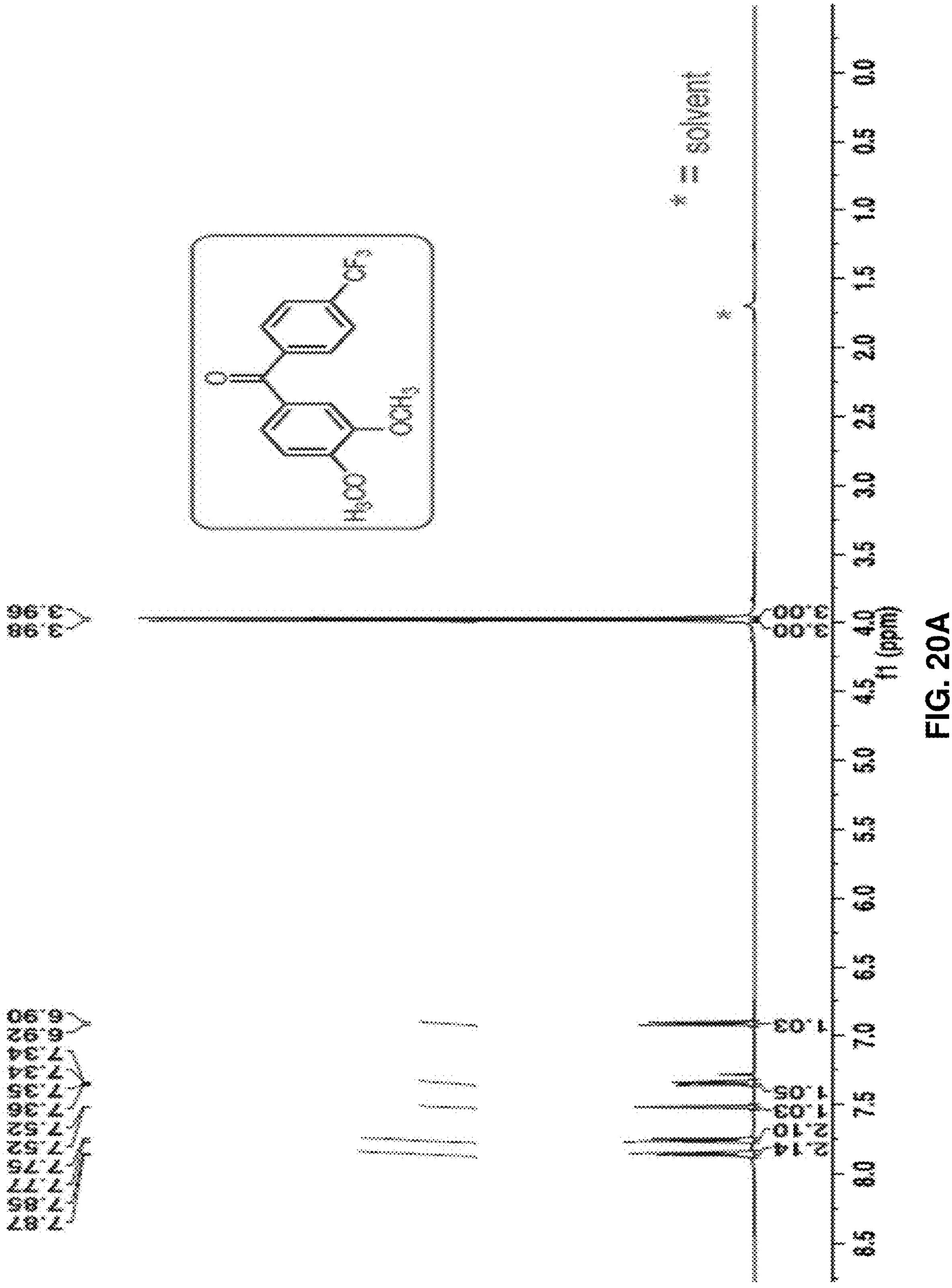
FIGS. 20A-20C: $^{1}H$ NMR spectrum (FIG. 20A), $^{13}C$ NMR spectrum (FIG. 20B), and HRMS-ESI spectrum (FIG. 20C) of 1e.
Figure 20B:
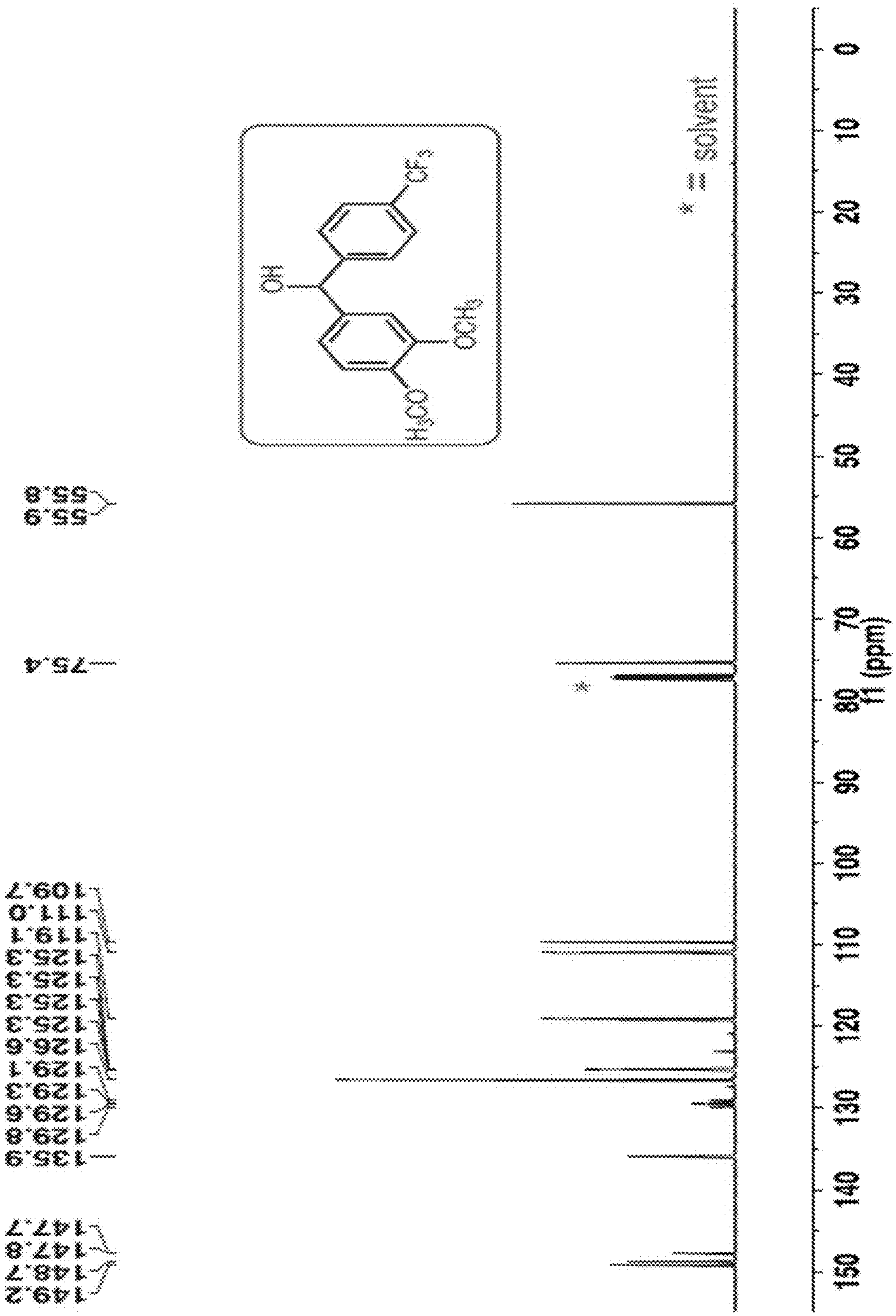
Figure 20C:
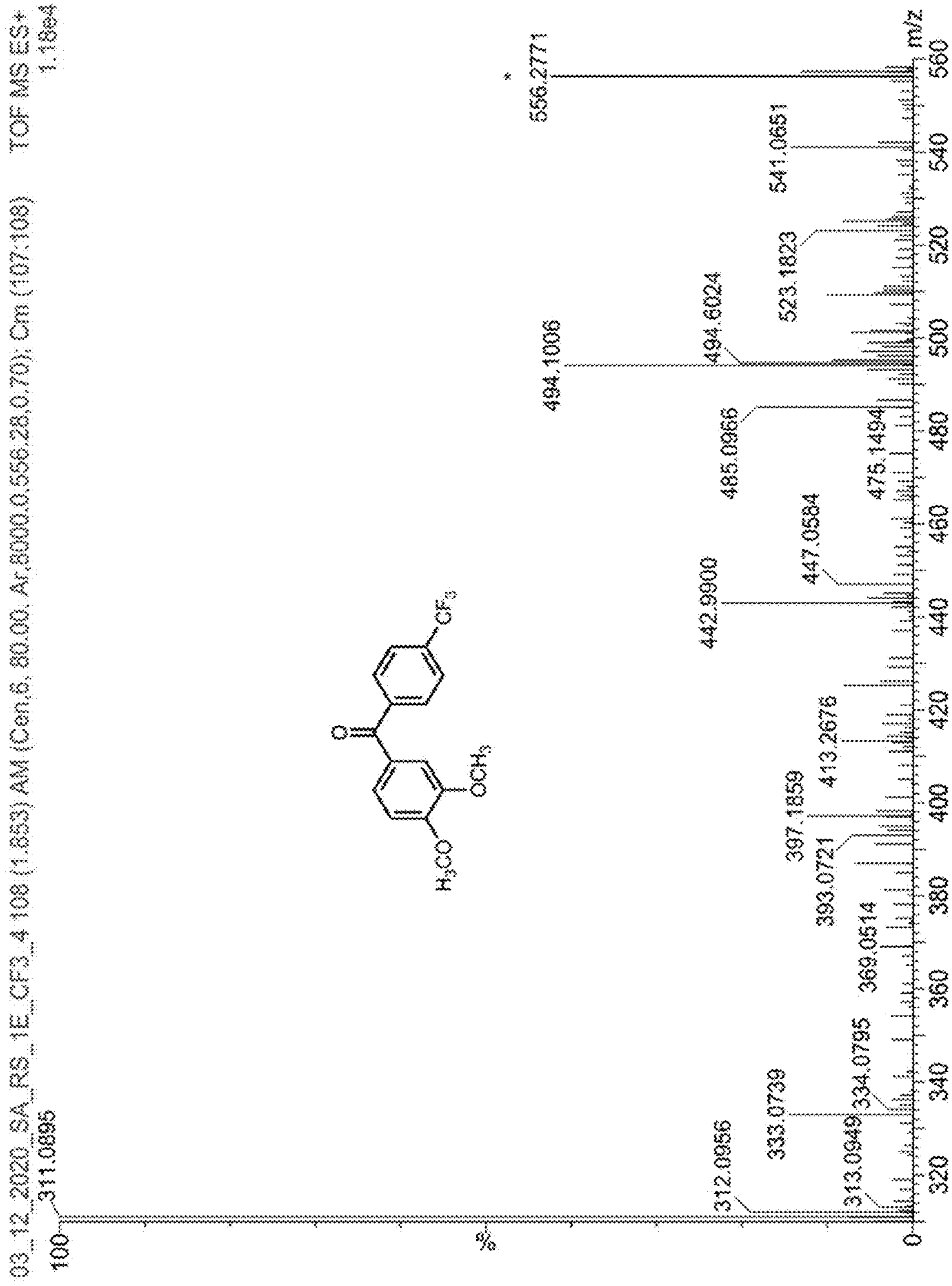

$R_f$=0.53 (70% hexanes: 30% ethyl acetate), Yield=92%. $^1$H NMR (500 MHz, $CDCl_3$, δ ppm) 7.86 (d, J=8.0 Hz, 2H), 7.76 (d, J=8.1 Hz, 2H), 7.52 (d, J=2.0 Hz, 1H), 7.35 (d, J=2.0 Hz, 1H), 6.91 (d, J=8.4 Hz, 1H), 3.98 (s, 3H), 3.96 (s, 3H). $^{13}$C NMR (125 MHz, $CDCl_3$, 6 ppm) 194.3, 153.5, 149.2, 141.5, 133.6, 133.3 (q, J=32.6 Hz), 133.1, 132.8, 129.7, 129.4, 125.7, 125.23 (q, J=3.7 Hz), 125.2, 125.2, 125.1, 124.8, 122.6, 111.8, 109.8, 56.1, 56.0. Mass accuracy (m/z) ($[M+H]^+$:=[(311.0895-311.0895)/311.0895]*$10^6$=0.0 ppm. FIG. 20A shows the $^1$H NMR spectrum of 1e, FIG. 20B shows the $^{13}$C NMR spectrum of 1e, and FIG. 20C shows the HRMS-ESI spectrum of 1e.

1f

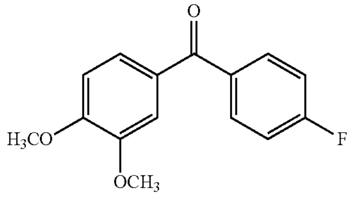

Figure 21A:
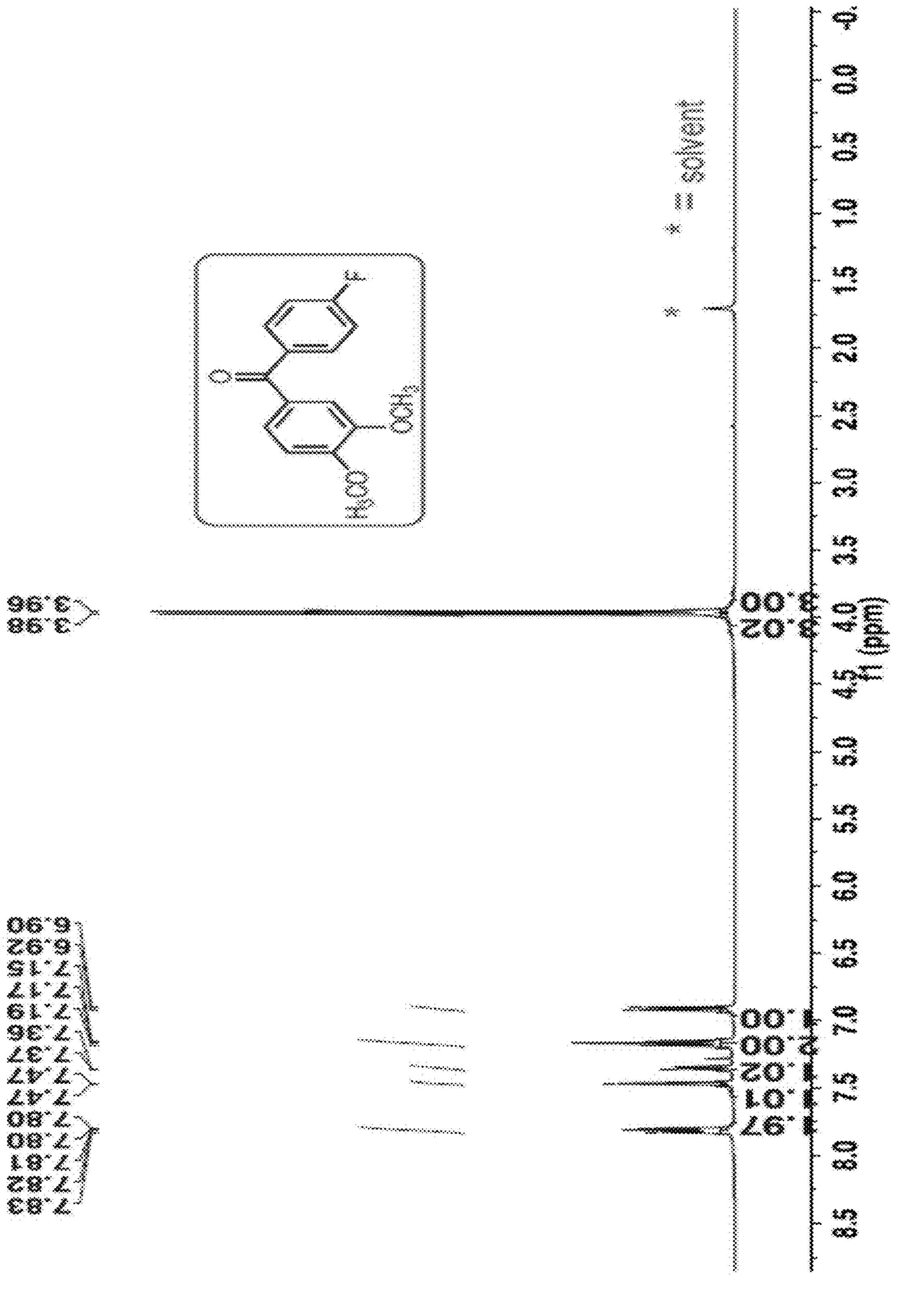
FIGS. 21A-21C: $^{1}H$ NMR spectrum (FIG. 21A), $^{13}C$ NMR spectrum (FIG. 21B), and HRMS-ESI spectrum (FIG. 21C) of 1f.
Figure 21B:
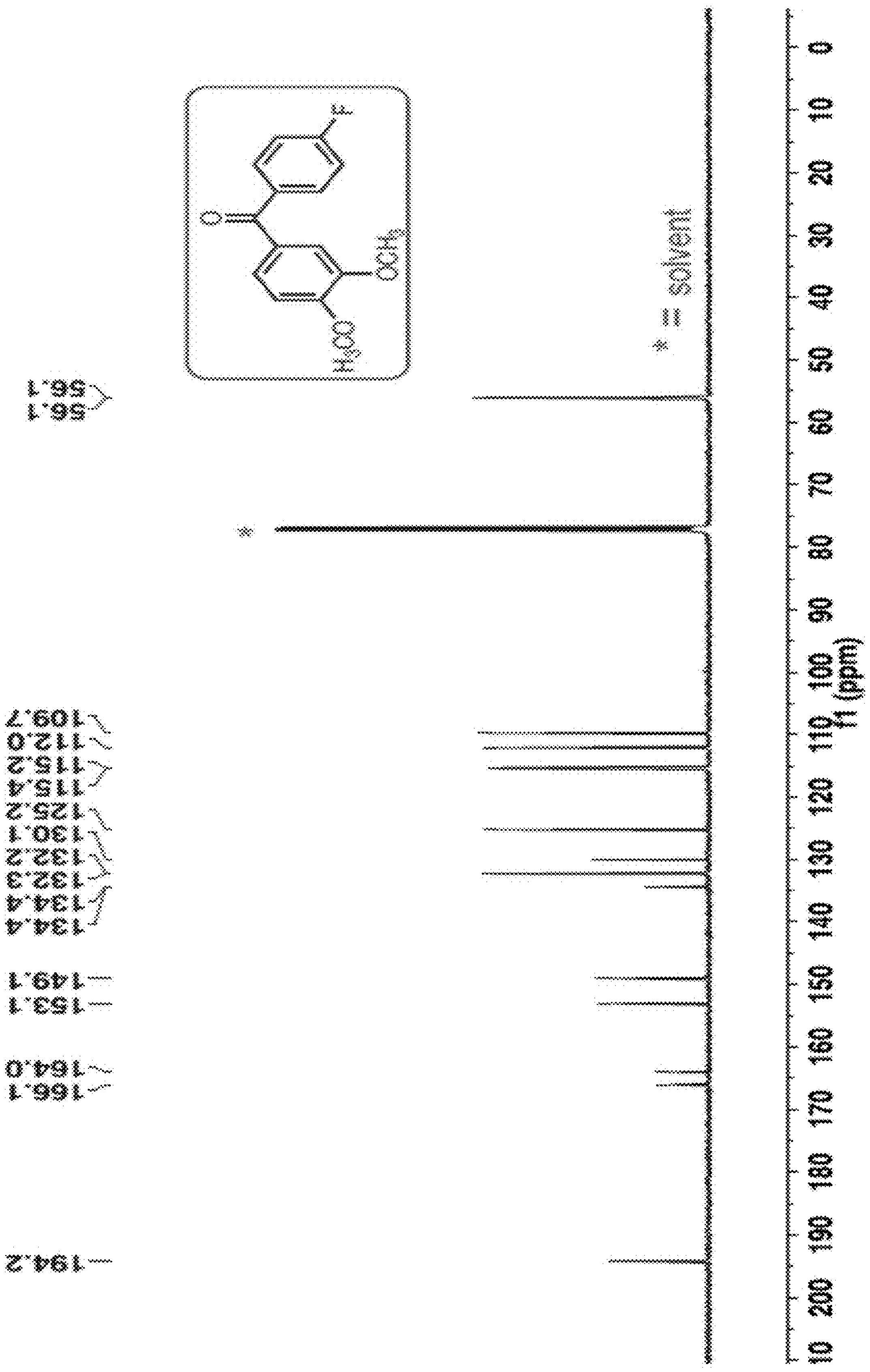
Figure 21C:
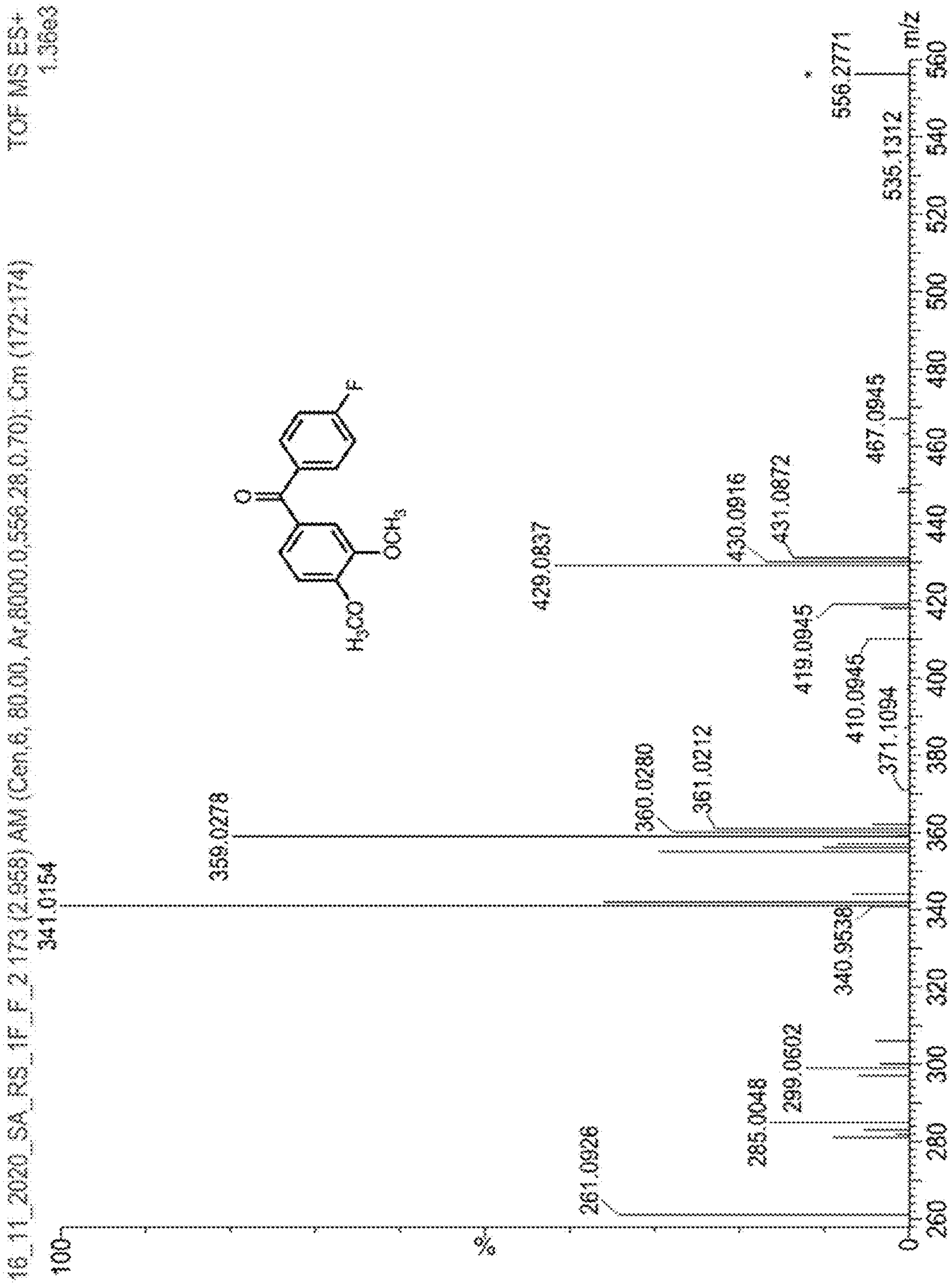

$R_f$=0.46 (70% hexanes: 30% ethyl acetate), Yield=89%. $^1$H NMR (500 MHz, $CDCl_3$, δ ppm) 7.83-7.79 (m, 2H), 7.47 (d, J=1.7 Hz, 1H), 7.36 (d, J=1.8 Hz, 1H), 7.17 (t, J=8.6 Hz, 2H), 6.91 (d, J=8.3 Hz, 1H), 3.98 (s, 3H), 3.96 (s, 3H). $^{13}$C NMR (125 MHz, $CDCl_3$, δ ppm) 195.61, 153.01, 148.99, 138.27, 131.90, 130.19, 129.73, 128.18, 125.53, 112.07, 109.71, 56.11, 56.06. Mass accuracy (m/z) ($[M+H]^+$:=[(261.0926-261.0926)/261.0926]*$10^6$=0.0 ppm. FIG. 21A shows the $^1$H NMR spectrum of 1f, FIG. 21B shows the $^{13}$C NMR spectrum of 1f, and FIG. 21C shows the HRMS-ESI spectrum of 1f.

Synthesis of Furfuryl Methacrylate Monomer 5

Figure 22:
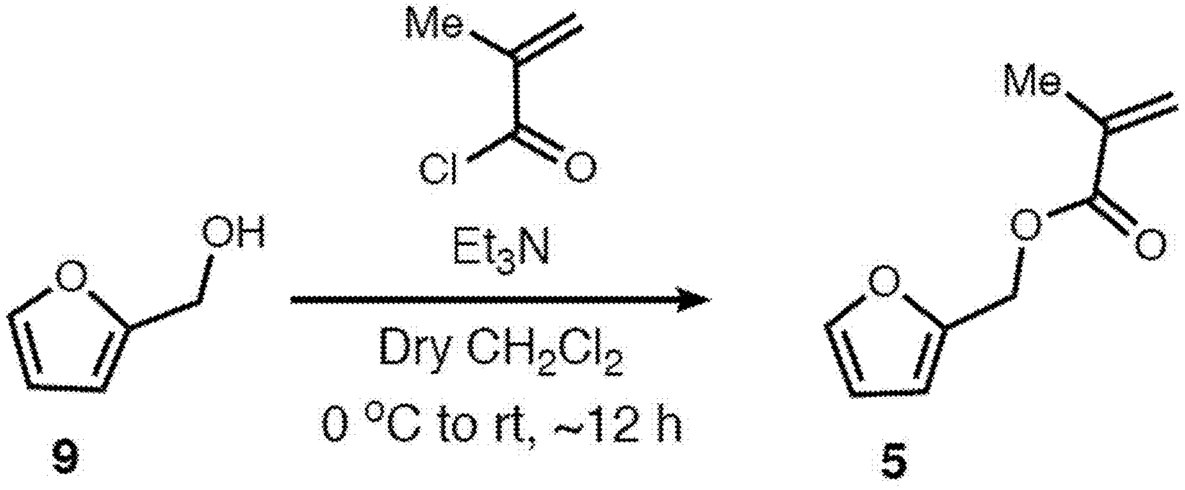
FIG. 22: Scheme 6, depicting the synthesis of furfuryl methacrylate monomer 5.

FIG. 22 shows the synthesis of furfuryl methacrylate monomer 5.

Furfuryl alcohol 9 (4g, 1 equiv, 40 mmol) was dissolved in 100 mL dry $CH_2Cl_2$ and cooled on an ice bath. Triethylamine (8.5 mL, 60 mmol) was added dropwise to the stirred solution at 0° C. for an ~1 h. Methacryloyl chloride (5.9 mL, 60 mmol) was added to the reaction mixture and stirred for another ~1 h and reaction was slowly warmed to room temperature for ~12 h. After the reaction, the solution was filtered to remove amine salts. The filterate was washed 3×20 mL of water and 10 mL of brine. The organic layer collected was dried over sodium sulfate and concentrated under reduced pressure to get the crude product. The crude product was purified by column chromatography with Hex: EA (10:1) to give oily product 5.

5

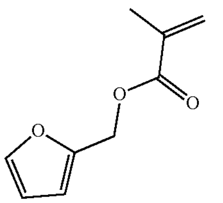

Figure 23A:
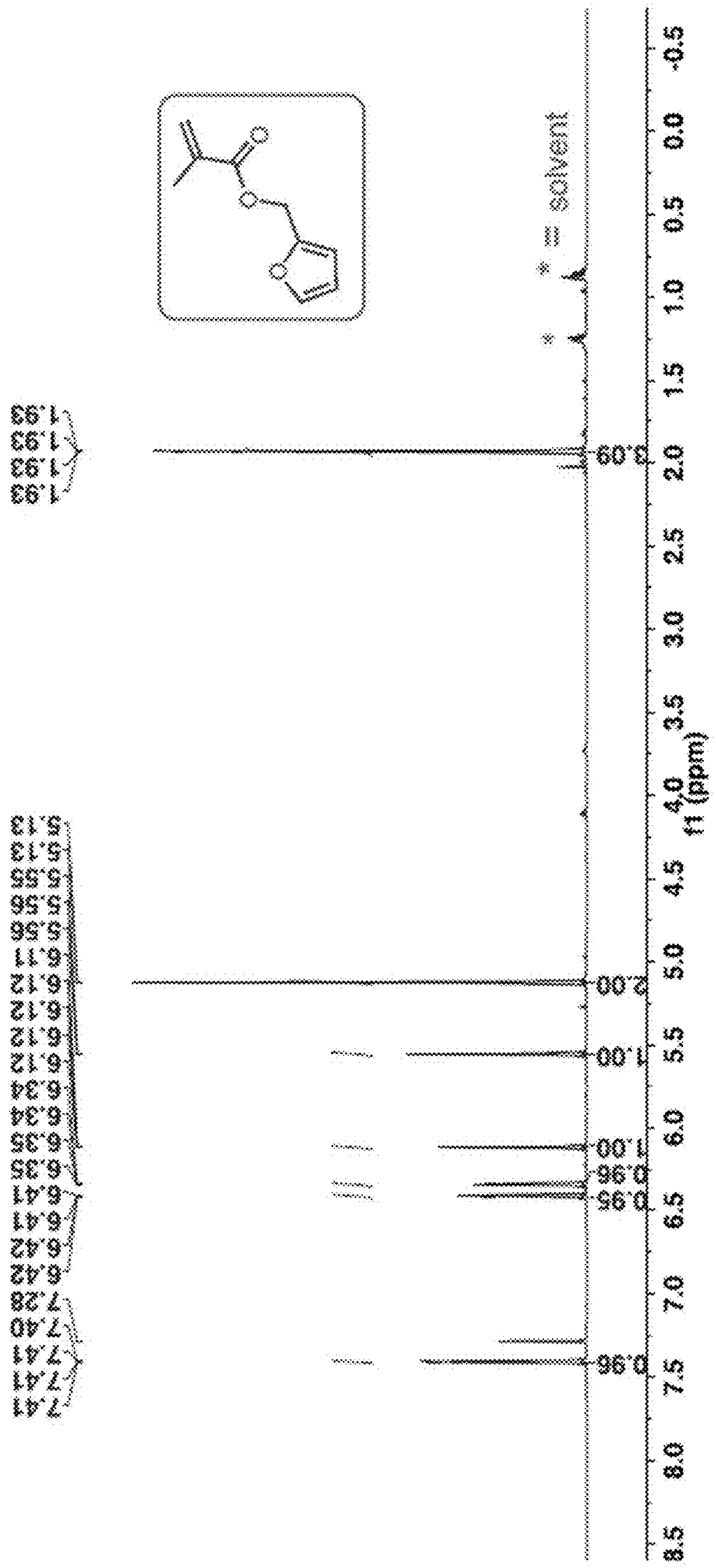
FIGS. 23A-23B: $^{1}H$ NMR spectrum (FIG. 23A) and $^{13}C$ NMR spectrum (FIG. 23B) of 5.
Figure 23B:
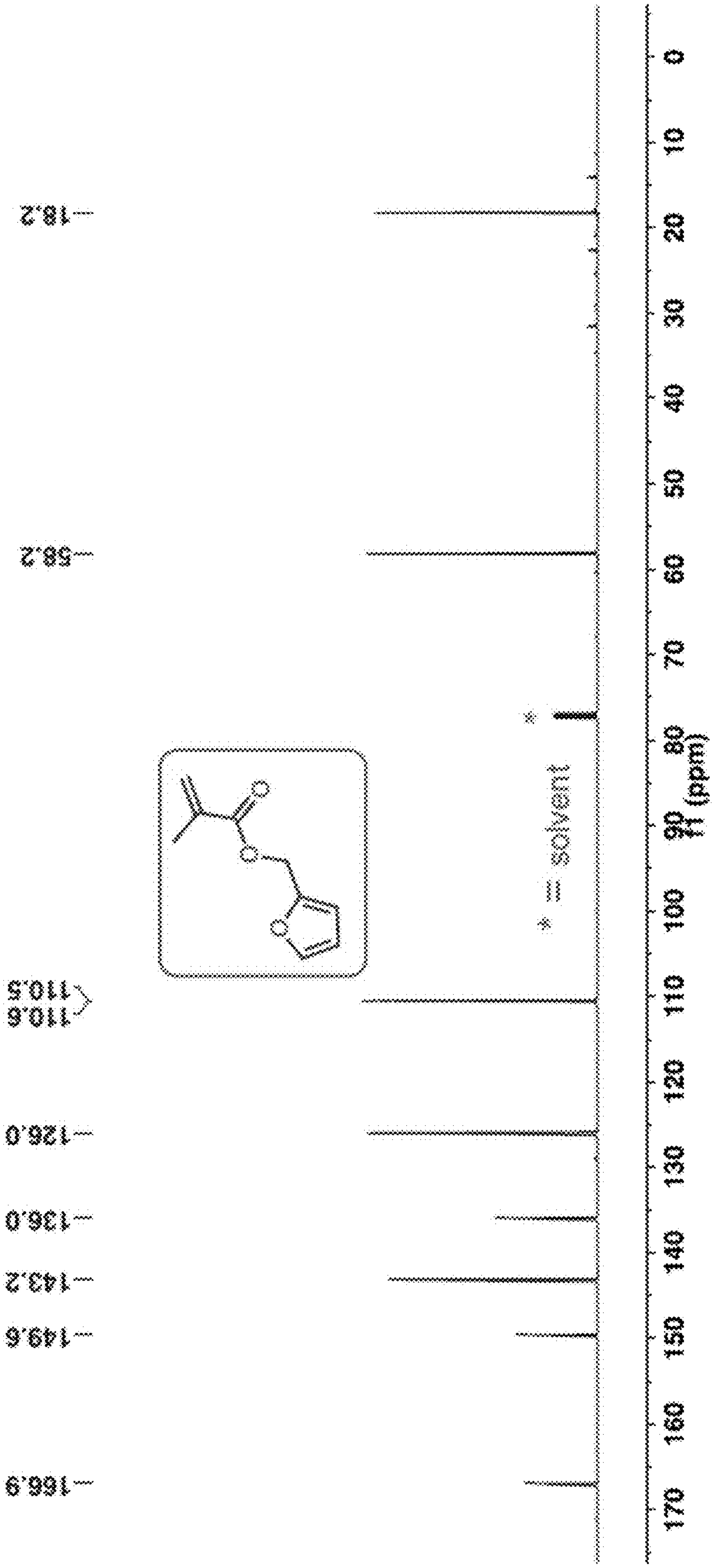

$R_f$=0.38 (85% hexanes: 15% ethyl acetate), Yield=68%. $^1$H NMR (500 MHz, $CDCl_3$, δ ppm) 7.41 (dd, J=1.9, 0.8 Hz, 1H), 6.4-6.38 (m, 1H), 6.35 (dd, J=3.2, 1.9 Hz, 1H), 6.12 (dt, J=1.9, 0.9 Hz, 1H), 5.58-5.52 (m, 1H), 5.13 (s, 2H), 1.93 (dd, J=1.6, 1.1 Hz, 3H). $^{13}$C NMR (125 MHz, $CDCl_3$, δ ppm) 166.9, 149.6, 143.2, 136.0 126.0, 110.5, 110.5, 58.2, 18.2. FIG. 23A shows the $^1$H NMR spectrum of 5, and FIG. 23B shows the $^{13}$C NMR spectrum of 5.

Synthesis of 2,5-bis(hydroxymethyl)furan 12

Figure 24:
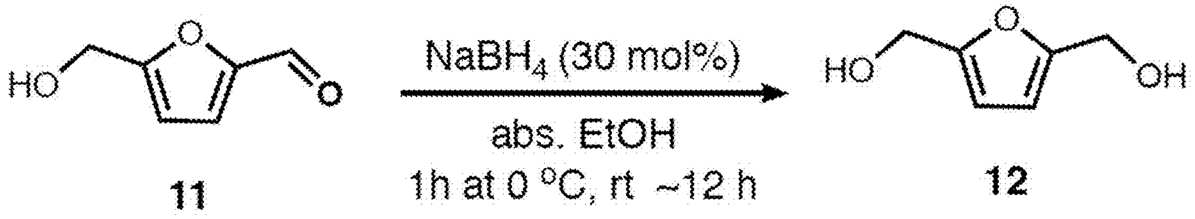
FIG. 24: Scheme 7, depicting the synthesis of 2,5-bis (hydroxymethyl) furan 12.

FIG. 24 shows the synthesis of 2,5-bis(hydroxymethyl) furan 12.

To a 250 mL round bottom flask with magnetic stir bar, 5-hydroxymethylfurfural (5.0 g, 39.6 mmol, 1 equiv) was added and dissolved in 5 mL of absolute ethanol and the mixture was stirred on an ice bath. To the cooled solution, sodium borohydride (0.46 g, 12 mmol, 30 mol %) was added slowly with constant stirring. The reaction mixture was allowed to stir on ice bath for an hour and then slowly warmed it to room temperature and continued stirring for 12 h. The reaction was quenched with 5 g of silica gel and the solvent was removed under reduced pressure. The solid slurry obtained was used for column chromatography using dichloromethane/methanol as mobile phase. A 225 nm detection was selected in the instrument for 2,5-dialkylsubstituted furan ring. Purification gave yellow viscous liquid which turned in to white powder material upon addition of diethyl ether.

12

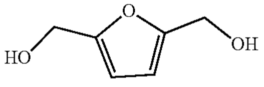

Figure 25A:
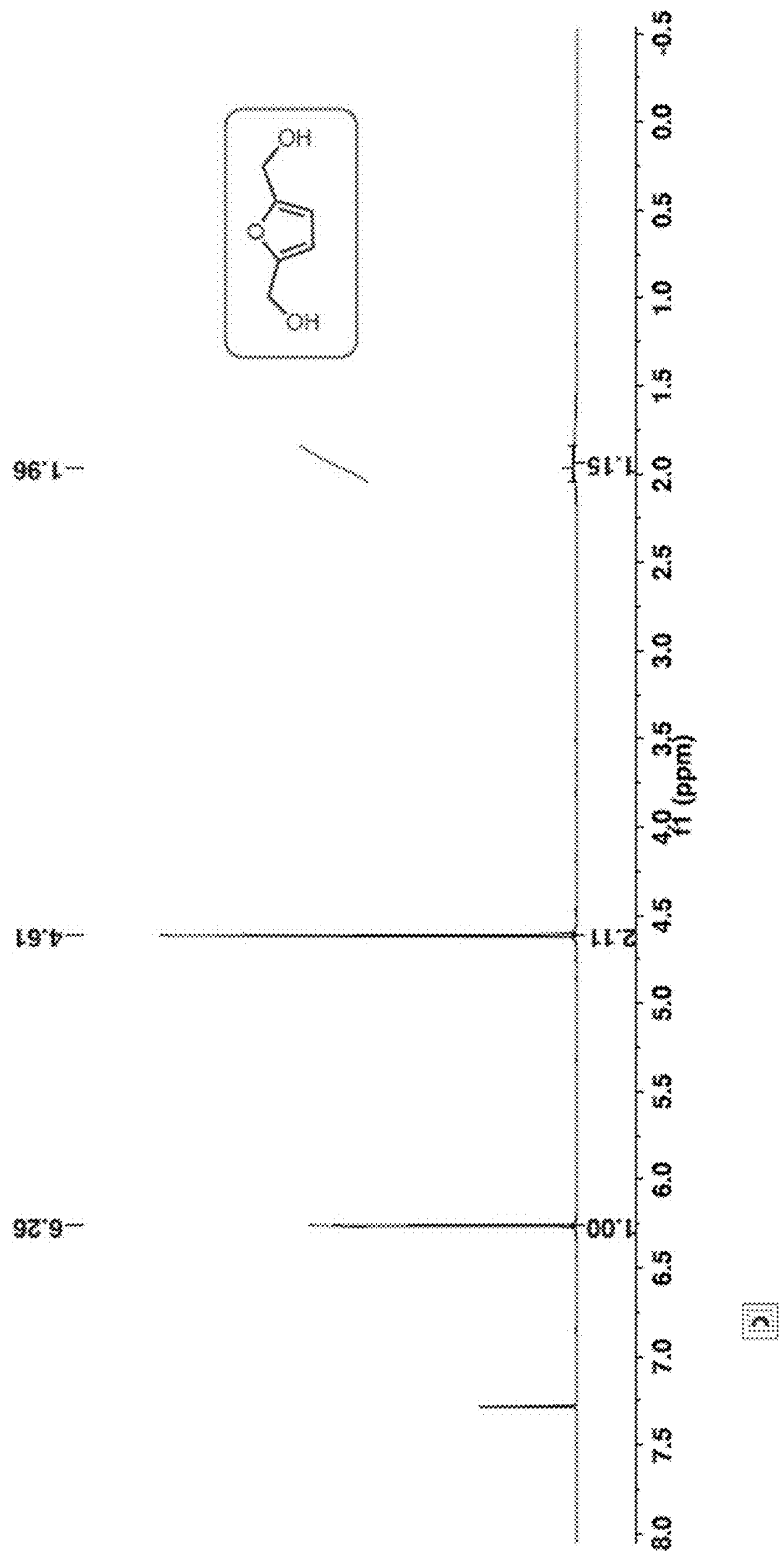
FIGS. 25A-25B: $^{1}H$ NMR spectrum (FIG. 25A) and $^{13}C$ NMR spectrum (FIG. 25B) of 12.
Figure 25B:
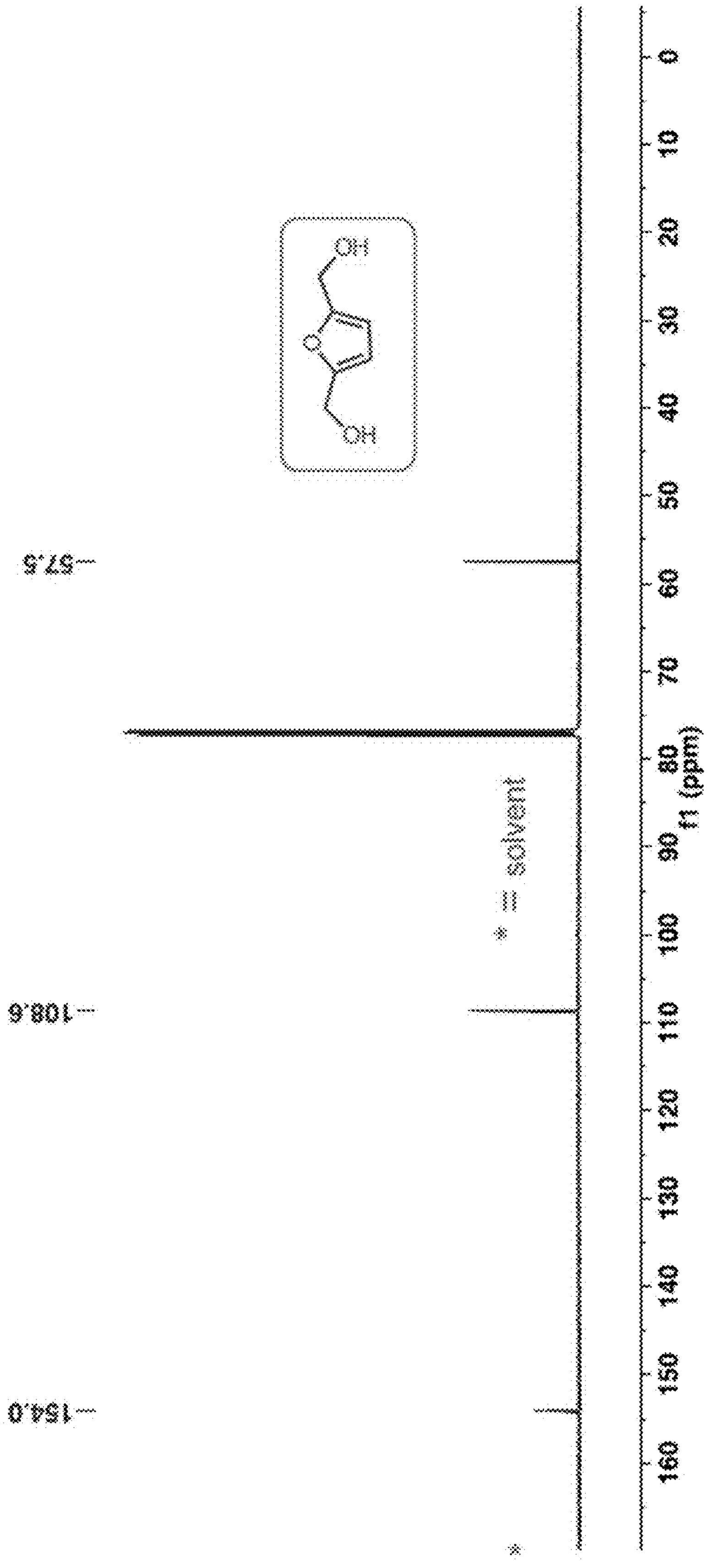

$R_f$=0.36 (95% Dichloromethane: 5% Methanol), Yield=82%. $^1$H NMR (500 MHz, $CDCl_3$, δ ppm) 6.26 (s, 1H), 4.61 (s, 2H), 1.96 (s, 1H). 13C NMR (125 MHz, $CDCl_3$, δ ppm) 154.0, 108.6, 57.5. FIG. 25A shows the $^1$H NMR spectrum of 12, and FIG. 25B shows the $^{13}$C NMR spectrum of 12.

Synthesis of Furfuryl Dimethacrylate Monomer 7

Figure 26:
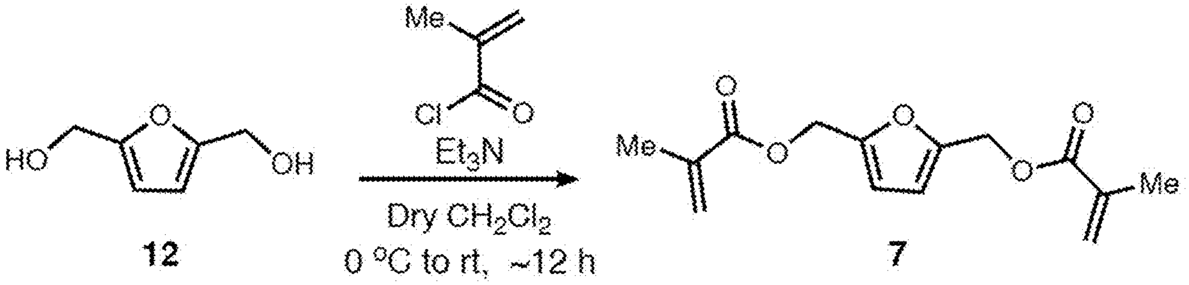
FIG. 26: Scheme 8, depicting the synthesis of furfuryl dimethacrylate monomer 7.

FIG. 26 depicts the synthesis of furfuryl dimethacrylate monomer 7.

Furfural diol derivative 12 (4g, 1 equiv, 40 mmol) was dissolved in 100 mL dry $CH_2Cl_2$ and cooled over an ice bath. Triethylamine (8.5 mL, 60 mmol) was added dropwise to the stirred solution at 0° C. for an ~1 h. Methacryloyl chloride (5.9 mL, 60 mmol) was added to the reaction mixture and stirred for another ~1 h and reaction was slowly warmed to room temperature for ~12 h. After the reaction, the solution was filtered to remove amine salts. The filterate was washed 3×20 ml of water and 10 mL of brine. The organic layer collected was dried over sodium sulfate and concentrated under reduced pressure to get the crude product. The crude product was purified by column chromatography with Hex: EA (10:1) to give oily product 7.

7

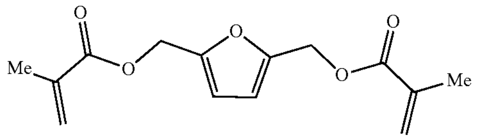

Figure 27A:
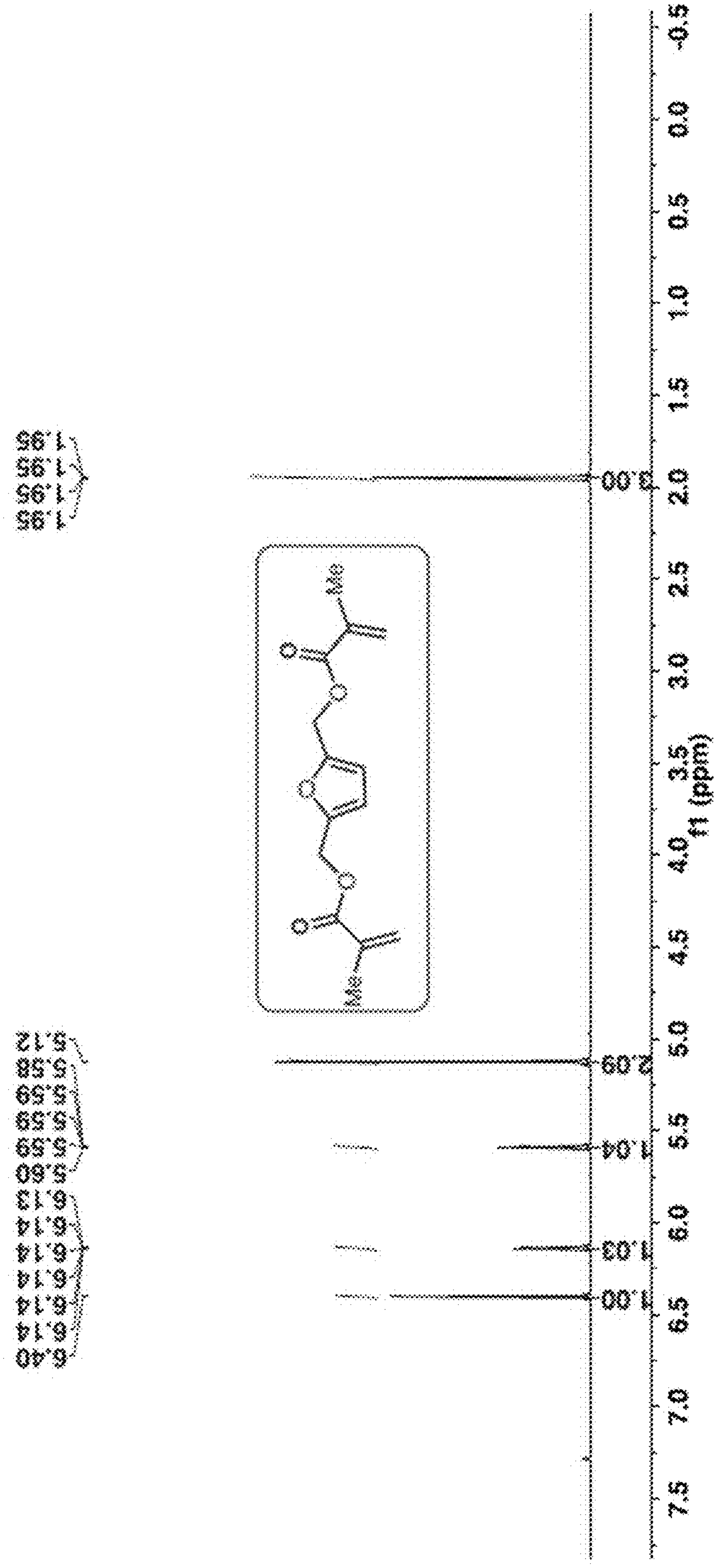
FIGS. 27A-27B: $^{1}H$ NMR spectrum (FIG. 25A) and $^{13}C$ NMR spectrum (FIG. 25B) of 7.
Figure 27B:
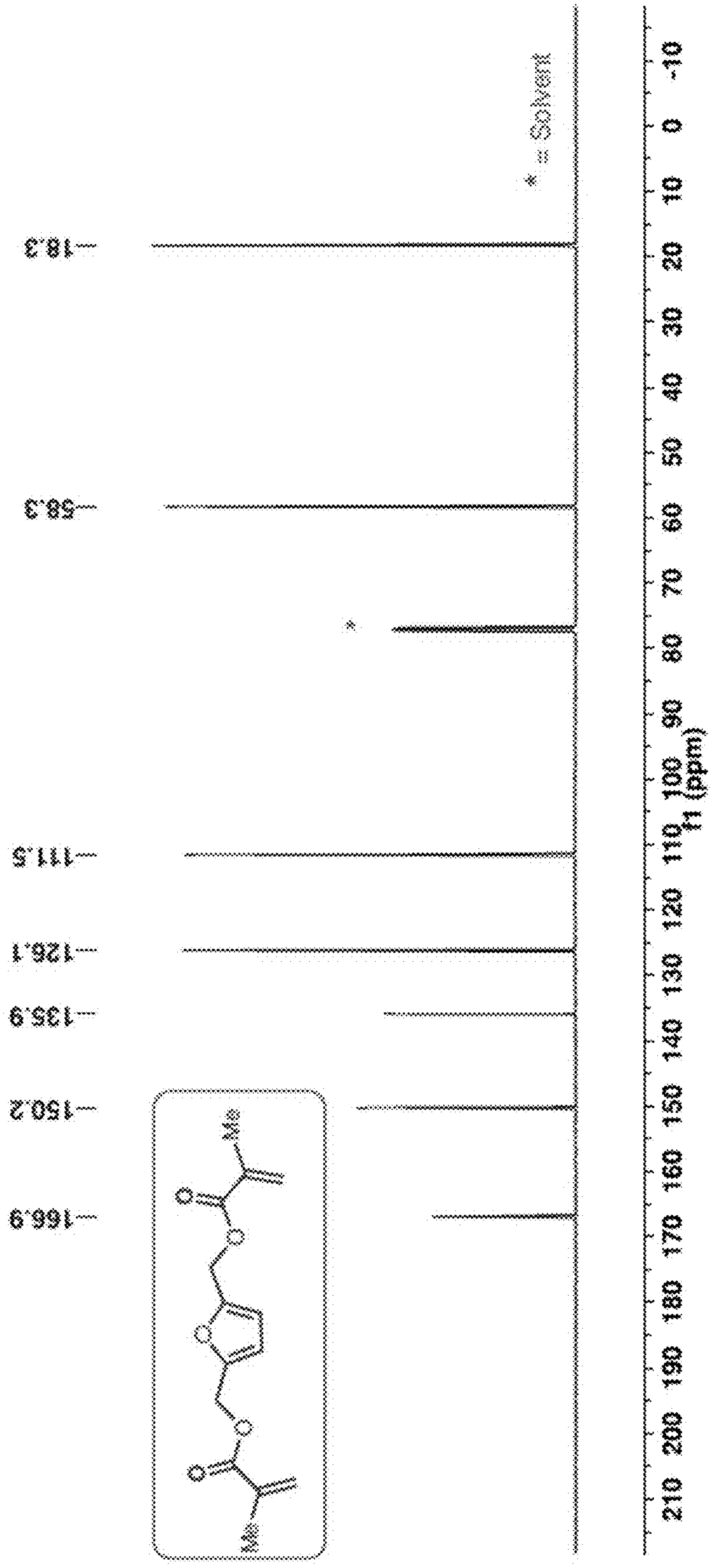

$R_f$=0.4 (85% hexanes: 15% ethyl acetate), Yield=60%. $^1$H NMR (500 MHz, $CDCl_3$, δ ppm) 6.40 (s, 1H), 6.14 (dq, J=1.9, 0.9 Hz, 1H), 5.59 (p, J=1.6 Hz, 1H), 5.12 (s, 2H), 1.95 (dd, J=1.6, 1.0 Hz, 3H). $^{13}$C NMR (126 MHz, $CDCl_3$, δ ppm) 166.9, 150.2, 135.9, 126.1, 111.5, 58.3, 18.3. FIG. 27A shows the $^1$H NMR spectrum of 7, and FIG. 27B shows the $^{13}$C NMR spectrum of 7.

Photophysical Studies

Figure 28A:
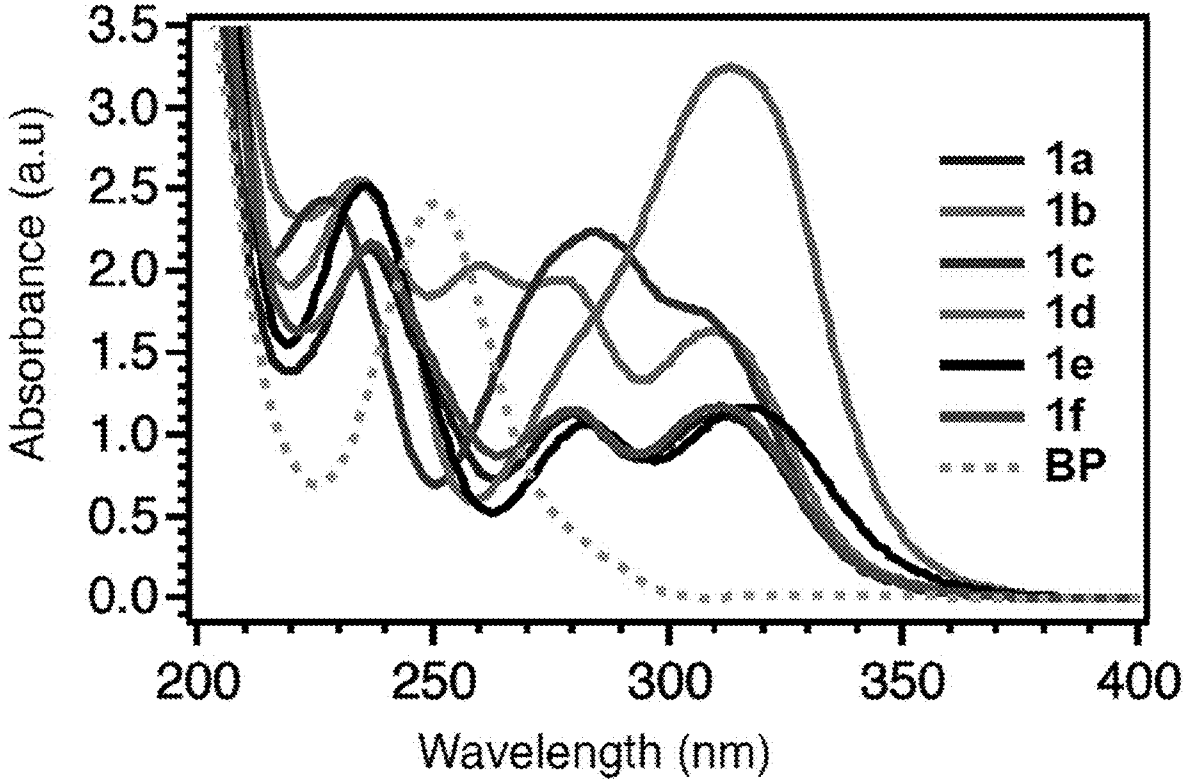
FIGS. 28A-28B: Absorption spectra of photoinitiators 1a-1f and benzophenone (BP) at a concentration of 150 μM in MeCN (FIG. 28A), and absorption spectra of photoinitiators 1a-1f and BP in MeCN with matching optical densities of ~390 nm (FIG. 28B).
Figure 28B:
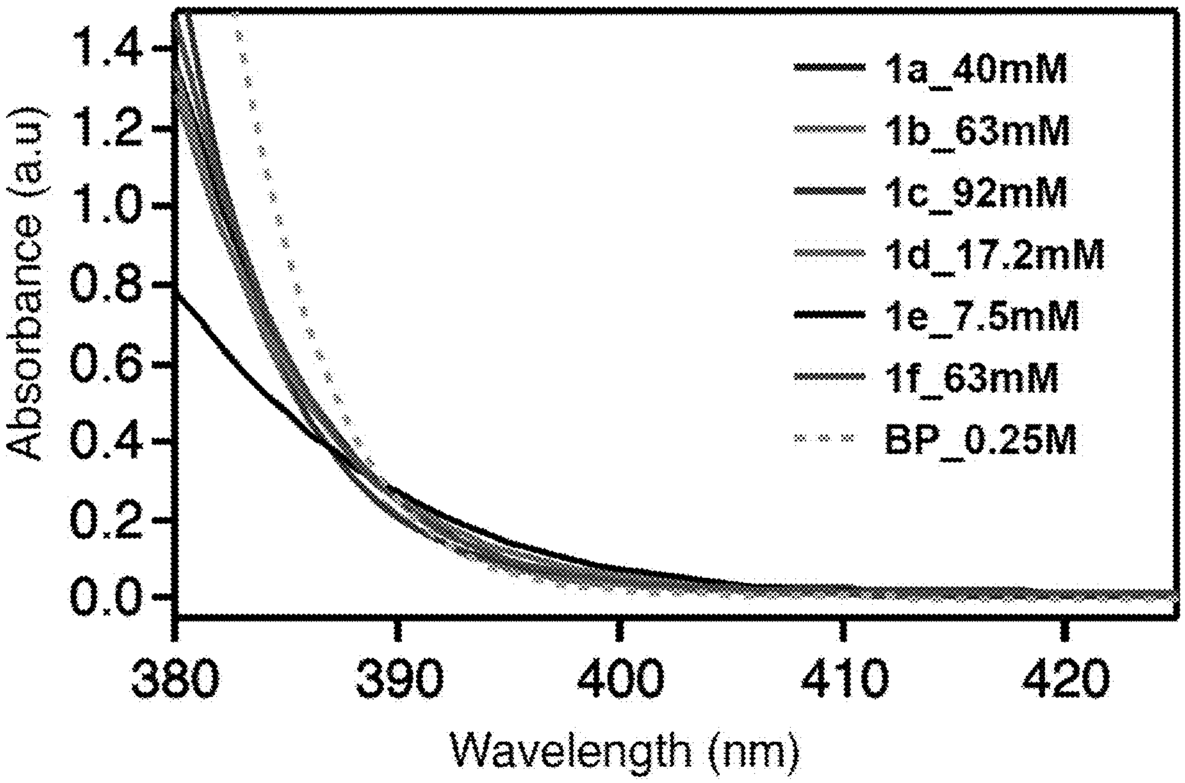

FIGS. 28A-28B show the UV-Vis absorption spectra for benzophenone photoinitiators 1a-1f and BP in MeCN.

Figure 29:
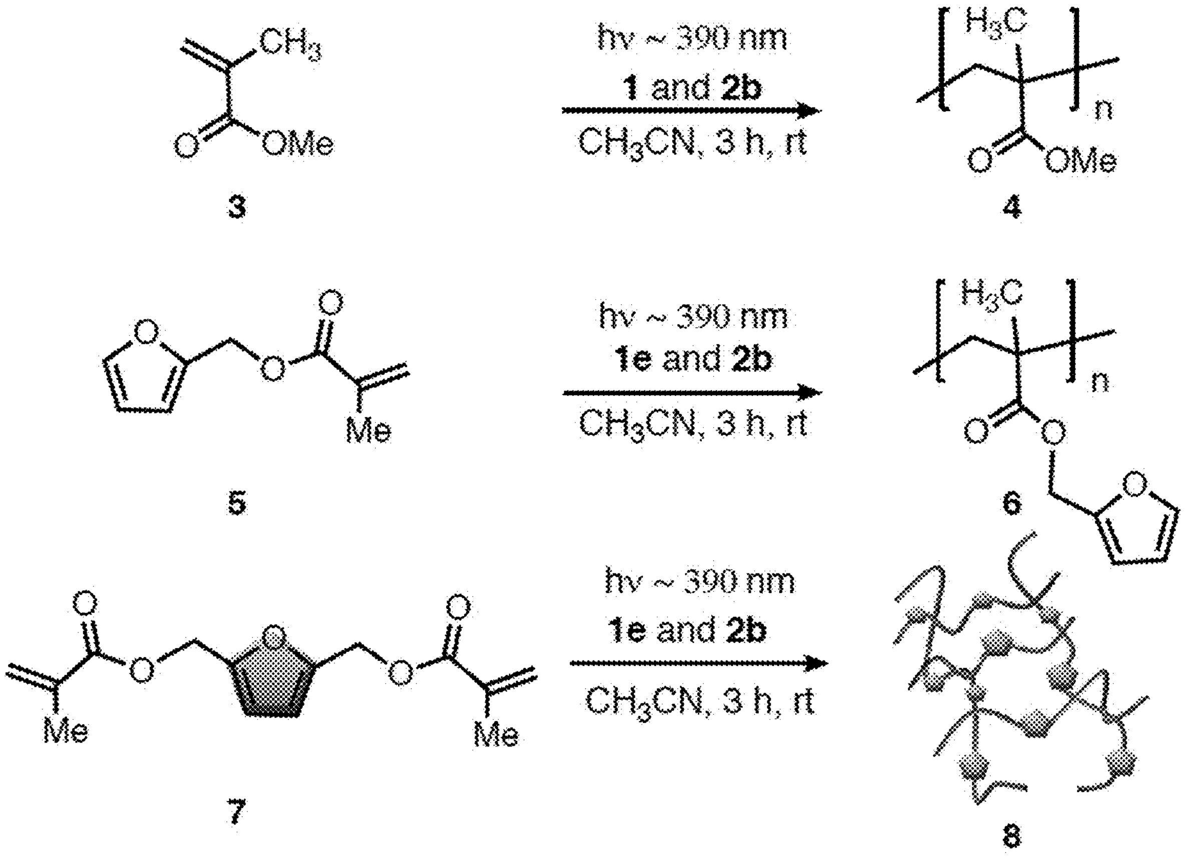
FIG. 29: Photopolymerization of methacrylate derivates 3, 5, and 7.

Photopolymerization of Methacrylate Derivatives Using Biobased Benzophenone Derivatives Under Visible Light Irradiation FIG. 29 depicts the photopolymerization of methacrylate derivates 3, 5, and 7.

Methylmethacrylate monomer 3 was freshly distilled, whereas furan derivatives 5 and 7 were synthesized and stored under argon atmosphere prior to the use. Photopolymerization of 3 was carried out with photoinitiators 1a-1g and BP and co initiators 2a-2c in MeCN with appropriate concentrations (as mentioned in the Tables 1-3). Furfuryl methacrylate derivative 5 and dimethacrylate derivative 7 was polymerized with photoinitiator/co-initiator system 1e/2b and 1e/2d. A solution of photoinitiator 1 and co-initiator 2 and monomers (3/5/7) in MeCN was degassed with N2 for 15 min in a septum sealed pyrex test tube and the resulting solution was irradiated in a purple LED strip illumination with a flux density of 1.5 mW/cm$^2$ (LED jar) and 11.8 to 51.1 mW/cm$^2$ (Kessil LED PR160 390 nm with 4 levels of intensity). Ee=Flux density (mW/cm2) measured by Thor PM100D power meter console using S121C photodiode power sensor by keeping the sample at a distance of ~2 cm from the light source. The total volume of the polymerization reaction mixture was 3 mL (1 mL of monomer, 1 mL of photoinitiator and 1 mL of co-initiator).

Gravimetric Analysis for % Conversion of Monomers

After the photoirradiation, 30 mL of cold methanol was added to each of the reaction mixture, the turbid polymers were separated by Buchner funnel vacuum filtration. Polymers was placed in an empty vial (known weight and dried in vacuum oven at 45° C. for ~24 h until constant weight is achieved. The dry mass of the polymer was weighed, and the polymer conversion is determined by =[weight of the polymer (g)/initial weight of the monomer(g)]*100.

Gel Permeation Chromatography (GPC) Analysis for Acrylate Polymers

Concentration of polymer samples for GPC analysis: 1 mg/ml in THF and soaked the samples overnight. The saturated compounds were filtered through 25 mm, 0.2 μm PTFE membrane filters.

TABLE 3

Biobased photoinitiators for methylmethacrylate polymerization under visible light illumination

| Entry | PI | CI | Monomer[a] | % Conversion [b] | Mn | MW | PDI |
|---|---|---|---|---|---|---|---|
| 1 | 1a | 2a | 3 | 4.2 | 70,252 | 135,409 | 1.9 |
| 2 | 1a | 2b | 3 | 10.6 | 33,383 | 47,150 | 1.4 |

TABLE 3-continued

Biobased photoinitiators for methylmethacrylate polymerization under visible light illumination

| Entry | PI | CI | Monomer[a] | % Conversion [b] | Mn | MW | PDI |
|---|---|---|---|---|---|---|---|
| 3 | 1a | 2c | 3 | 7.4 | 20,054 | 27,568 | 1.4 |
| 4 | 1b | 2b | 3 | 7.6 | 41,520 | 68,026 | 1.6 |
| 5 | 1c | 2b | 3 | 6.6 | 61,862 | 115,867 | 1.8 |
| 6 | 1d | 2b | 3 | 15.6 | 23,869 | 36,707 | 1.5 |
| 7 | 1e | 2b | 3 | 16.8 | 25,562 | 39,114 | 1.5 |
| 8 | 1f | 2b | 3 | 10.9 | 36,328 | 55,283 | 1.5 |
| 9 | BP | 2b | 3 | 2.7 | 106,614 | 195,602 | 1.8 |
| 10 | 1e | 2b | 5 | 21 | 62,457 | 152,858 | 2.4 |
| 11 | 1e | 2b | 7 | 78 | U/I | U/I | —[c] |

[a]M = Monomer; PI = Photoinitiator; CI = co-initiator. [PI] = 5 mM, [CI] = 5 mM, [monomer] = 3.12M, solvent = $CH_3CN$. Photopolymerizations were carried out with a purple LED strip illumination with a flux density of 1.5 mW/$cm^2$. Ee = Flux density (mW/$cm^2$) measured by Newport/spectra physics 407A Portable Laser Power Meter by keeping the sample at a distance of ~2 cm from the light source. Irradiation was done for 3 h.

[b] Conversions determined by gravimetric analysis and carry an error of 3%. The values reported are an average of three runs.

[c]Crossed linked polymer.

Figure 30A:
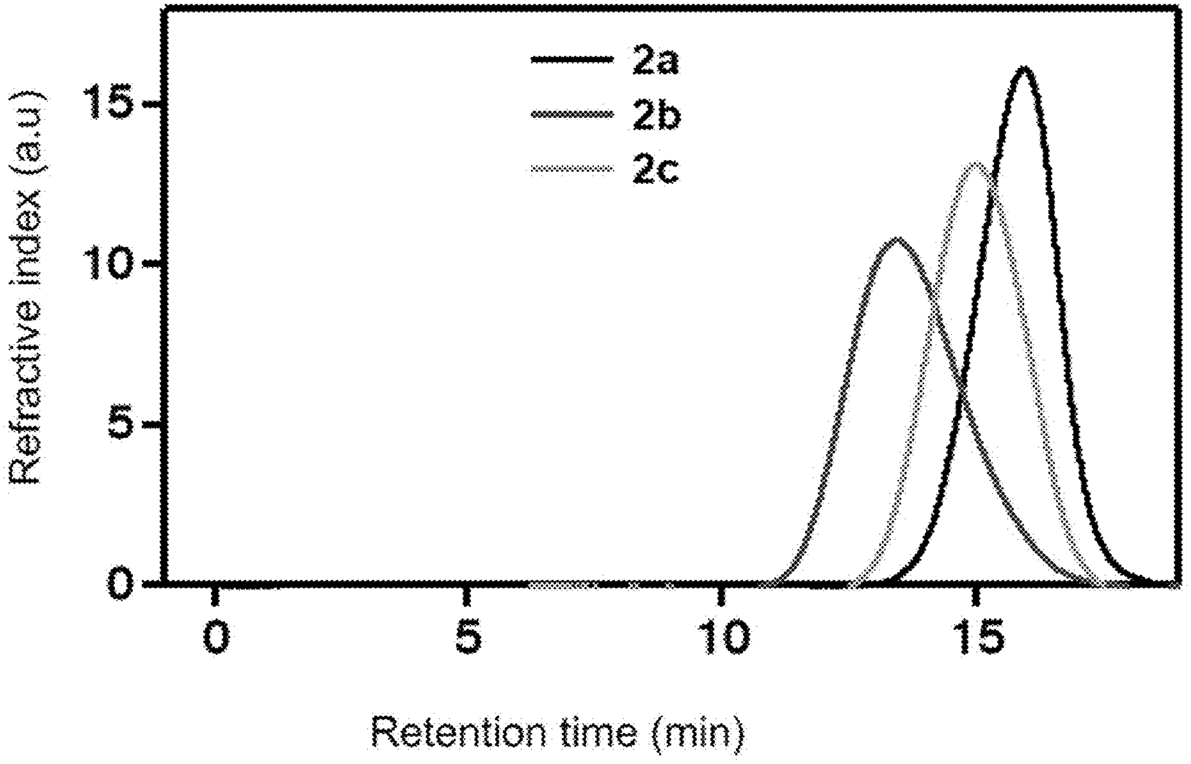
FIGS. 30A-30B: GPC analysis of 4 with co-initiators 2a-2c (FIG. 30A), and 4 with photoinitiators 1a-1f and BP (FIG. 30B).
Figure 30B:
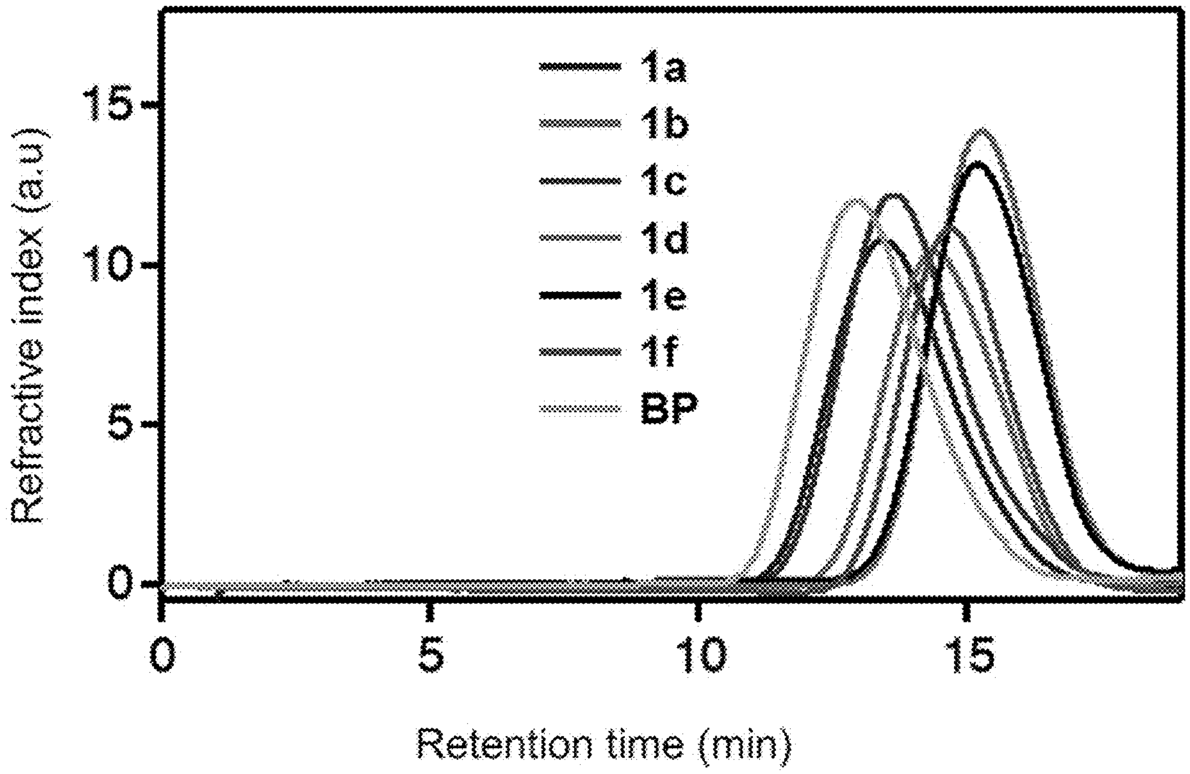

FIGS. 30A-30B depict a GPC analysis of 4 with co-initiators 2a-2c (FIG. 30A), and 4 with photoinitiators 1a-1f and BP (FIG. 30B).

TABLE 5

Influence of photon flux on polymerization under visible light illumination

| Entry | PI | CI | Monomer | Source | Ee[b] | % Conversion [c] | Mn | Mw | PDI |
|---|---|---|---|---|---|---|---|---|---|
| 1 | 1a | 2b | 3 | Purple LED | 11.8 | 13.3 | 15,042 | 24,190 | 1.6 |
| 2 | 1a | 2b | 3 | Purple LED | 24.4 | 14.9 | 21,475 | 28,963 | 1.3 |
| 3 | 1a | 2b | 3 | Purple LED | 39.3 | 13.3 | 31,632 | 44,365 | 1.4 |
| 4 | 1a | 2b | 3 | Purple LED | 51.1 | 16.1 | 31,481 | 46,079 | 1.4 |
| 5 | 1a | 2b | 3 | Purple Led strip | 1.5 | 10.6 | 47,150 | 33,383 | 1.4 |
| 6 | 1e | 2b | 3 | Purple LED | 11.8 | 15.1 | 29.020 | 42,353 | 1.4 |
| 7 | 1e | 2b | 3 | Purple LED | 24.4 | 18.1 | 21,232 | 34,640 | 1.6 |
| 8 | 1e | 2b | 3 | Purple LED | 39.3 | 16.5 | 26,624 | 41,678 | 1.5 |
| 9 | 1e | 2b | 3 | Purple LED | 51.1 | 17.8 | 25,540 | 42,030 | 1.6 |
| 10 | 1e | 2b | 3 | Purple Led strip | 1.5 | 16.8 | 25,562 | 39,114 | 1.5 |

[a] M = Monomer; PI = Photoinitiator; CI = Co-initiator. [PI] = 5 mM, [CI] = 2b (triethanolamine) 5 mM, [monomer] = 3.12M, solvent = $CH_3CN$. Photopolymerizations were carried out under purple LED illumination with a flux density range from 11.8 to 51.1 mW/$cm^2$. The values reported are an average of three runs.

[b] Ee = Flux density (mW/$cm^2$) measured by Thor PM100D power meter console using S121C photodiode power sensor by keeping the sample at a distance of 10 cm from the light source. For purple LED strip, the sample was kept at the middle irradiation set up at a distance of ~2 cm from the light source (Refer to ESI).

[c] Conversions determined by gravimetric analysis and carry an error of 3%.

Figure 31A:
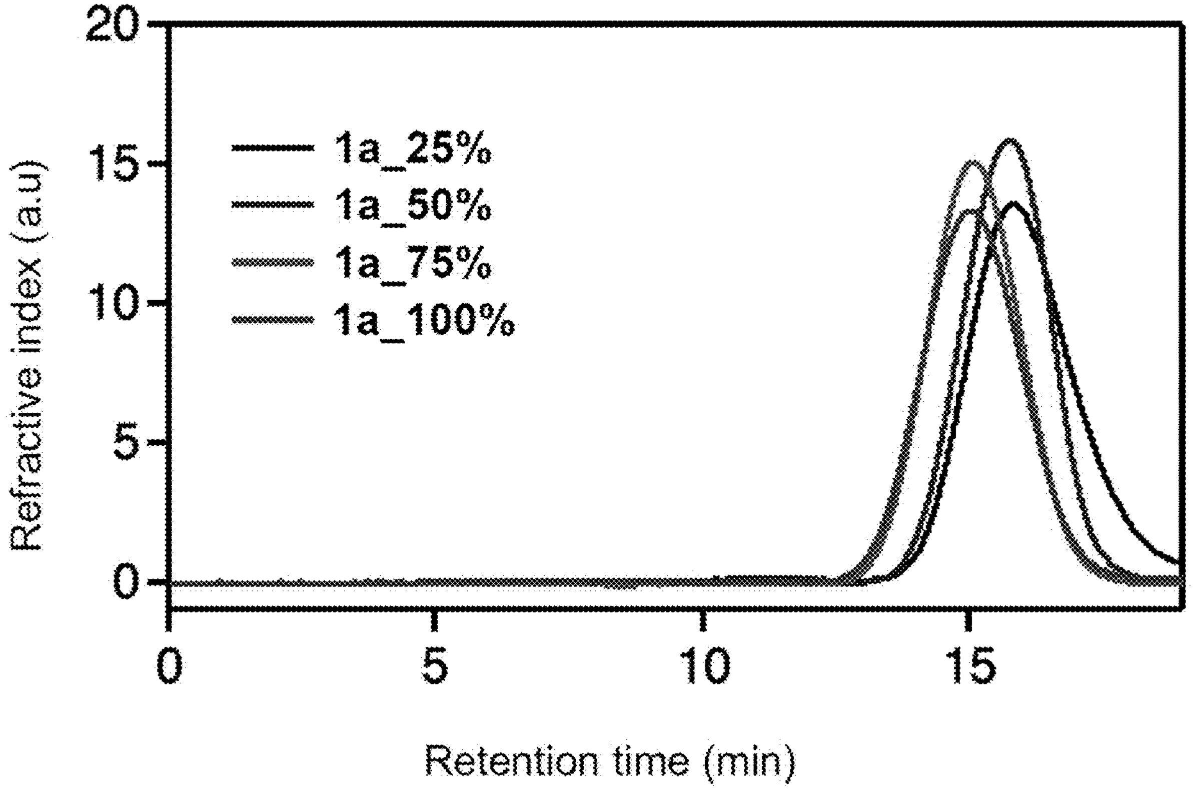
FIGS. 31A-31B: Effect of photon flux on photopolymerization efficiencies for 1a (FIG. 31A) and for 1e (FIG. 31B).
Figure 31B:
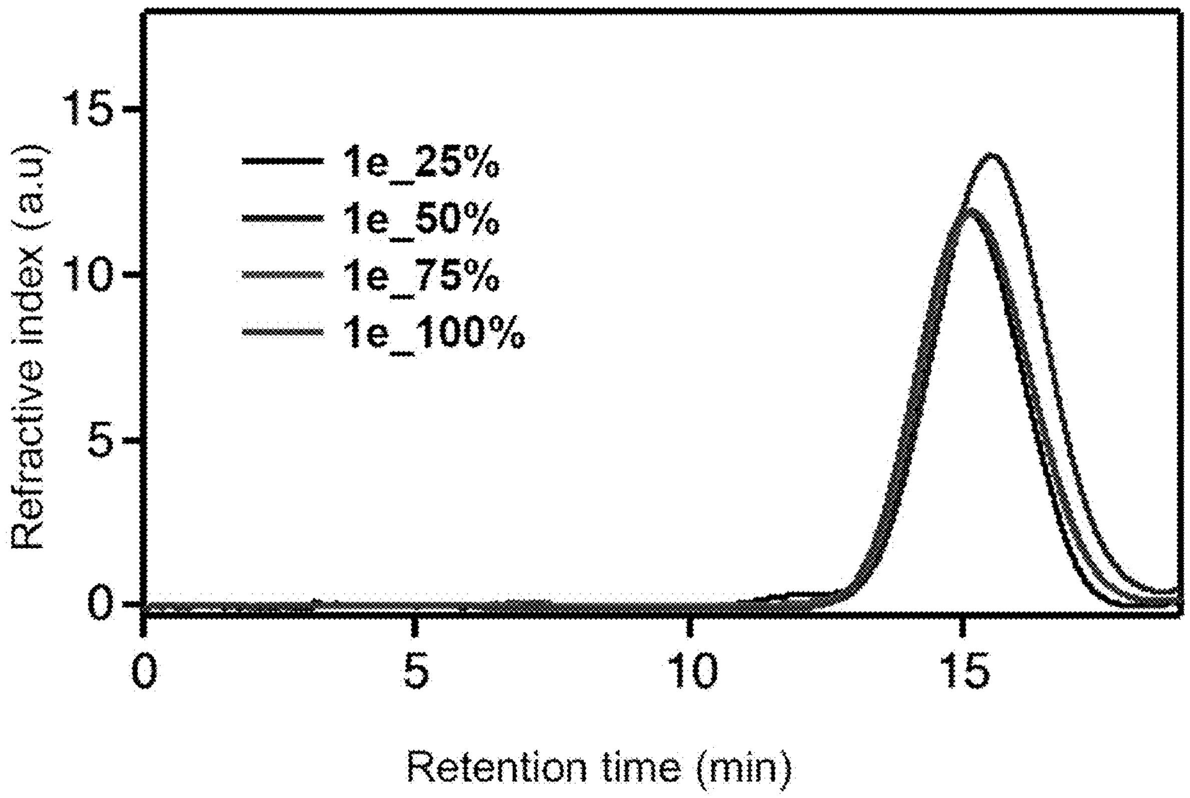

FIGS. 31A-31B show the effect of photon flux on photopolymerization efficiencies for 1a (FIG. 31A) and for 1e (FIG. 31B).

TABLE 6

Evaluation of efficiency of photopolymerization of methylmethacrylate 3 with pjhotoinitiators of same optical density[a]

| Entry | PI | [1] mM | ε ($M^{-1}$ $cm^{-1}$) | % Conversion [b] | Mn | Mw | PDI |
|---|---|---|---|---|---|---|---|
| 1 | 1a | 40 | 6.5 | 32 | 7,906 | 11,295 | 1.4 |
| 2 | 1b | 46 | 5.6 | 32 | 7,758 | 11,597 | 1.5 |
| 3 | 1c | 92 | 2.8 | 31 | 7.032 | 11,529 | 1.6 |
| 4 | 1d | 14 | 17.8 | 29 | 10,542 | 17,421 | 1.6 |
| 5 | 1e | 7 | 38.8 | 20 | 18,540 | 32,144 | 1.7 |
| 6 | 1f | 57 | 4.6 | 36 | 7,399 | 10,936 | 1.4 |
| 7 | BP | 247 | 1.0 | 24 | 5,872 | 8,611 | 1.4 |

[a]M = Monomer; PI = Photoinitiator; CI = co-initiator. [CI] = [PI]. [CI] = 2b (triethanolamine), 3 = [monomer] = 3.12M, solvent = $CH_3CN$. Photopolymerization were carried out purple with a LED strip illumination with a flux density of 1.5 $mW/cm^2$. Irradiation was done for 3 h.
[b] Conversions determined by gravimetric analysis and carry an error of 3%. The values reported are an average of three runs.

Figure 32:
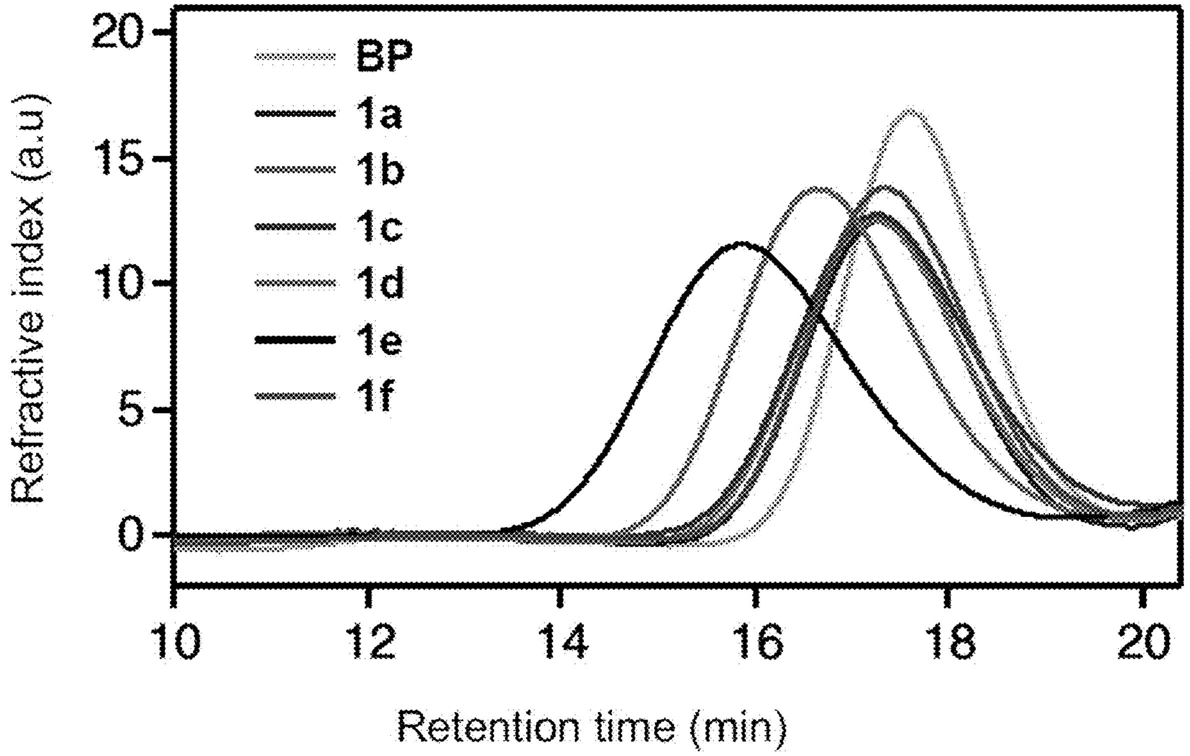
FIG. 32: Photopolymerization of methylmethacrylate 3 by employing photoinitiators with the same optical density (OD) at ~390 nm.

FIG. 32 shows the photopolymerization of methylmethacrylate 3 by employing photoinitiators with the same optical density (OD) at ~390 nm.

TABLE 7

Evaluation of efficienicy of photopolymerization of methylmethacrylate 3 with photoinitiators of same optical density and same concentration of coinitiator[a]

| Entry | PI | [1] mM | ε ($M^{-1}$ $cm^{-1}$) | % Conversion [b] | Mn | Mw | PDI |
|---|---|---|---|---|---|---|---|
| 1 | 1a | 40 | 6.5 | 17.5 | 20,738 | 33,730 | 1.6 |
| 2 | 1b | 46 | 5.6 | 14.3 | 34,425 | 50,502 | 1.4 |
| 3 | 1c | 92 | 2.8 | 19.7 | 22,246 | 41,014 | 1.8 |
| 4 | 1d | 14 | 17.8 | 30.8 | 21,676 | 36,430 | 1.6 |
| 5 | 1e | 7 | 38.8 | 27.6 | 29,113 | 44,676 | 1.5 |
| 6 | 1e[c] | 7 | 38.8 | 17.0 | 44,655 | 68,836 | 1.5 |
| 7 | 1e[d] | 7 | 38.8 | 37.0 | 18,525 | 30,619 | 1.6 |
| 8 | 1f | 57 | 4.6 | 25.7 | 25,448 | 40,201 | 1.5 |
| 9 | BP | 247 | 1.0 | 19.2 | 21,509 | 39,761 | 1.8 |

[a]M = Monomer; CI = co-initiator. [CI] = 2b (Triethanolamine) 7 mM. [Monomer] = 3.12M, solvent = $CH_3CN$.
[b] 2b = 0.7 mM and
[c]2b = 15 mM. Photopolymerization were carried out with a purple LED strip illumination with a flux density of 1.5 $mW/cm^2$. Irradiation was done for 3 h. Ee = Flux density ($mW/cm^2$) measured by Newport/spectra physics 407A Portable Laser Power Meter by keeping the sample at a distance of ~2 cm from the light source.
[d]Conversions determined by gravimetric analysis and carry an error of 3%. The values reported are an average of three runs.

Figure 33A:
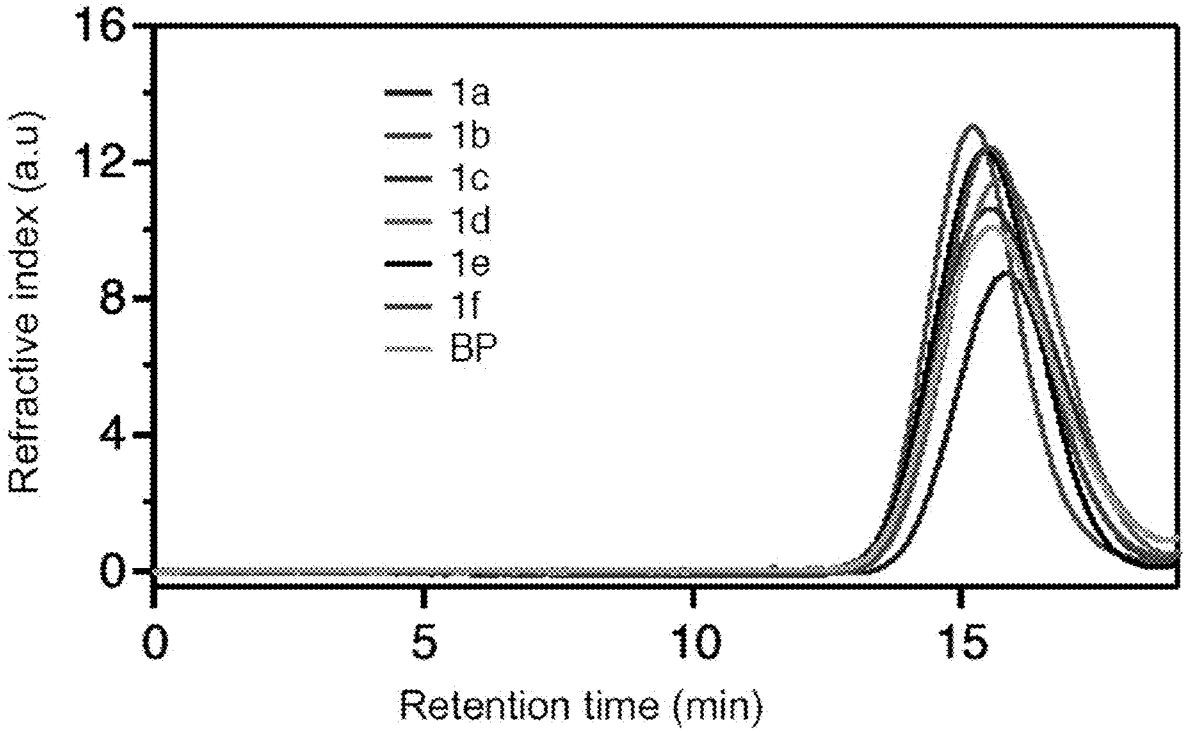
FIGS. 33A-33B: GPC traces for polymer 4 for photopolymerization efficiciencies for 1a-1f and BP with keeping 2b coinitiator concentration the same (FIG. 33A), and photopolymerization efficiency of 1e with 0.7 mM and 15 mM concentration of 2b.
Figure 33B:
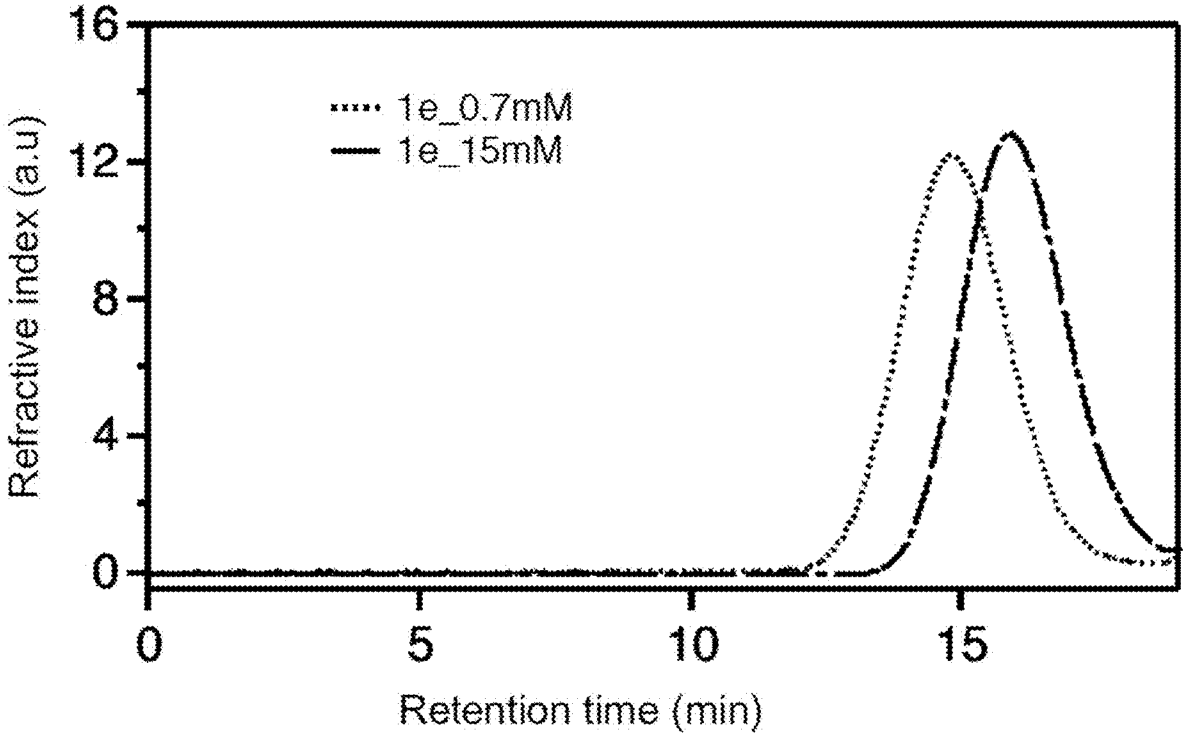

FIGS. 33A-33B show the GPC traces for polymer 4 for photopolymerization efficiciencies for 1a-1f and BP with keeping 2b coinitiator concentration the same (FIG. 33A), and photopolymerization efficiency of 1e with 0.7 mM and 15 mM concentration of 2b.

NMR Studies

Figure 34A:
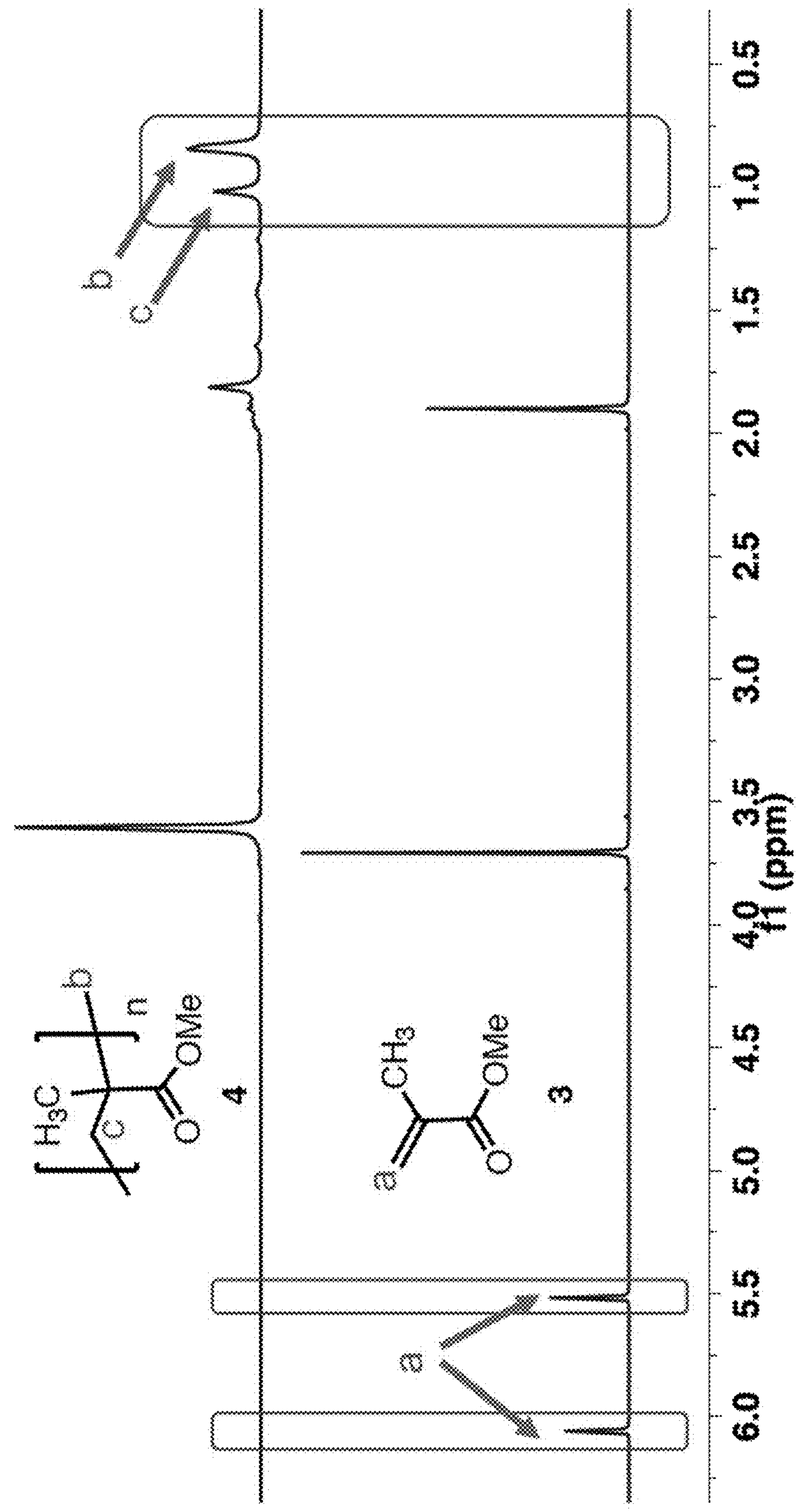
FIGS. 34A-34B: $^{1}H$ NMR analysis of the polymers 4 FIG. 34A) and 6 (FIG. 34B).
Figure 34B:
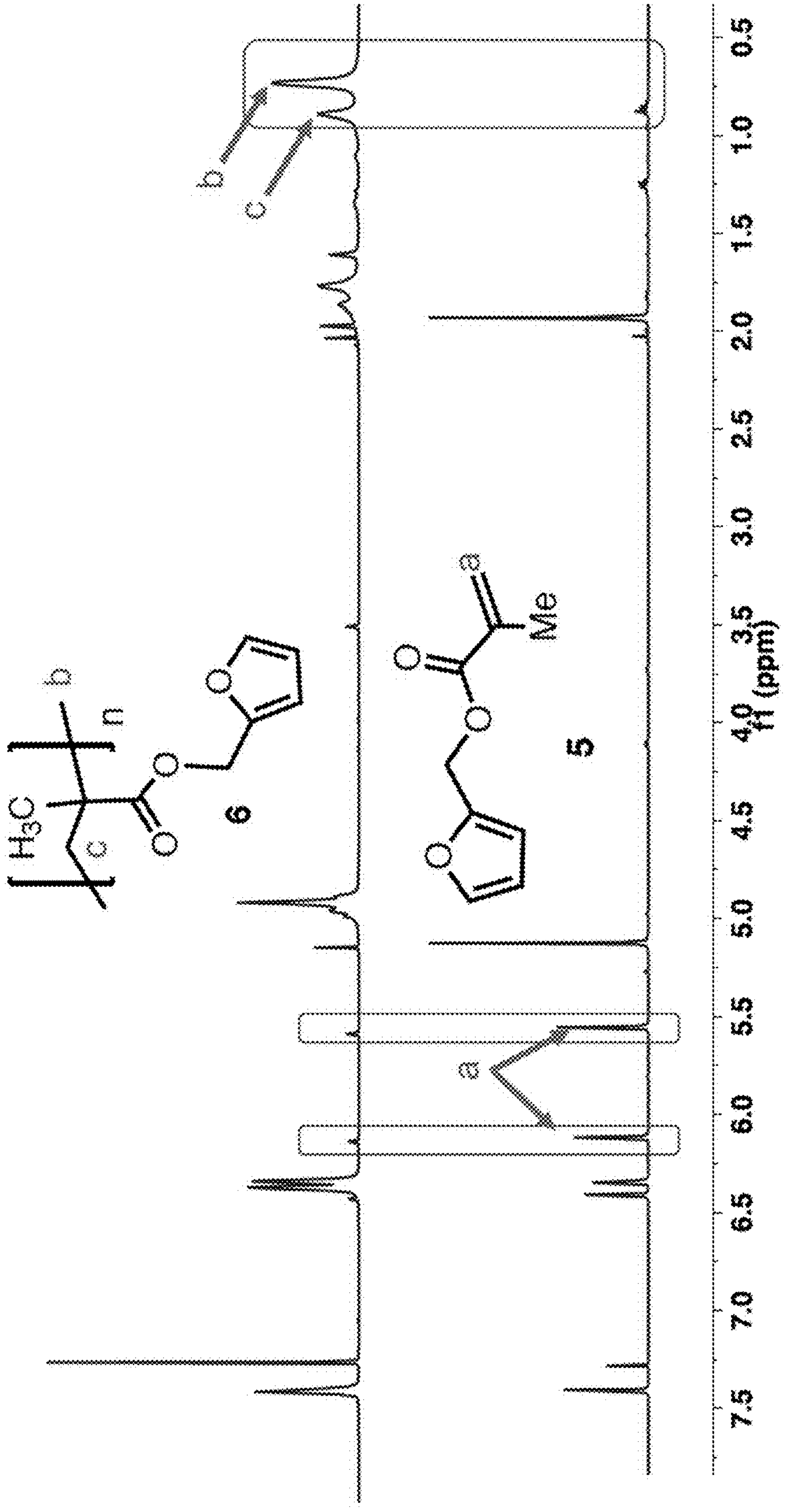

FIGS. 34A-34B show an NMR analysis of the polymers 4 (FIG. 34A) and 6 (FIG. 34B).

IR Studies

Figure 35:
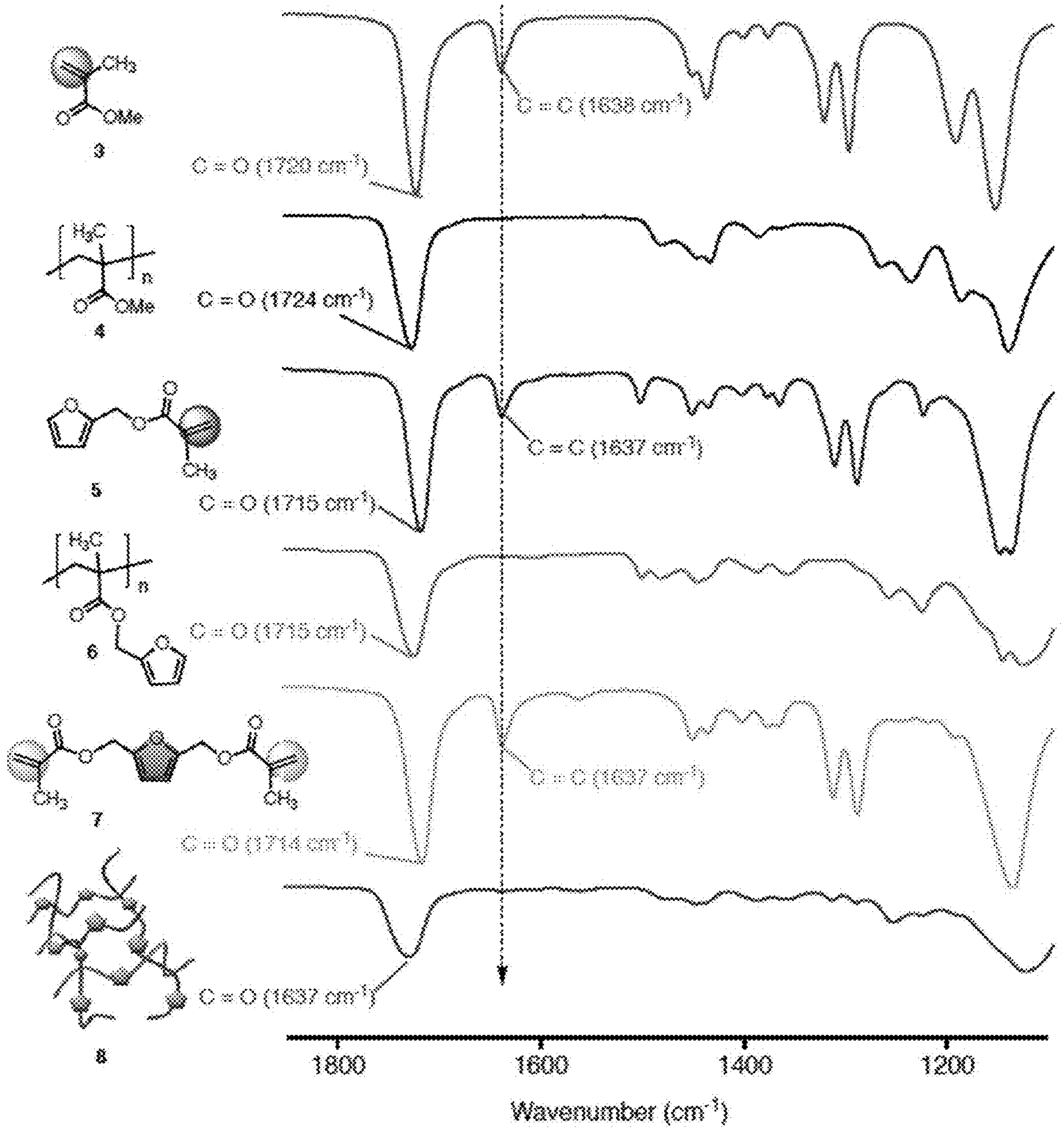
FIG. 35: Attenuated total reflection fourier transform infra-red (ATR-FTIR) spectra of 3, 4, 5, 6, 7, and 8.

FIG. 35 shows the attenuated total reflection fourier transform infra-red (ATR-FTIR) spectra of 3, 4, 5, 6, 7, and 8.

TGA

Figure 36:
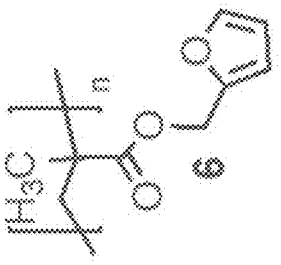
FIG. 36: Thermogravimetric analysis of 6 and 8.
Figure 36:
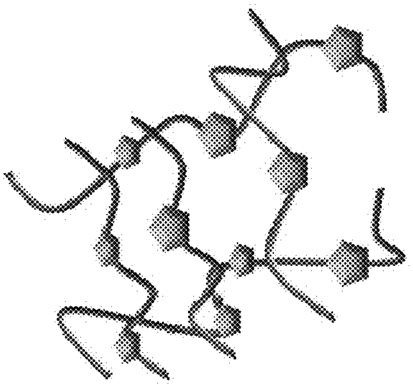
Figure 36:
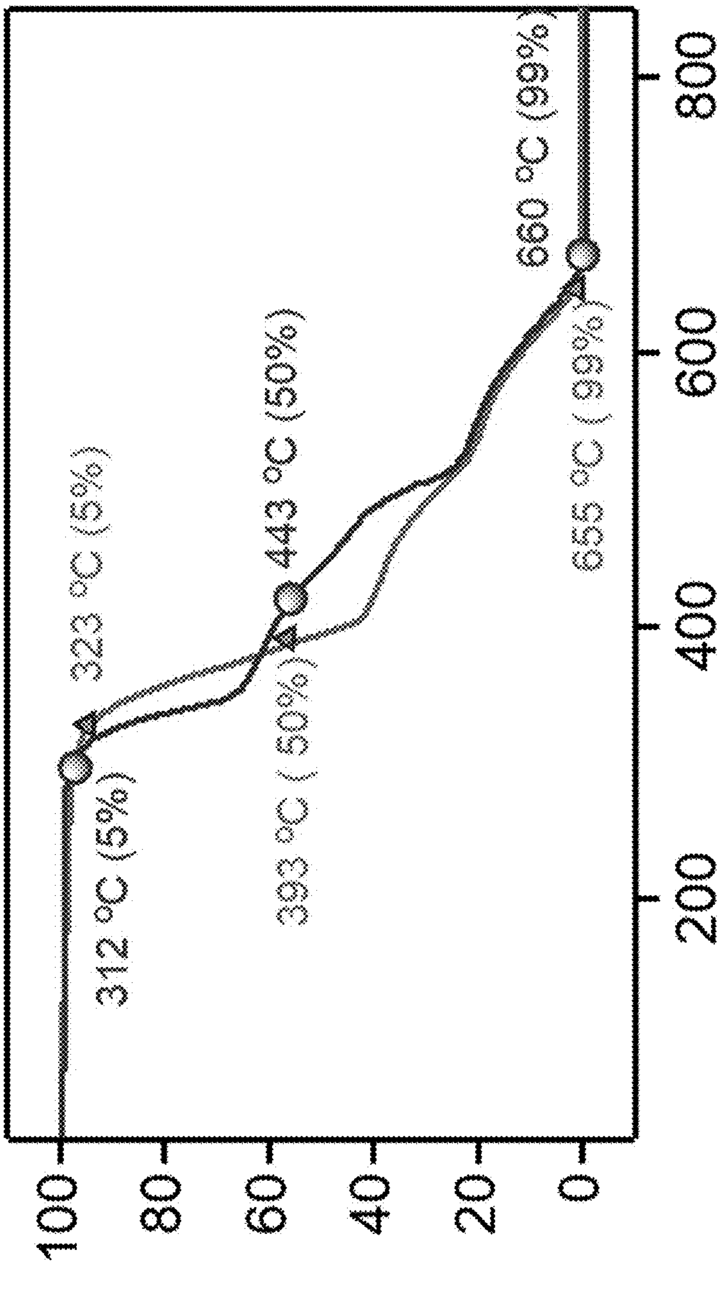
Figure 37A:
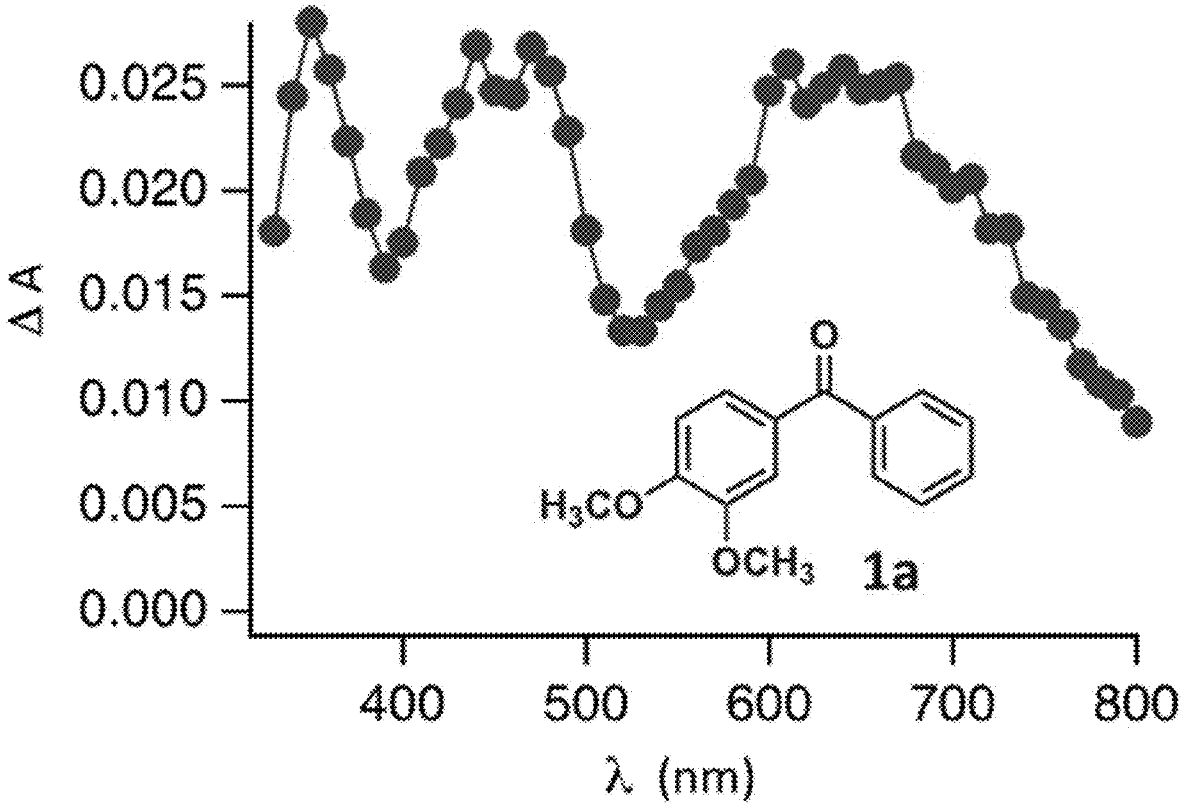
FIGS. 37A-37D: Transient absorption spectra of 1a (FIG. 37A), 1e (FIG. 37B), 1c (FIG. 37C), and 1d (FIG. 37D) deoxygenated acetonitrile solutions at 0-1 μs after the laser pulse (355 nm, 5 ns pulse width).
Figure 37B:
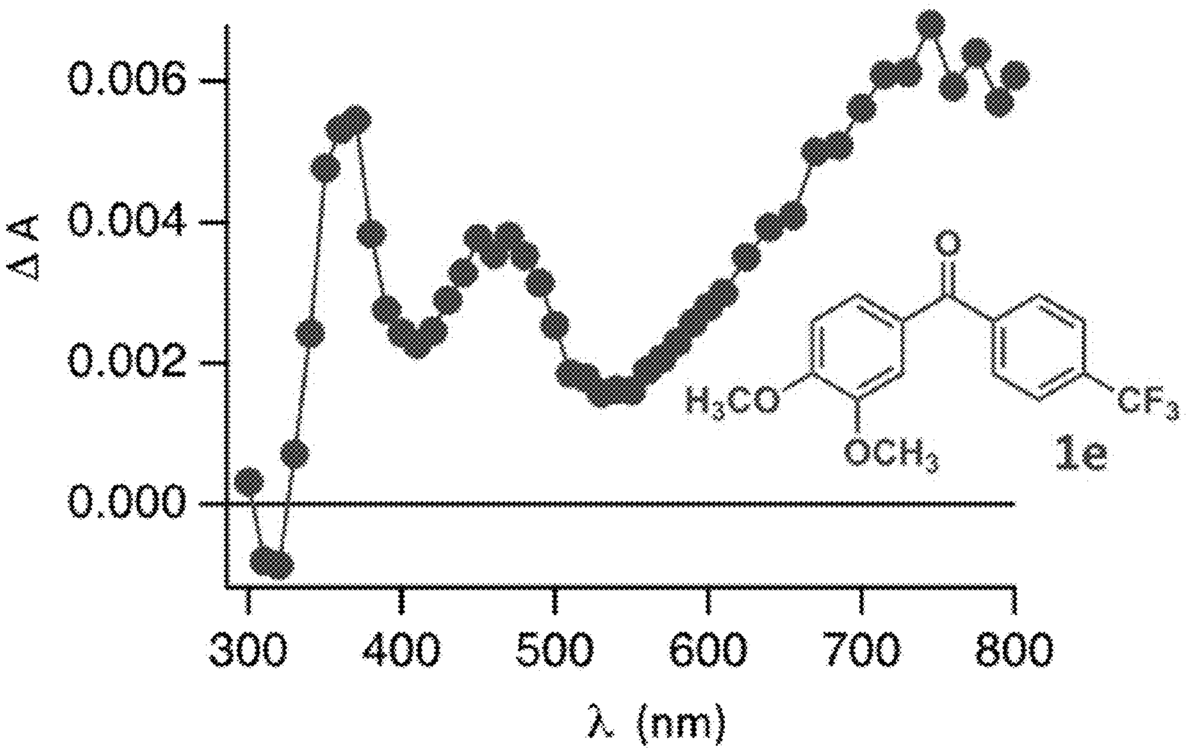
Figure 37C:
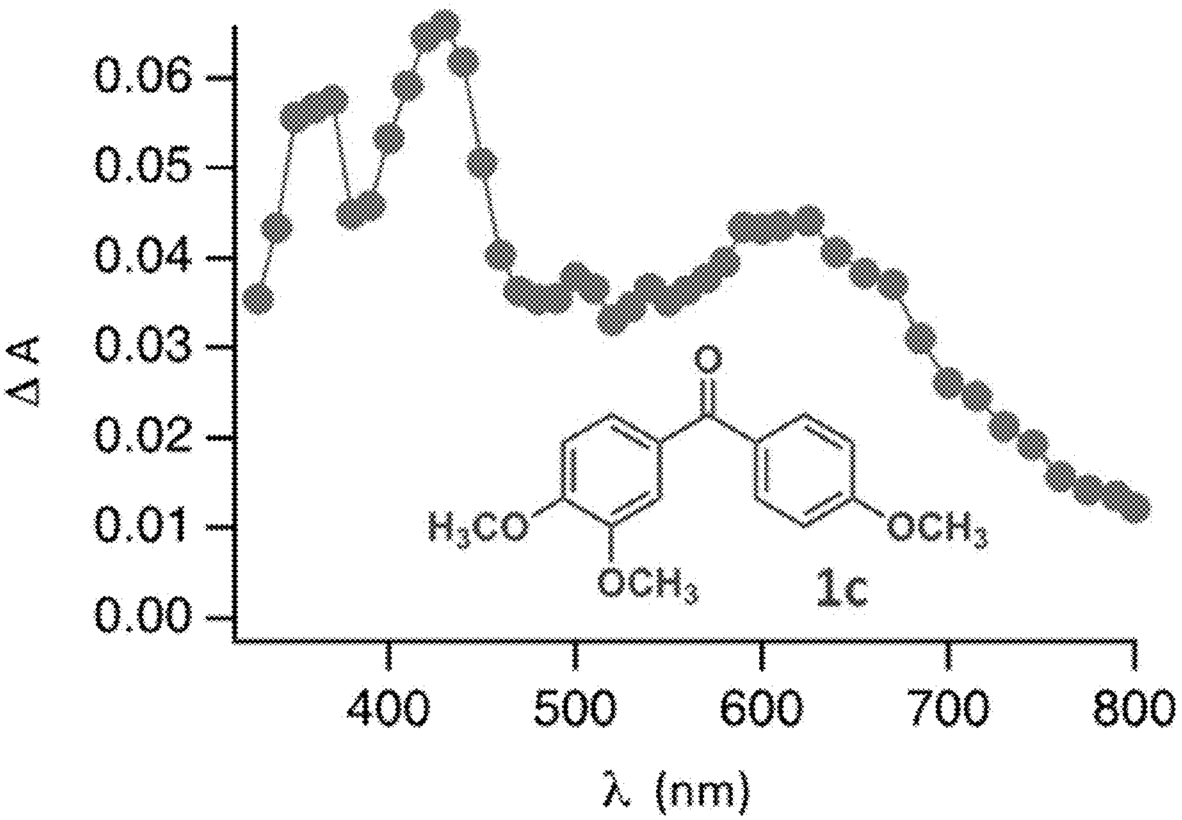
Figure 37D:
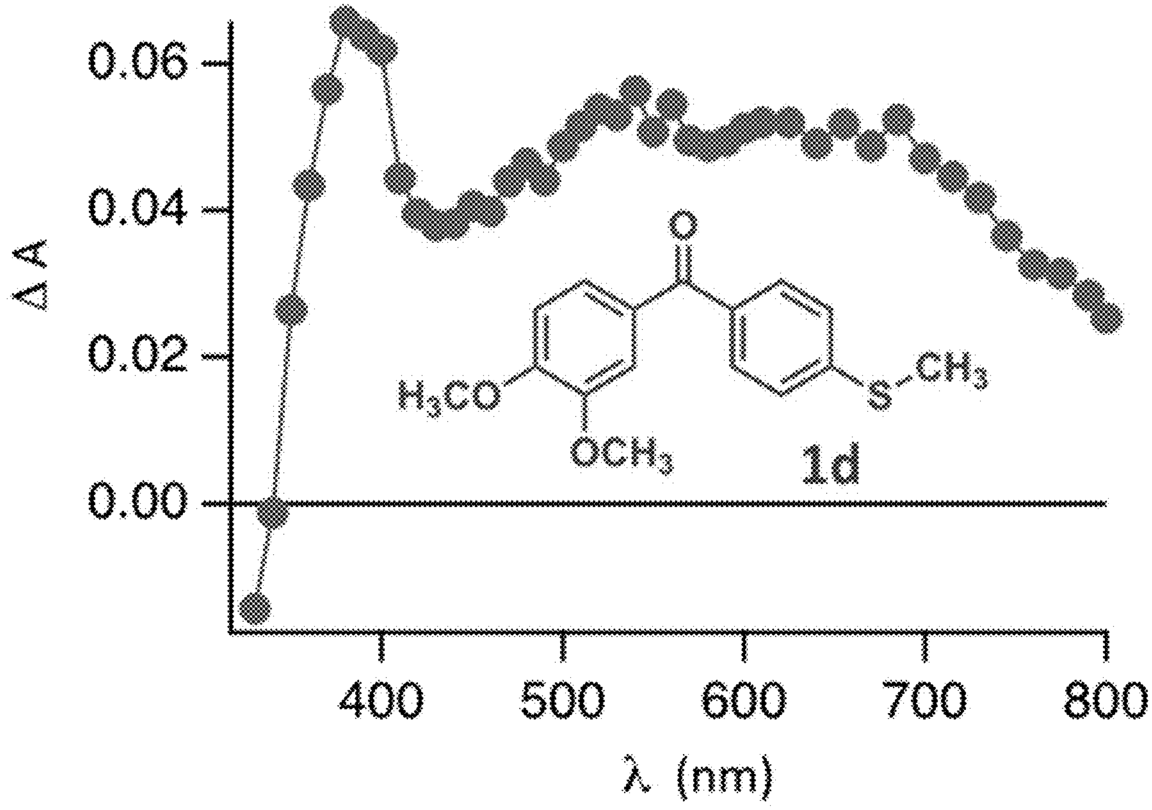

FIG. 36 shows a thermogravimetric analysis of 6 and 8.

Certain embodiments of the compositions and methods disclosed herein are defined in the above examples. It should be understood that these examples, while indicating particular embodiments of the invention, are given by way of illustration only. From the above discussion and these examples, one skilled in the art can ascertain the essential characteristics of this disclosure, and without departing from the spirit and scope thereof, can make various changes and modifications to adapt the compositions and methods described herein to various usages and conditions. Various changes may be made and equivalents may be substituted for elements thereof without departing from the essential scope of the disclosure. In addition, many modifications may be made to adapt a particular situation or material to the teachings of the disclosure without departing from the essential scope thereof.

What is claimed is:

1. A composition comprising Formula I, Formula II, Formula III, or Formula IV:

Formula I

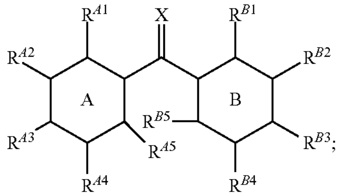

-continued

Formula II

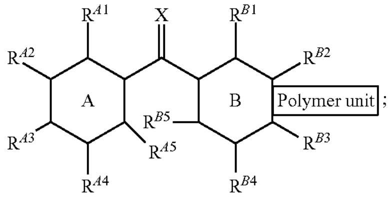

Formula III

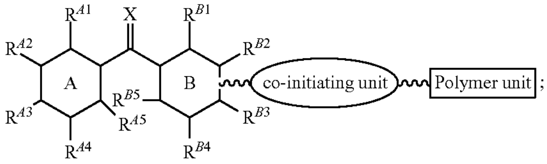

or

-continued

Formula IV

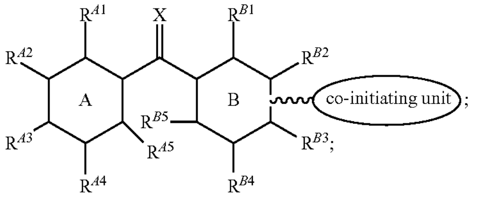

wherein:

X is O, S, NH, Ge, NC (O)-O-RC, N-O-C(O)$R^C$, or NO-$R^C$, wherein $R^C$ is alkyl, aryl, or heteroaryl;

substituents $R^{A1}$, $R^{A2}$, $R^{A5}$, and $R^{B1}$ to RB5 are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes;

substituents $R^{A3}$ and $R^{A4}$ are each methoxy;

the co-initiating unit is an amine, thiol, or any hydrogen donating atom; and the polymer unit is a vinyl, stryl, acryl, or a cyclic monomer selected from lactones, epoxides, lactides, lactams, silicon-containing cyclic monomers, and cyclic carbonates.

2. The composition of claim 1, wherein the Formula I, Formula II, Formula III, or Formula IV comprises a compound of Formula A:

Formula A

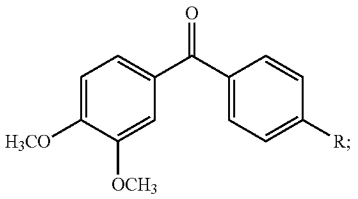

wherein R is H, alkyl, alkoxy, halo, halo-substituted alkyl, or thioalkyl.

3. The composition of claim 2, wherein the compound of Formula A is compound 1*a*, 1*b*, 1*c*, 1*d*, or 1*e*:

1a

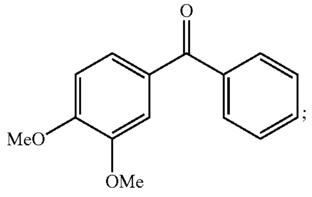

-continued

1b

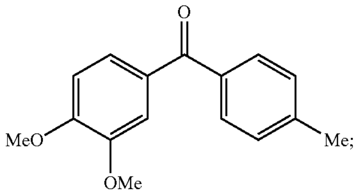

1c

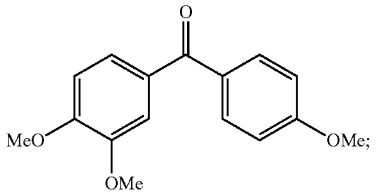

1d

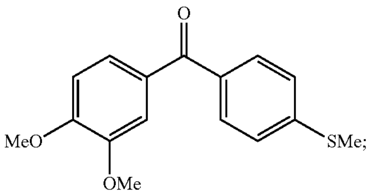

or

1e

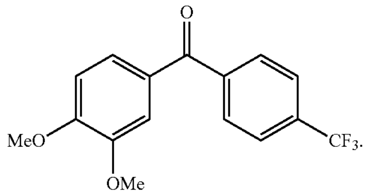

4. The composition of claim 1, wherein the Formula I, Formula II, Formula III, or Formula IV is compound 1*j* or compound 1*g*:

1j

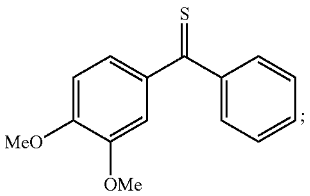

1g

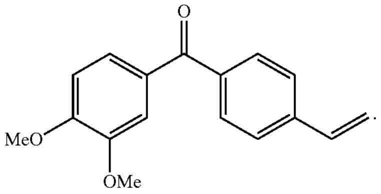

5. The composition of claim 1, wherein the Formula I, Formula II, Formula III, or Formula IV comprises compound 1*h* or compound 1*i*:

1h

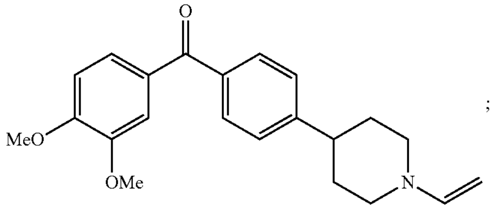

;

1i

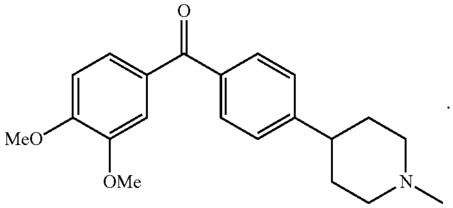

.

6. A method of making a polymer, the method comprising exposing a biomass derived photoinitiator and a monomer to light to make a polymer, wherein the biomass derived photoinitiator comprises Formula I, Formula II, Formula III, or Formula IV:

Formula I

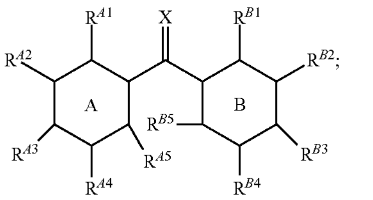

Formula II

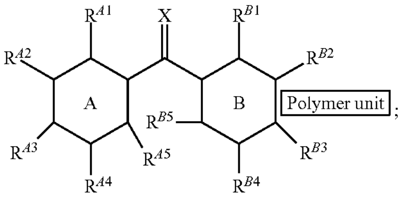

Formula III

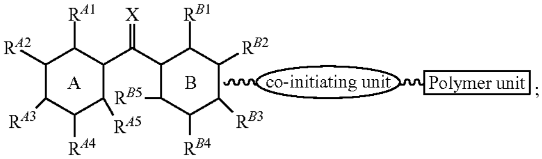

or

Formula IV

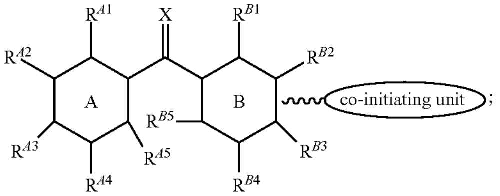

wherein:

A or B is a ring derived from biomass;

X is O, S, NH, Ge, NC (O)-O-$R^C$, N-O-C(O)$R^C$, or NO-$R^C$, wherein $R^C$ is alkyl, aryl, or heteroaryl;

substituents $R^{A1}$ to $R^{A5}$ and $R^{B1}$ to $R^{B5}$ are any combination of H, alkyl, alkene, alkynes, aryl, heterocyclic, alkenyl halides, unsaturated enones, unsaturated ketones, unsaturated amides, unsaturated alcohols, unsaturated amines, unsaturated thiols, phosphonates, carboxylates, sulfonates, nitriles, thioethers, thioamides, thioketones, azides, sulfides, disulfides, ethers, epoxides, nitrates, nitrites, nitro compounds, nitroso compounds, alkyl ketoesters, acylgermanes, metallocenes, organosilanes, oximes, imides, cyanates, isocyanates, thiocyanates, isothiocyanates, sulfoxides, sulfones, sulfites, phosphites, thial, phosphines, and aldehydes;

the co-initiating unit is an amine, thiol, or any hydrogen donating atom; and the polymer unit is a vinyl, stryl, acryl, or a cyclic monomer selected from lactones, epoxides, lactides, lactams, silicon-containing cyclic monomers, and cyclic carbonates.

7. The method of claim 6, wherein the biomass derived photoinitiator comprising Formula I, Formula II, Formula III, or Formula IV comprises a compound of Formula A:

Formula A

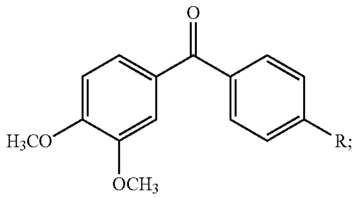

wherein R is H, alkyl, alkoxy, halo, halo-substituted alkyl, or thioalkyl.

8. The method of claim 7, wherein the biomass derived photoinitiator comprising Formula I, Formula II, Formula III, or Formula IV is compound 1*a*, compound 1*b*, compound 1*c*, compound 1*d*, or compound 1*e*:

1a

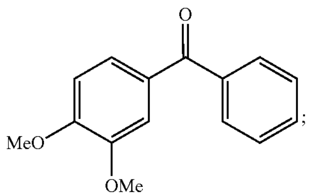

1b

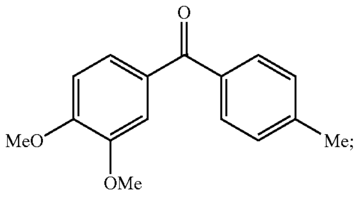

1c

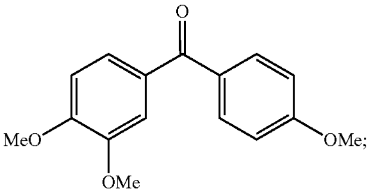

-continued

1d

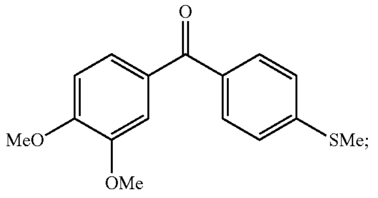

1e

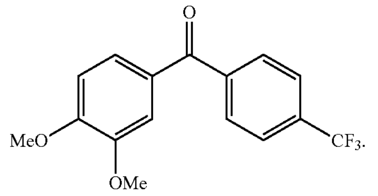

9. The method of claim 6, wherein the light is visible light.

10. The method of claim 6, wherein the light is purple light.

11. The method of claim 6, wherein the monomer is monomer 3, biomass derived monomer 5, or biomass derived furfuryl dimethacrylate monomer 7:

3

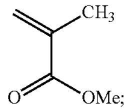

5

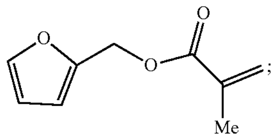

; or

7

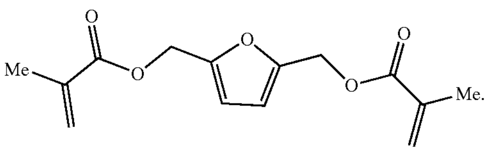

12. The method of claim 6, wherein the polymer is one of polymer 4:

4

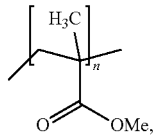

wherein n is an integer;

polymer 6:

6

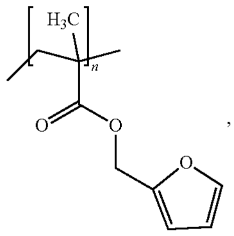

wherein n is an integer; or a crosslinked 2,5-bis(hydroxymethyl)furan dimethacrylate (FDMA) polymer.

13. The method of claim 6, wherein the biomass derived photoinitiator comprising Formula I, Formula II, Formula III, or Formula IV is compound 1*j* or compound 1*g*:

1j

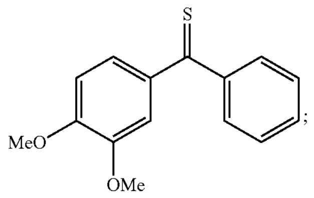

; or

1g

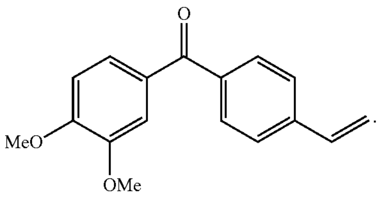

14. The method of claim 6, wherein the biomass derived photoinitiator comprising Formula I, Formula II, Formula III, or Formula IV comprises is compound 1*h* or compound 1*i*:

1h

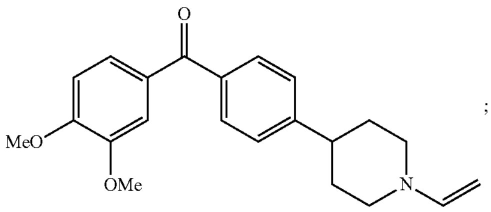

; or

1i

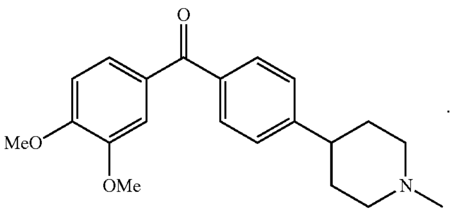

.

15. The method of claim 6, wherein a co-initiator is exposed to the light with the monomer and the photoinitiator.

16. A method of making a benzophenone derivative, the method 45. comprising:

synthesizing a benzhydrol derivative having Formula B:

Formula B

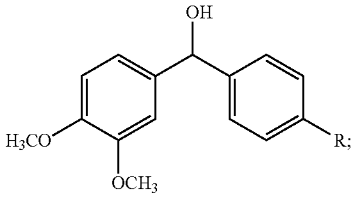

and oxidizing the benzhydrol derivative to form a benzophenone derivative;

wherein R is H, alkyl, alkoxy, halo, halo-substituted alkyl, or thioalkyl.

17. The method of claim 16, wherein the benzhydrol derivative is oxidized with $MnO_2$.

18. The method of claim 16, wherein the benzhydrol derivative is synthesized through a Grignard reaction with veratraldehyde 9:

9

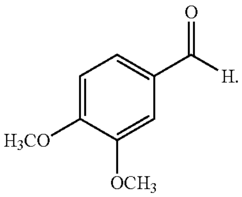

19. The method of claim 18, wherein 4-bromo benzene derivatives are reacted with the veratraldehyde 9 in the Grignard reaction.

* * * * *